US012637453B2

(12) United States Patent
Gray et al.

(10) Patent No.: US 12,637,453 B2
(45) Date of Patent: May 26, 2026

(54) PYRAZOLOPYRIDINE INHIBITORS OF C-JUN-N-TERMINAL KINASES AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US); Yao Liu, Brookline, MA (US); Yang Gao, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 976 days.

(21) Appl. No.: 17/413,299

(22) PCT Filed: Dec. 13, 2019

(86) PCT No.: PCT/US2019/066201
§ 371 (c)(1),
(2) Date: Jun. 11, 2021

(87) PCT Pub. No.: WO2020/123925
PCT Pub. Date: Jun. 18, 2020

(65) Prior Publication Data
US 2022/0073512 A1 Mar. 10, 2022

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC ............................... C07D 471/04; A61P 35/00
See application file for complete search history.

(56) References Cited

U.S. PATENT DOCUMENTS

| | | | |
|---|---|---|---|
| 4,231,938 | A | 11/1980 | Monaghan et al. |
| 4,270,537 | A | 6/1981 | Romaine et al. |
| 4,596,556 | A | 6/1986 | Morrow et al. |
| 4,782,084 | A | 11/1988 | Vyas et al. |
| 4,790,824 | A | 12/1988 | Morrow et al. |
| 4,885,314 | A | 12/1989 | Vyas et al. |
| 4,886,499 | A | 12/1989 | Cirelli et al. |
| 4,940,460 | A | 7/1990 | Casey et al. |
| 4,941,880 | A | 7/1990 | Burns et al. |
| 5,015,235 | A | 5/1991 | Crossman et al. |
| 5,064,413 | A | 11/1991 | McKinnon et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby et al. |
| 5,334,144 | A | 8/1994 | Alchas et al. |
| 5,339,163 | A | 8/1994 | Homma et al. |
| 5,383,851 | A | 1/1995 | McKinnon et al. |
| 5,417,662 | A | 5/1995 | Hjertman et al. |
| 5,420,245 | A | 5/1995 | Brown et al. |
| 5,466,220 | A | 11/1995 | Brenneman et al. |
| 5,480,381 | A | 1/1996 | Weston et al. |
| 5,484,596 | A | 1/1996 | Hanna et al. |
| 5,503,627 | A | 4/1996 | McKinnon et al. |
| 5,510,510 | A | 4/1996 | Patel et al. |
| 5,520,639 | A | 5/1996 | Peterson et al. |
| 5,523,430 | A | 6/1996 | Patel et al. |
| 5,527,288 | A | 6/1996 | Gross et al. |
| 5,532,359 | A | 7/1996 | Marsters et al. |
| 5,569,189 | A | 10/1996 | Parsons et al. |
| 5,571,792 | A | 11/1996 | Bolton et al. |
| 5,589,485 | A | 12/1996 | Hocolowski et al. |
| 5,599,302 | A | 2/1997 | Lilley et al. |
| 5,602,098 | A | 2/1997 | Sebti et al. |
| 5,643,958 | A | 7/1997 | Iwasawa et al. |
| 5,649,912 | A | 7/1997 | Peterson et al. |
| 5,661,152 | A | 8/1997 | Bishop et al. |
| 5,704,911 | A | 1/1998 | Parsons et al. |
| 5,750,567 | A | 5/1998 | Baudoin et al. |
| 5,856,439 | A | 1/1999 | Clerc et al. |
| 5,889,053 | A | 3/1999 | Baudoin et al. |
| 5,893,397 | A | 4/1999 | Peterson et al. |

(Continued)

FOREIGN PATENT DOCUMENTS

| | | | |
|---|---|---|---|
| CA | 2486101 | A1 | 11/2003 |
| CA | 2503646 | A1 | 5/2004 |

(Continued)

OTHER PUBLICATIONS

International Search Report and Written Opinion from PCT/US2019/066201, mailed Feb. 7, 2020.
International Preliminary Report on Patentability from PCT/US2019/066201, mailed Jun. 24, 2021.
Extended European Search Report for EP 19168422.4, mailed on Aug. 13, 2019.
International Search Report and Written Opinion for PCT/US2012/065618, mailed Mar. 19, 2013.
International Preliminary Report on Patentability for PCT/US2012/065618, mailed May 30, 2014.
International Search Report and Written Opinion for PCT/US2013/065708, mailed Feb. 4, 2014.
International Preliminary Report on Patentability for PCT/US2013/065708, mailed Apr. 30, 2015.
International Search Report and Written Opinion for PCT/US2013/065689, mailed Mar. 4, 2014.

(Continued)

*Primary Examiner* — James H Alstrum-Acevedo
*Assistant Examiner* — Lauren Wells
(74) *Attorney, Agent, or Firm* — Nielsen IP Law LLC

(57) ABSTRACT

Provided herein are compounds of Formula (I), and pharmaceutically acceptable salts, solvates, hydrates, polymorphs, co-crystals, tautomers, stereoisomers, isotopologues, prodrugs, and compositions thereof. Also provided are methods and kits involving the inventive compounds or compositions for treating and/or preventing diseases (e.g., proliferative diseases (e.g., cancers and benign neoplasms), inflammatory diseases (e.g., rheumatoid arthritis), and vascular diseases (e.g., atherosclerosis) in a subject. Provided are methods of inhibiting a JNK (e.g., JNK1, JNK2, or JNK3) in a subject.

10 Claims, 2 Drawing Sheets

(56) References Cited

U.S. PATENT DOCUMENTS

| | | | |
|---|---|---|---|
| 5,925,641 | A | 7/1999 | Kanda et al. |
| 5,936,097 | A | 8/1999 | Commercon et al. |
| 5,993,412 | A | 11/1999 | Deily et al. |
| 6,069,134 | A | 5/2000 | Roth et al. |
| 6,143,764 | A | 11/2000 | Kubo et al. |
| 6,214,852 | B1 | 4/2001 | Kim et al. |
| 6,329,380 | B1 | 12/2001 | Goulet et al. |
| 6,921,763 | B2 | 7/2005 | Hirst et al. |
| 6,939,874 | B2 | 9/2005 | Harmange et al. |
| 7,115,617 | B2 | 10/2006 | Buchanan et al. |
| 7,312,225 | B2 | 12/2007 | Luecking et al. |
| 7,884,117 | B2 | 2/2011 | Zhang et al. |
| 7,928,140 | B2 | 4/2011 | Booker et al. |
| 8,273,765 | B2 | 9/2012 | Fancelli et al. |
| 8,394,818 | B2 | 3/2013 | Gray et al. |
| 8,765,747 | B2 | 7/2014 | Choi et al. |
| 8,877,761 | B2 | 11/2014 | Li et al. |
| 8,889,706 | B2 | 11/2014 | Gray et al. |
| 8,987,275 | B2 | 3/2015 | Gray et al. |
| 9,180,127 | B2 | 11/2015 | Gray et al. |
| 9,358,231 | B2 | 6/2016 | Gray et al. |
| 9,382,239 | B2 * | 7/2016 | Gray .................... A61K 31/437 |
| 9,505,784 | B2 | 11/2016 | Choi et al. |
| 9,670,165 | B2 | 6/2017 | Cohen et al. |
| 9,758,522 | B2 | 9/2017 | Gray et al. |
| 9,814,709 | B2 | 11/2017 | Liu et al. |
| 9,862,688 | B2 | 1/2018 | Gray et al. |
| 9,879,003 | B2 | 1/2018 | Gray et al. |
| 10,000,483 | B2 | 6/2018 | Gray et al. |
| 10,017,477 | B2 | 7/2018 | Gray et al. |
| 10,047,070 | B2 | 8/2018 | Gray et al. |
| 10,112,927 | B2 | 10/2018 | Gray et al. |
| 10,144,730 | B2 | 12/2018 | Gray et al. |
| 10,336,760 | B2 | 7/2019 | Marineau et al. |
| 10,342,798 | B2 | 7/2019 | Gray et al. |
| 10,550,121 | B2 | 2/2020 | Gray et al. |
| 10,695,346 | B2 | 6/2020 | Gray et al. |
| 10,702,527 | B2 | 7/2020 | Hammerman et al. |
| RE48,175 | E | 8/2020 | Gray et al. |
| 10,787,436 | B2 | 9/2020 | Gray et al. |
| 10,870,651 | B2 | 12/2020 | Gray et al. |
| 10,906,889 | B2 | 2/2021 | Bradley et al. |
| 10,969,394 | B2 | 4/2021 | Marto et al. |
| 10,981,903 | B2 | 4/2021 | Gray et al. |
| 11,040,957 | B2 | 6/2021 | Ciblat et al. |
| 11,142,507 | B2 | 10/2021 | Gray et al. |
| 11,306,070 | B2 | 4/2022 | Gray et al. |
| 11,325,910 | B2 | 5/2022 | Gray et al. |
| 11,826,365 | B2 | 11/2023 | Gray et al. |
| 2003/0139416 | A1 | 7/2003 | Buchanan et al. |
| 2004/0106634 | A1 | 6/2004 | Satoh et al. |
| 2004/0126359 | A1 | 7/2004 | Lamb et al. |
| 2004/0138245 | A1 | 7/2004 | Coulomb et al. |
| 2004/0209878 | A1 | 10/2004 | Guzi et al. |
| 2005/0026914 | A1 | 2/2005 | Buchanan et al. |
| 2005/0197338 | A1 | 9/2005 | Huang et al. |
| 2005/0228031 | A1 | 10/2005 | Bilodeau et al. |
| 2005/0250837 | A1 | 11/2005 | D'Mello et al. |
| 2006/0106083 | A1 | 5/2006 | Martina et al. |
| 2006/0189627 | A1 | 8/2006 | Laird et al. |
| 2006/0252748 | A1 | 11/2006 | Lindenthal et al. |
| 2007/0004705 | A1 | 1/2007 | Brasca et al. |
| 2007/0060546 | A1 | 3/2007 | Ruat et al. |
| 2007/0093537 | A1 | 4/2007 | Hynes et al. |
| 2007/0185171 | A1 | 8/2007 | Germain et al. |
| 2007/0225286 | A1 | 9/2007 | Ren et al. |
| 2007/0275963 | A1 | 11/2007 | Guzi et al. |
| 2007/0281907 | A1 | 12/2007 | Watkins |
| 2008/0039629 | A1 | 2/2008 | Ramesh et al. |
| 2008/0090849 | A1 | 4/2008 | Bordon-Pallier et al. |
| 2008/0103167 | A1 | 5/2008 | Bebernitz et al. |
| 2008/0214501 | A1 | 9/2008 | Pan et al. |
| 2008/0249079 | A1 | 10/2008 | Chen et al. |
| 2008/0300267 | A1 | 12/2008 | Okram et al. |
| 2009/0054392 | A1 | 2/2009 | Pelletier et al. |
| 2009/0054405 | A1 | 2/2009 | Booker et al. |
| 2009/0082346 | A1 | 3/2009 | Brasca et al. |
| 2009/0105250 | A1 | 4/2009 | Sim et al. |
| 2009/0111985 | A1 | 4/2009 | Ashwell et al. |
| 2009/0156582 | A1 | 6/2009 | Tsukamoto et al. |
| 2009/0221632 | A1 | 9/2009 | Fancelli et al. |
| 2010/0056524 | A1 | 3/2010 | Mciver et al. |
| 2010/0197688 | A1 | 8/2010 | Nantermet et al. |
| 2010/0254905 | A1 | 10/2010 | Honigberg et al. |
| 2011/0039873 | A1 | 2/2011 | Gaeta et al. |
| 2011/0086858 | A1 | 4/2011 | Wang et al. |
| 2011/0098280 | A1 | 4/2011 | Garcia-Echeverria et al. |
| 2011/0178070 | A1 | 7/2011 | Gong et al. |
| 2011/0207711 | A1 | 8/2011 | Katz et al. |
| 2011/0212053 | A1 | 9/2011 | Qian et al. |
| 2012/0088766 | A1 | 4/2012 | Choi et al. |
| 2012/0094999 | A1 | 4/2012 | Gray et al. |
| 2012/0165309 | A1 | 6/2012 | Takahashi et al. |
| 2012/0196865 | A1 | 8/2012 | Ruat et al. |
| 2012/0202809 | A1 | 8/2012 | Li et al. |
| 2012/0277248 | A1 | 11/2012 | Caruso et al. |
| 2012/0329771 | A1 | 12/2012 | Treu et al. |
| 2013/0040949 | A1 | 2/2013 | Gray et al. |
| 2013/0184264 | A1 | 7/2013 | Bradner et al. |
| 2013/0184287 | A1 | 7/2013 | Gray et al. |
| 2014/0187772 | A1 | 7/2014 | Bebbington et al. |
| 2014/0303112 | A1 | 10/2014 | Chen et al. |
| 2014/0309249 | A1 | 10/2014 | Gray et al. |
| 2015/0094315 | A1 | 4/2015 | Choi et al. |
| 2015/0157629 | A1 | 6/2015 | Gray et al. |
| 2015/0166532 | A1 | 6/2015 | Gray et al. |
| 2015/0203502 | A1 | 7/2015 | Cheng et al. |
| 2015/0246913 | A1 | 9/2015 | Gray et al. |
| 2015/0274728 | A1 | 10/2015 | Gray et al. |
| 2015/0291593 | A1 | 10/2015 | Bembenek et al. |
| 2016/0046636 | A1 | 2/2016 | Gray et al. |
| 2016/0122323 | A1 | 5/2016 | Gray et al. |
| 2016/0264551 | A1 | 9/2016 | Ciblat et al. |
| 2016/0264552 | A1 | 9/2016 | Bradley et al. |
| 2016/0264554 | A1 | 9/2016 | Gray et al. |
| 2016/0368910 | A1 | 12/2016 | Gray et al. |
| 2017/0044111 | A1 | 2/2017 | Gray et al. |
| 2017/0044112 | A1 | 2/2017 | Gray et al. |
| 2017/0204096 | A1 | 7/2017 | Gelin et al. |
| 2018/0093990 | A1 | 4/2018 | Gray et al. |
| 2018/0169097 | A1 | 6/2018 | Hammerman et al. |
| 2018/0319801 | A1 | 11/2018 | Gray et al. |
| 2018/0362483 | A1 | 12/2018 | Gray et al. |
| 2018/0369243 | A9 | 12/2018 | Gray et al. |
| 2019/0015411 | A9 | 1/2019 | Hammerman et al. |
| 2019/0031642 | A1 | 1/2019 | Gray et al. |
| 2019/0055248 | A1 | 2/2019 | Gray et al. |
| 2019/0241541 | A1 | 8/2019 | Ciblat et al. |
| 2019/0248778 | A1 | 8/2019 | Gray et al. |
| 2019/0292167 | A1 | 9/2019 | Bradley et al. |
| 2019/0315747 | A9 | 10/2019 | Gray et al. |
| 2020/0017475 | A9 | 1/2020 | Gray et al. |
| 2020/0024271 | A9 | 1/2020 | Gray et al. |
| 2020/0277292 | A1 | 9/2020 | Gray et al. |
| 2020/0297721 | A1 | 9/2020 | Gray et al. |
| 2020/0338074 | A1 | 10/2020 | Hammerman et al. |
| 2021/0115051 | A1 | 4/2021 | Gray et al. |
| 2021/0292299 | A1 | 9/2021 | Gray et al. |
| 2021/0300911 | A1 | 9/2021 | Gray et al. |
| 2021/0317105 | A9 | 10/2021 | Gray et al. |
| 2022/0024929 | A9 | 1/2022 | Gray et al. |
| 2022/0055998 | A1 | 2/2022 | Gray et al. |
| 2022/0089611 | A1 | 3/2022 | Gray et al. |
| 2022/0153730 | A9 | 5/2022 | Gray et al. |
| 2022/0169631 | A9 | 6/2022 | Gray et al. |
| 2022/0213067 | A1 | 7/2022 | Gray et al. |
| 2022/0242865 | A1 | 8/2022 | Gray et al. |
| 2023/0114207 | A1 | 4/2023 | Gray et al. |

FOREIGN PATENT DOCUMENTS

| | | | |
|---|---|---|---|
| CA | 2526430 | A1 | 12/2004 |
| CA | 2550128 | A1 | 6/2005 |
| CA | 2563212 | A1 | 10/2005 |

(56) References Cited

FOREIGN PATENT DOCUMENTS

| | | | |
|---|---|---|---|
| CN | 1701073 | | 11/2005 |
| CN | 1735614 | | 2/2006 |
| CN | 100482665 | | 5/2006 |
| CN | 1784410 | | 6/2006 |
| CN | 107235906 | A | 10/2017 |
| CN | 107686477 | A | 2/2018 |
| EP | 0604181 | A1 | 12/1993 |
| EP | 0618221 | A2 | 3/1994 |
| EP | 0675112 | A1 | 3/1995 |
| EP | 0696593 | A2 | 8/1995 |
| EP | 1847531 | A1 | 10/2007 |
| EP | 1 935 890 | A1 | 6/2008 |
| EP | 2 311 842 | A2 | 4/2011 |
| EP | 3214086 | A1 | 9/2017 |
| EP | 3 273 966 | A2 | 1/2018 |
| GB | 796524 | A | 6/1958 |
| JP | 2003-503351 | A | 1/2003 |
| JP | 2003-503481 | A | 1/2003 |
| JP | 2004-505977 | | 2/2004 |
| JP | 2004-529140 | A | 9/2004 |
| JP | 2005-501860 | A | 1/2005 |
| JP | 2005-505535 | A | 2/2005 |
| JP | 2005-530711 | A | 10/2005 |
| JP | 2005-534635 | A | 11/2005 |
| JP | 2005-538100 | A | 12/2005 |
| JP | 2006-514026 | | 4/2006 |
| JP | 2006-521394 | A | 9/2006 |
| JP | 2006-528163 | A | 12/2006 |
| JP | 2007-500226 | A | 1/2007 |
| JP | 2007-500725 | A | 1/2007 |
| JP | 2007-516201 | A | 6/2007 |
| JP | 2008-500320 | A | 1/2008 |
| JP | 2008-501669 | A | 1/2008 |
| JP | 2008-502610 | A | 1/2008 |
| JP | 2008-528465 | A | 7/2008 |
| JP | 2008-528467 | A | 7/2008 |
| JP | 2009-510110 | A | 3/2009 |
| JP | 2009-520805 | | 5/2009 |
| JP | 2010-505905 | | 2/2010 |
| JP | 2010-511655 | A | 4/2010 |
| JP | 2010-518069 | | 5/2010 |
| JP | 2010-521487 | A | 6/2010 |
| JP | 2010-523643 | | 7/2010 |
| JP | 2010-536869 | A | 12/2010 |
| JP | 2011-515371 | A | 5/2011 |
| JP | 2011-516533 | A | 5/2011 |
| JP | 2011-526594 | A | 10/2011 |
| JP | 2012-511021 | A | 5/2012 |
| JP | 2012-530071 | A | 11/2012 |
| JP | 2014-526549 | A | 10/2014 |
| JP | 2015-503625 | A | 2/2015 |
| JP | 2016-512534 | A | 4/2016 |
| JP | 2016-533379 | A | 10/2016 |
| JP | 2017-504651 | A | 2/2017 |
| JP | 2018-506531 | A | 3/2018 |
| JP | 2018-507877 | A | 3/2018 |
| KR | 10-2009-0053593 | A | 5/2009 |
| MX | 2016-009974 | A | 10/2016 |
| MX | 2016-009975 | A | 10/2016 |
| MX | 2016-009976 | A | 11/2016 |
| WO | WO 84/02131 | A1 | 6/1984 |
| WO | WO 94/19357 | A1 | 9/1994 |
| WO | WO 95/08542 | A1 | 3/1995 |
| WO | WO 95/10514 | A1 | 4/1995 |
| WO | WO 95/10515 | A1 | 4/1995 |
| WO | WO 95/10516 | A1 | 4/1995 |
| WO | WO 95/11917 | A1 | 5/1995 |
| WO | WO 95/12572 | A1 | 5/1995 |
| WO | WO 95/12612 | A1 | 5/1995 |
| WO | WO 95/25086 | A1 | 9/1995 |
| WO | WO 95/26412 | A1 | 10/1995 |
| WO | WO 95/32987 | A1 | 12/1995 |
| WO | WO 95/34535 | A1 | 12/1995 |
| WO | WO 96/00736 | A1 | 1/1996 |
| WO | WO 96/05168 | A1 | 2/1996 |
| WO | WO 96/05169 | A1 | 2/1996 |
| WO | WO 1996/09294 | A1 | 3/1996 |
| WO | WO 96/17861 | A1 | 6/1996 |
| WO | WO 96/21456 | A1 | 7/1996 |
| WO | WO 96/22278 | A1 | 7/1996 |
| WO | WO 96/24611 | A1 | 8/1996 |
| WO | WO 96/30017 | A1 | 10/1996 |
| WO | WO 96/30018 | A1 | 10/1996 |
| WO | WO 96/30343 | A1 | 10/1996 |
| WO | WO 96/30362 | A1 | 10/1996 |
| WO | WO 96/30363 | A1 | 10/1996 |
| WO | WO 96/31111 | A1 | 10/1996 |
| WO | WO 96/31477 | A1 | 10/1996 |
| WO | WO 96/31478 | A1 | 10/1996 |
| WO | WO 96/31501 | A1 | 10/1996 |
| WO | WO 96/33159 | A1 | 10/1996 |
| WO | WO 96/34850 | A1 | 11/1996 |
| WO | WO 96/34851 | A1 | 11/1996 |
| WO | WO 97/00252 | A1 | 1/1997 |
| WO | WO 97/03047 | A1 | 1/1997 |
| WO | WO 97/03050 | A1 | 1/1997 |
| WO | WO 97/04785 | A1 | 2/1997 |
| WO | WO 97/17070 | A1 | 5/1997 |
| WO | WO 97/18813 | A1 | 5/1997 |
| WO | WO 97/21701 | A1 | 6/1997 |
| WO | WO 97/23478 | A1 | 7/1997 |
| WO | WO 97/26246 | A1 | 7/1997 |
| WO | WO 97/30053 | A1 | 8/1997 |
| WO | WO 97/38665 | A2 | 10/1997 |
| WO | WO 97/44350 | A1 | 11/1997 |
| WO | WO 98/02436 | A1 | 1/1998 |
| WO | WO 98/28980 | A1 | 7/1998 |
| WO | WO 98/29119 | A1 | 7/1998 |
| WO | WO 2000/044777 | A1 | 8/2000 |
| WO | WO 2000/050032 | A1 | 8/2000 |
| WO | WO 2000/061186 | A1 | 10/2000 |
| WO | WO 2001/002369 | A2 | 1/2001 |
| WO | WO 2001/019829 | A2 | 3/2001 |
| WO | WO 2001/021596 | A1 | 3/2001 |
| WO | WO 02/12242 | A2 | 2/2002 |
| WO | WO 2002/076986 | A1 | 10/2002 |
| WO | WO 2002/079197 | A1 | 10/2002 |
| WO | WO 2002/080926 | A1 | 10/2002 |
| WO | WO 2002/083653 | A1 | 10/2002 |
| WO | WO 2002/096905 | A1 | 12/2002 |
| WO | WO 2002/102800 | A1 | 12/2002 |
| WO | WO 2003/018021 | A1 | 3/2003 |
| WO | WO 2003/018022 | A1 | 3/2003 |
| WO | WO 2003/026664 | A1 | 4/2003 |
| WO | WO 2003/051847 | A1 | 6/2003 |
| WO | WO 2003/078403 | A2 | 9/2003 |
| WO | WO 2003/097610 | A1 | 11/2003 |
| WO | WO 2004/005283 | A1 | 1/2004 |
| WO | WO 2004/009601 | A1 | 1/2004 |
| WO | WO 2004/010995 | A1 | 2/2004 |
| WO | WO 2004/022561 | A1 | 3/2004 |
| WO | WO 2004/026229 | A2 | 4/2004 |
| WO | WO 2004/039796 | A1 | 5/2004 |
| WO | WO 2004/046118 | A2 | 6/2004 |
| WO | WO 2004/074283 | A1 | 9/2004 |
| WO | WO 2004/076458 | A1 | 9/2004 |
| WO | WO 2004/078757 | A2 | 9/2004 |
| WO | WO 2004/081013 | A1 | 9/2004 |
| WO | WO 2004/087699 | A2 | 10/2004 |
| WO | WO 2004/087707 | A1 | 10/2004 |
| WO | WO 2004/100868 | A2 | 11/2004 |
| WO | WO 2004/113303 | A1 | 12/2004 |
| WO | WO 2004/113304 | A1 | 12/2004 |
| WO | WO 2005/002576 | A2 | 1/2005 |
| WO | WO 2005/011597 | A2 | 2/2005 |
| WO | WO 2005/012256 | A1 | 2/2005 |
| WO | WO 2005/058891 | A1 | 6/2005 |
| WO | WO 2005/070891 | A2 | 8/2005 |
| WO | WO 2005/097790 | A1 | 10/2005 |
| WO | WO 2005/108397 | A1 | 11/2005 |
| WO | WO 2005/116025 | A2 | 12/2005 |
| WO | WO 2006/003276 | A1 | 1/2006 |
| WO | WO 2006/024834 | A1 | 3/2006 |
| WO | WO 2006/031806 | A2 | 3/2006 |

(56) References Cited

FOREIGN PATENT DOCUMENTS

| | | | |
|---|---|---|---|
| WO | WO 2006/034341 | A2 | 3/2006 |
| WO | WO 2006/038001 | A1 | 4/2006 |
| WO | WO 2006/040568 | A1 | 4/2006 |
| WO | WO 2006/072831 | A1 | 7/2006 |
| WO | WO 2006/077414 | A1 | 7/2006 |
| WO | WO 2006/085685 | A1 | 8/2006 |
| WO | WO 2007/002325 | A1 | 1/2007 |
| WO | WO 2007/002433 | A1 | 1/2007 |
| WO | WO 2007/024680 | A1 | 3/2007 |
| WO | WO 2007/035428 | A1 | 3/2007 |
| WO | WO 2007/042786 | A2 | 4/2007 |
| WO | WO 2007/044420 | A1 | 4/2007 |
| WO | WO 2007/048070 | A2 | 4/2007 |
| WO | WO 2007/071963 | A2 | 6/2007 |
| WO | WO 2007/075869 | A2 | 7/2007 |
| WO | WO 2007/129195 | A2 | 11/2007 |
| WO | WO 2007/138277 | A1 | 12/2007 |
| WO | WO 2008/009954 | A1 | 1/2008 |
| WO | WO 2008/049856 | A1 | 5/2008 |
| WO | WO 2008/063888 | A2 | 5/2008 |
| WO | WO 2008/068171 | A1 | 6/2008 |
| WO | WO 2008/074749 | A1 | 6/2008 |
| WO | WO 2008/080015 | A2 | 7/2008 |
| WO | WO 2008/112913 | A1 | 9/2008 |
| WO | WO 2008/124393 | A1 | 10/2008 |
| WO | WO 2008/144253 | A1 | 11/2008 |
| WO | WO 2008/151183 | A1 | 12/2008 |
| WO | WO 2008/151304 | A1 | 12/2008 |
| WO | WO 2008/157575 | A1 | 12/2008 |
| WO | WO 2009/017822 | A2 | 2/2009 |
| WO | WO 2009/028655 | A1 | 3/2009 |
| WO | WO 2009/032694 | A1 | 3/2009 |
| WO | WO 2009/115572 | A2 | 9/2009 |
| WO | WO 2009/145360 | A1 | 12/2009 |
| WO | WO 2009/152027 | A1 | 12/2009 |
| WO | WO 2009/155017 | A2 | 12/2009 |
| WO | WO 2010/008847 | A2 | 1/2010 |
| WO | WO 2010/044885 | A2 | 4/2010 |
| WO | WO 2010/051781 | A1 | 5/2010 |
| WO | WO 2010/065893 | A1 | 6/2010 |
| WO | WO 2010/075542 | A1 | 7/2010 |
| WO | WO 2010/125799 | A1 | 11/2010 |
| WO | WO 2010/144909 | A1 | 12/2010 |
| WO | WO 2011/115725 | A2 | 9/2011 |
| WO | WO 2013/014162 | A1 | 1/2013 |
| WO | WO 2013/040436 | A2 | 3/2013 |
| WO | WO 2013/049279 | A2 | 4/2013 |
| WO | WO 2013/074986 | A1 | 5/2013 |
| WO | WO 2013/154778 | A1 | 10/2013 |
| WO | WO 2014/063061 | A1 | 4/2014 |
| WO | WO 2014/063068 | A1 | 4/2014 |
| WO | WO 2014/165065 | A1 | 10/2014 |
| WO | WO 2015/006754 | A2 | 1/2015 |
| WO | WO 2015/013635 | A2 | 1/2015 |
| WO | WO 2015/058126 | A1 | 4/2015 |
| WO | WO 2015/058140 | A1 | 4/2015 |
| WO | WO 2015/117087 | A1 | 8/2015 |
| WO | WO 2015/154022 | A1 | 10/2015 |
| WO | WO 2015/154038 | A1 | 10/2015 |
| WO | WO 2015/164604 | A1 | 10/2015 |
| WO | WO 2015/164614 | A1 | 10/2015 |
| WO | WO 2016/014542 | A1 | 1/2016 |
| WO | WO 2016/014551 | A1 | 1/2016 |
| WO | WO 2016/058544 | A1 | 4/2016 |
| WO | WO 2016/105528 | A2 | 6/2016 |
| WO | WO 2016/142855 | A2 | 9/2016 |
| WO | WO 2016/160617 | A2 | 10/2016 |
| WO | WO 2016/193939 | A1 | 12/2016 |
| WO | WO 2016/201370 | A1 | 12/2016 |
| WO | WO 2017/037576 | A1 | 3/2017 |
| WO | WO 2017/160717 | A2 | 9/2017 |
| WO | WO 2020/100944 | A1 | 5/2020 |
| WO | WO 2020/140098 | A1 | 7/2020 |
| WO | WO 2021/016388 | A1 | 1/2021 |
| WO | WO 2021/026109 | A1 | 2/2021 |
| WO | WO 2021/133601 | A1 | 7/2021 |

OTHER PUBLICATIONS

International Preliminary Report on Patentability for PCT/US2013/065689, mailed Apr. 30, 2015.
International Search Report and Written Opinion for PCT/US2013/065698, mailed Feb. 20, 2014.
International Preliminary Report on Patentability for PCT/US2013/065698, mailed Apr. 30, 2015.
International Search Report and Written Opinion for PCT/US2014/061232, mailed Dec. 23, 2014.
International Search Report and Written Opinion for PCT/US2015/027312, mailed Jul. 10, 2015.
International Preliminary Report on Patentability for PCT/US2015/027312, mailed Nov. 3, 2016.
International Search Report and Written Opinion for PCT/US2015/027294, mailed Jul. 10, 2015.
Extended European Search Report for EP 10786967.9, mailed Oct. 23, 2012.
International Search Report and Written Opinion for PCT/US2010/038518, mailed Aug. 6, 2010.
International Preliminary Report on Patentability for PCT/US2010/038518, mailed Dec. 22, 2011.
Extended European Search Report for EP 10844280.7, mailed Apr. 17, 2013.
Extended European Search Report for EP 15160591.2, mailed Nov. 2, 2015.
International Search Report and Written Opinion for PCT/US2010/062310, mailed Oct. 4, 2011.
International Preliminary Report on Patentability for PCT/US2010/062310, mailed Jul. 12, 2012.
International Search Report and Written Opinion for PCT/US2015/000297, mailed Mar. 4, 2016.
International Preliminary Report on Patentability PCT/US2015/000297, mailed Jul. 6, 2017.
Partial Supplementary Search Report for EP 16808476.2, mailed on Mar. 7, 2019.
Extended European Search Report for EP 16808476.2, mailed on Jun. 14, 2019.
International Search Report and Written Opinion for PCT/US2016/037086, mailed Sep. 2, 2016.
International Preliminary Report on Patentability for PCT/US/2016/037086, mailed Dec. 21, 2017.
Extended European Search Report for EP 15773870.7, mailed on Oct. 17, 2018.
Invitation to Pay Additional Fees for PCT/US2016/024345, mailed Aug. 9, 2016.
International Search Report and Written Opinion for PCT/US2016/024345, mailed Oct. 6, 2016.
International Preliminary Report on Patentability for PCT/US2016/024345, mailed Oct. 12, 2017.
Extended European Search Report for EP 16845194.6, mailed on Mar. 1, 2019.
Invitation to Pay Additional Fees for PCT/US2016/051118, mailed Dec. 1, 2016.
International Search Report and Written Opinion for PCT/US2016/051118, mailed Mar. 13, 2017.
International Preliminary Report on Patentability for PCT/US2016/051118, mailed Mar. 22, 2018.
Invitation to Pay Additional Fees for PCT/US2011/025423, mailed May 31, 2011.
International Search Report and Written Opinion from PCT/US2011/025423, mailed Nov. 5, 2012.
International Preliminary Report on Patentability for PCT/US2011/025423, mailed Nov. 29, 2012.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.

(56) References Cited

OTHER PUBLICATIONS

Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bogoyevitch et al., c-Jun N-terminal kinase (JNK) signaling: recent advances and challenges. Biochim Biophys Acta. Mar. 2010; 1804(3):463-75. doi: 10.1016/j.bbapap.2009.11.002. Epub Nov. 10, 2009.
Bosken et al., The structure and substrate specificity of human Cdk12/Cyclin K. Nat Commun. Mar. 24, 2014;5:3505. doi: 10.1038/ncomms4505.
Brasca et al., 6-Substituted pyrrolo[3,4-c]pyrazoles: an improved class of CDK2 inhibitors. ChemMedChem. Jun. 2007;2(6):841-52.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chene, Challenges in design of biochemical assays for the identification of small molecules to target multiple conformations of protein kinases. Drug Discov Today. Jun. 2008;13(11-12):522-9. doi: 10.1016/j.drudis.2008.03.023. Epub May 5, 2008.
Chiarugi et al., Cox-2, iNOS and p53 as play-makers of tumor angiogenesis. International Journal of Molecular Medicine 1998;2:715-9.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Database Registry [Online] Retrieved from STN, 2011年 12月4日,search date :Oct. 7, 2019; RN 1350102-23-6, 1349782-05-3, 1349471-31-3, 1349357-86-3, 1349106-33-7, 1348397-56-7, 1348192-23-3, 1348088-42-5.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Dent et al. Synergistic combinations of signaling pathway inhibitors: mechanisms for improved cancer therapy. Drug Resist Updat. Jun. 2009;12(3):65-73. doi: 10.1016/j.drup.2009.03.001.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fan et al., Dual leucine zipper-bearing kinase (DLK) activates p46SAPK and p38mapk but not ERK2. J Biol Chem. Oct. 4, 1996;271(40):24788-93.

(56) References Cited

OTHER PUBLICATIONS

Fancelli et al., Potent and selective Aurora inhibitors identified by the expansion of a novel scaffold for protein kinase inhibition. J Med Chem. Apr. 21, 2005;48(8):3080-4.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
GenBank Accession No. M80629. Lapidot-Lifson et al., Dec. 31, 1994. 2 pages.
GenBank Accession No. NP_001790. Yang et al., Oct. 6, 2016. 4 pages.
Girotti et al., No. longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kooistra et al., Kinase-Centric Computational Drug Development, In 50 Annual Reports in Medicinal Chemistry. 2017;197-236.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.

(56) References Cited

OTHER PUBLICATIONS

Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Patani et al., Bioisosterism: a Rational Approach in Drug Design. Chem Rev. 1996;96:3147-3176.
Patel et al., Discovery of dual leucine zipper kinase (DLK, MAP3K12) inhibitors with activity in neurodegeneration models. J Med Chem. Jan. 8, 2015;58(1):401-18. doi: 10.1021/jm5013984. Epub Oct. 23, 2014.
Peifer et al., Small-molecule inhibitors of PDK1. ChemMedChem. Dec. 2008;3(12):1810-38. doi: 10.1002/cmdc.200800195.
Pevarello et al., 3-Amino-1,4,5,6-tetrahydropyrrolo[3,4-c]pyrazoles: a new class of CDK2 inhibitors. Bioorg Med Chem Lett. Feb. 15, 2006;16(4):1084-90.
Powell et al., Regulation of immune responses by mTOR. Annu Rev Immunol. 2012;30:39-68. doi: 10.1146/annurev-immunol-020711-075024. Epub Nov. 29, 2011.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
PubChem-CID-68365059. Available at https://pubchem.ncbi.nlm.nih.gov/compound/68365059. Accessed Jun. 17, 2016.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Sánchez-Martínez et al., Cyclin dependent kinase (CDK) inhibitors as anticancer drugs. Bioorg Med Chem Lett. Sep. 1, 2015;25(17):3420-35. doi: 10.1016/j.bmcl.2015.05.100. Epub Jun. 6, 2015.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Sidow et al., Concepts in solid tumor evolution. Trends Genet. Apr. 2015;31(4):208-14. doi: 10.1016/j.tig.2015.02.001. Epub Feb. 27, 2015. Author manuscript.
Smith et al., Recent advances in the research and development of RAF kinase inhibitors. Curr. Top Med. Chem. 2006; 6(11):1071-89.

(56) References Cited

OTHER PUBLICATIONS

Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Takemori et al., Inactivation of HDAC5 by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Uniprot No. Q9NYV4. Last modified Mar. 15, 2017. 14 pages.
Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.
Wang et al., IRAK-4 inhibitors for inflammation. Curr Top Med Chem. 2009;9(8):724-37.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Wietek et al., IRAK-4: a new drug target in inflammation, sepsis, and autoimmunity. Mol Interv. Jul. 2002;2(4):212-5.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Wu et al., FDA-approved small-molecule kinase inhibitors. Trends Pharmacol Sci. Jul. 2015;36(7):422-39. doi: 10.1016/j.tips.2015.04.005. Epub May 12, 2015.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Yasuda et al., The stem cell factor/c-kit receptor pathway enhances proliferation and invasion of pancreatic cancer cells. Mol Cancer. Oct. 18, 2006;5:46.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zebisch et al., Back to the roots: the remarkable RAF oncogene story Cell Mol Life Sci. Jun. 2006;63(11):1314-30.
Zeng et al. Targeting MYC dependency in ovarian cancer through inhibition of CDK7 and CDK12/13. Elife. 2018;7:e39030. Published Nov. 13, 2018. doi:10.7554/eLife.39030.
Zhang et al. CDK7 Inhibition Potentiates Genome Instability Triggering Anti-tumor Immunity in Small Cell Lung Cancer. Cancer Cell. 2020;37(1):37-54.e9. doi:10.1016/j.ccell.2019.11.003.
Zhang et al., Discovery of potent and selective covalent inhibitors of JNK. Chem Biol. Jan. 27, 2012;19(1):140-54. doi: 10.1016/j.chembiol.2011.11.010.
Zhang et al., Etk/Bmx transactivates vascular endothelial growth factor 2 and recruits phosphatidylinositol 3-kinase to mediate the tumor necrosis factor-induced angiogenic pathway. J Biol Chem. Dec. 19, 2003;278(51):51267-76. Epub Oct. 7, 2003.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. J National Cancer Institute 1982;69(2):475.
Zompi et al., Animal models of dengue virus infection. Viruses. Jan. 2012;4(1):62-82. doi: 10.3390/v4010062. Epub Jan. 9, 2012.
Extended European Search Report for EP 16815397.1, mailed on Nov. 22, 2018.
International Search Report and Written Opinion for PCT/US16/39302, mailed Sep. 27, 2016.
International Preliminary Report on Patentability for PCT/US2016/39302, mailed Jan. 4, 2018.
Extended European Search Report for EP 21193645.5, mailed on May 11, 2022.
Extended European Search Report for EP 19826764.3 mailed on May 23, 2022.
Invitation to Pay Additional Fees for PCT/US2019/038677, mailed Aug. 13, 2019.
International Search Report and Written Opinion for PCT/US2019/038677, mailed Oct. 2, 2019.
International Preliminary Report on Patentability PCT/US2019/038677, mailed Jan. 7, 2021.
Extended European Search Report for EP 19894946.3 mailed on Jul. 20, 2022.
International Preliminary Report on Patentability for PCT/US2019/066201, mailed Jun. 24, 2021.
Extended European Search Report for EP 19903185.7 mailed on Aug. 5, 2022.
Extended European Search Report for EP 20908219.7 mailed on Dec. 12, 2023.
International Search Report and Written Opinion for PCT/US2020/065267, mailed Mar. 26, 2021.
International Preliminary Report on Patentability for PCT/US2020/065267, mailed Jul. 7, 2022.
[No Author Listed], CAS Registry No. 1347879-84-8. Entered STN: Dec. 4, 2011. 1 page.
[No Author Listed], CAS Registry No. 1349030-04-1. Entered STN: Dec. 5, 2011. 1 page.
Aguirre et al., Phosphorylation of Ser307 in insulin receptor substrate-1 blocks interactions with the insulin receptor and inhibits insulin action. J Biol Chem. Jan. 11, 2002;277(2):1531-7. doi: 10.1074/jbc.M101521200. Epub Oct. 17, 2001. PMID: 11606564.
Aguirre et al., The c-Jun NH(2)-terminal kinase promotes insulin resistance during association with insulin receptor substrate-1 and phosphorylation of Ser(307). J Biol Chem. Mar. 24, 2000;275(12):9047-54. doi: 10.1074/jbc.275.12.9047. PMID: 10722755.
Alam et al., Synthesis and SAR of aminopyrimidines as novel c-Jun N-terminal kinase (JNK) inhibitors. Bioorg Med Chem Lett. Jun. 15, 2007;17(12):3463-7. doi: 10.1016/j.bmcl.2007.03.078. Epub Mar. 30, 2007. PMID: 17459703.
Barf et al., Irreversible protein kinase inhibitors: balancing the benefits and risks. J Med Chem. Jul. 26, 2012;55(14):6243-62. doi: 10.1021/jm3003203. Epub Jun. 8, 2012.
Blease et al., Emerging treatments for asthma. Expert Opin Emerg Drugs. May 2003;8(1):71-81.doi: 10.1517/14728214.8.1.71.
Brasca et al., Optimization of 6,6-dimethyl pyrrolo[3,4-c]pyrazoles: Identification of PHA-793887, a potent CDK inhibitor suitable for

(56) References Cited

OTHER PUBLICATIONS intravenous dosing. Bioorg Med Chem. Mar. 1, 2010;18(5):1844-53. doi: 10.1016/j.bmc.2010.01.042. Epub Jan. 25, 2010. PMID: 20153204.
Carmi et al., Novel irreversible epidermal growth factor receptor inhibitors by chemical modulation of the cysteine-trap portion. J Med Chem. Mar. 11, 2010;53(5):2038-50. doi: 10.1021/jm901558p.
CAS Registry No. 1025964-63-9 Entered STN: Jun. 6, 2008.
CAS Registry No. 1026531-51-0 Entered STN: Jun. 8, 2008.
CAS Registry No. 1026878-26-1 Entered STN: Jun. 10, 2008.
CAS Registry No. 1026975-11-0 Entered STN: Jun. 10, 2008.
CAS Registry No. 1027155-85-6 Entered STN: Jun. 11, 2008.
CAS Registry No. 1028288-20-1 Entered STN: Jun. 15, 2008.
CAS Registry No. 1347533-63-4 Entered STN: Dec. 2, 2011.
CAS Registry No. 1347548-09-7 Entered STN: Dec. 2, 2011.
CAS Registry No. 1609787-73-6 Entered STN: Jun. 6, 2014.
CAS Registry No. 1702381-29-0 Entered STN: May 13, 2015.
CAS Registry No. 1702381-42-7 Entered STN: May 13, 2015.
CAS Registry No. 1702381-64-3 Entered STN: May 13, 2015.
CAS Registry No. 1702381-71-2 Entered STN: May 13, 2015.
CAS Registry No. 1702381-78-9 Entered STN: May 13, 2015.
CAS Registry No. 1702809-46-8 Entered STN: May 13, 2015.
CAS Registry No. 1703051-55-1 Entered STN: May 13, 2015.
CAS Registry No. 1703051-60-8 Entered STN: May 13, 2015.
CAS Registry No. 1703051-61-9 Entered STN: May 13, 2015.
CAS Registry No. 1703051-63-1 Entered STN: May 13, 2015.
CAS Registry No. 1998741-41-5 Entered STN: Sep. 23, 2016.
CAS Registry No. 1998741-43-7 Entered STN: Sep. 23, 2016.
CAS Registry No. 956025-12-0 Entered STN: Nov. 27, 2007.
Chang et al., Mammalian MAP kinase signalling cascades. Nature. Mar. 1, 2001;410(6824):37-40. doi: 10.1038/35065000. PMID: 11242034.
Chialda et al., Inhibitors of mitogen-activated protein kinases differentially regulate costimulated T cell cytokine production and mouse airway eosinophilia. Respir Res. Apr. 15, 2005;6(1):36. doi: 10.1186/1465-9921-6-36. PMID: 15833106.
Choong et al., A diaminocyclohexyl analog of SNS-032 with improved permeability and bioavailability properties. Bioorg Med Chem Lett. Nov. 1, 2008;18(21):5763-5. doi: 10.1016/j.bmcl.2008.09.073. Epub Sep. 24, 2008. PMID: 18842409.
Dérijard et al., JNK1: a protein kinase stimulated by UV light and Ha-Ras that binds and phosphorylates the c-Jun activation domain. Cell. Mar. 25, 1994;76(6):1025-37. doi: 10.1016/0092-8674(94)90380-8. PMID: 8137421.
Devegowda et al., Novel 6-N-arylcarboxamidopyrazolo[4,3-d]pyrimidin-7-one derivatives as potential anti-cancer agents. Bioorg Med Chem Lett. Mar. 1, 2010;20(5):1630-3. doi: 10.1016/j.bmcl.2010.01.029. Epub Jan. 20, 2010.
Dorée et al., The cyclin-dependent protein kinases and the control of cell division. FASEB J. Nov. 1994;8(14):1114-21. doi: 10.1096/fasebj.8.14.7958616.
Ferguson et al., Synthesis and structure activity relationships of a series of 4-amino-1H-pyrazoles as covalent inhibitors of CDK14. Bioorg Med Chem Lett. Aug. 1, 2019;29(15):1985-1993. doi: 10.1016/j.bmcl.2019.05.024. Epub May 23, 2019.
Gu et al., Upregulated PFTK1 promotes tumor cell proliferation, migration, and invasion in breast cancer. Med Oncol. Jul. 2015;32(7):195. doi: 10.1007/s12032-015-0641-8. Epub Jun. 2, 2015.
Han et al., Joint damage and inflammation in c-Jun N-terminal kinase 2 knockout mice with passive murine collagen-induced arthritis. Arthritis Rheum. Mar. 2002;46(3):818-23. doi: 10.1002/art.10104. PMID: 11920420.
Hazlitt et al., Development of Second-Generation CDK2 Inhibitors for the Prevention of Cisplatin-Induced Hearing Loss. J Med Chem. Sep. 13, 2018;61(17):7700-7709. doi: 10.1021/acs.jmedchem.8b00669. Epub Aug. 24, 2018. PMID: 30091915; PMCID: PMC6443376.
Hellvard et al., Inhibition of CDK9 as a therapeutic strategy for inflammatory arthritis. Sci Rep. Aug. 11, 2016;6:31441. doi: 10.1038/srep31441.
Hirosumi et al., A central role for JNK in obesity and insulin resistance. Nature. Nov. 21, 2002;420(6913):333-6. doi: 10.1038/nature01137.
Hunot et al., JNK-mediated induction of cyclooxygenase 2 is required for neurodegeneration in a mouse model of Parkinson's disease. Proc Natl Acad Sci USA. Jan. 13, 2004;101(2):665-70. doi: 10.1073/pnas.0307453101. Epub Jan. 2, 2004. PMID: 14704277.
Johnson et al., Mitogen-activated protein kinase pathways mediated by ERK, JNK, and p38 protein kinases. Science. Dec. 6, 2002;298(5600):1911-2. doi: 10.1126/science. 1072682. PMID: 12471242.
Kallunki T et al., JNK2 contains a specificity-determining region responsible for efficient c-Jun binding and phosphorylation. Genes Dev. Dec. 15, 1994;8(24):2996-3007. doi: 10.1101/gad.8.24.2996. PMID: 8001819.
Kyriakis et al., Mammalian mitogen-activated protein kinase signal transduction pathways activated by stress and inflammation. Physiol Rev. Apr. 2001;81(2):807-69. doi: 10.1152/physrev.2001.81.2.807. PMID: 11274345.
Leung et al., A novel interplay between oncogenic PFTK1 protein kinase and tumor suppressor TAGLN2 in the control of liver cancer cell motility. Oncogene. Nov. 3, 2011;30(44):4464-75. doi: 10.1038/onc.2011.161. Epub May 16, 2011.
Liu et al., Cyclin Y regulates the proliferation, migration, and invasion of ovarian cancer cells via Wnt signaling pathway. Tumour Biol. Aug. 2016;37(8):10161-75. doi: 10.1007/s13277-016-4818-3. Epub Jan. 29, 2016.
Malumbres et al., CDK inhibitors in cancer therapy: what is next? Trends Pharmacol Sci. Jan. 2008;29(1):16-21. doi: 10.1016/j.tips.2007.10.012. Epub Dec. 4, 2007.
Mikhail et al., Cyclin-dependent kinase inhibitors and the treatment of gastrointestinal cancers. Am J Pathol. May 2015;185(5):1185-97. doi: 10.1016/j.ajpath.2015.01.008. Epub Mar. 5, 2015.
Mohit et al., p493F12 kinase: a novel MAP kinase expressed in a subset of neurons in the human nervous system. Neuron. Jan. 1995;14(1):67-78. doi: 10.1016/0896-6273(95)90241-4. PMID: 7826642.
Olson et al. Development of a Selective CDK7 Covalent Inhibitor Reveals Predominant Cell-Cycle Phenotype. Cell Chem Biol. Jun. 20, 2019;26(6):792-803.e10. doi: 10.1016/j.chembiol.2019.02.012. Epub Mar. 21, 2019. PMID: 30905681.
Osto et al., c-Jun N-terminal kinase 2 deficiency protects against hypercholesterolemia-induced endothelial dysfunction and oxidative stress. Circulation. Nov. 11, 2008;118(20):2073-80. doi: 10.1161/CIRCULATIONAHA.108.765032. Epub Oct. 27, 2008. PMID: 18955669.
Ou-Yang et al., Cyclin-Dependent Kinase 14 Promotes Cell Proliferation, Migration and Invasion in Ovarian Cancer by Inhibiting Wnt Signaling Pathway. Gynecol Obstet Invest. 2017;82(3):230-239. doi: 10.1159/000447632. Epub Aug. 10, 2016.
Pang et al., Identification of PFTAIRE protein kinase 1, a novel cell division cycle-2 related gene, in the motile phenotype of hepatocellular carcinoma cells. Hepatology. Aug. 2007;46(2):436-45. doi: 10.1002/hep.21691.
Patricelli et al., Functional interrogation of the kinome using nucleotide acyl phosphates. Biochemistry. Jan. 16, 2007;46(2):350-8. doi: 10.1021/bi062142x.
Pearson et al., Mitogen-activated protein (MAP) kinase pathways: regulation and physiological functions. Endocr Rev. Apr. 2001;22(2):153-83. doi: 10.1210/edrv.22.2.0428. PMID: 11294822.
Pelaia et al., Mitogen-activated protein kinases and asthma. J Cell Physiol. Mar. 2005;202(3):642-53. doi: 10.1002/jcp.20169. PMID: 15316926.
Pulverer et al., Phosphorylation of c-jun mediated by MAP kinases. Nature. Oct. 17, 1991;353(6345):670-4. doi: 10.1038/353670a0. PMID: 1922387.
Raman et al., Differential regulation and properties of MAPKs. Oncogene. May 14, 2007;26(22):3100-12. doi: 10.1038/sj.onc.1210392. PMID: 17496909.

(56) References Cited

OTHER PUBLICATIONS

Sabio et al., cJun NH2-terminal kinase 1 (JNK1): roles in metabolic regulation of insulin resistance. Trends Biochem Sci. Sep. 2010;35(9):490-6. doi: 10.1016/j.tibs.2010.04.004. Epub May 7, 2010. PMID: 20452774.
Sluss et al., Signal transduction by tumor necrosis factor mediated by JNK protein kinases. Mol Cell Biol. Dec. 1994;14(12):8376-84. doi: 10.1128/mcb.14.12.8376-8384.1994. PMID: 7969172.
Sun et al., PFTK1 interacts with cyclin Y to activate non-canonical Wnt signaling in hepatocellular carcinoma. Biochem Biophys Res Commun. Jun. 20, 2014;449(1):163-8. doi: 10.1016/j.bbrc.2014.05.002. Epub May 10, 2014.
Taneera et al., Expression profiling of cell cycle genes in human pancreatic islets with and without type 2 diabetes. Mol Cell Endocrinol. Aug. 15, 2013;375(1-2):35-42. doi: 10.1016/j.mce.2013.05.003. Epub May 22, 2013.
Urich et al., The design and synthesis of potent and selective inhibitors of Trypanosoma brucei glycogen synthase kinase 3 for the treatment of human african trypanosomiasis. J Med Chem. Sep. 25, 2014;57(18):7536-49. doi: 10.1021/jm500239b. Epub Sep. 8, 2014. Supplemental information included. 18 total pages.
Wong WS. Inhibitors of the tyrosine kinase signaling cascade for asthma. Curr Opin Pharmacol. Jun. 2005;5(3):264-71. doi: 10.1016/j.coph.2005.01.009. PMID: 15907913.
Zhang et al., Agents targeting c-Jun N-terminal kinase pathway as potential neuroprotectants. Expert Opin Investig Drugs. Nov. 2005;14(11):1373-83. doi: 10.1517/13543784.14.11.1373. PMID: 16255677.
Zhang et al., PFTK1 regulates cell proliferation, migration and invasion in epithelial ovarian cancer. Int J Biol Macromol. Apr. 2016;85:405-16. doi: 10.1016/j.ijbiomac.2016.01.009. Epub Jan. 6, 2016.

* cited by examiner

PYRAZOLOPYRIDINE INHIBITORS OF C-JUN-N-TERMINAL KINASES AND USES THEREOF

RELATED APPLICATIONS

The present application is a national stage filing under 35 U.S.C. § 371 of International PCT Application PCT/US2019/066201, filed Dec. 13, 2019, which claims priority under 35 U.S.C. § 119(e) to U.S. provisional application, U.S. Ser. No. 62/780,066, filed Dec. 14, 2018, each of which is incorporated herein by reference.

BACKGROUND OF THE INVENTION

In mammalian cells, the MAPK (Mitogen-Activated Protein Kinase) In mammalian cells, the MAPK (Mitogen-Activated Protein Kinase) signaling system is comprised of, at least, four distinct signaling modules defined by a core of MAP4K, MAP3K, MAP2K, and MAPKs that are named after the "terminal" MAPK kinase in each pathway: ERK1, ERK2, JNK1, JNK2, JNK3, p38alpha/beta, and ERK5 (Chang et al., 2001; Johnson et al., 2002; Pearson et al., 2001; and Raman et al., 2007). JNKs (c-Jun N-terminal kinases) become highly activated after cells are exposed to stress conditions such as cytokines, osmotic stress, hypoxia, and UV light, and are poorly activated by exposure to growth factors or mitogens (Derijard et al., 1994; and Pulverer et al., 1991). There are three distinct genes JNK1, JNK2, and JNK3 that are alternatively spliced to yield approximately ten different proteins with the predominant isoforms: JNK1 and JNK2 expressed ubiquitously, and JNK3 expressed primarily in the nervous system (Derijard et al., 1994; Kallunki et al., 1994; Sluss et al., 1994; and Mohit et al., 1995). JNKs are activated by phosphorylation at the activation T-loop residues Thr183/Tyr185 by the MAP2Ks: MKK4 and MKK7, and are deactivated by MAP kinase phosphatases including MKP1 and MKP5. Signaling through the JNK-pathway is organized through binding to "scaffolding" proteins such as JIP which assemble signaling complexes containing MAP3K, MAP2K, and MAPKs in addition to transcription factors such as c-Jun, ATF2, and Elk1 which are phosphorylated by JNK. As JNKs comprise a central node in the inflammatory signaling network, it is not surprising that hyperactivation of JNK signaling is a very common finding in a number of disease states, including cell proliferative disease (e.g., cancer), inflammatory diseases, autoimmune diseases, cardiovascular diseases, and neurodegenerative diseases. A significant body of genetic and pharmacological evidence has been generated that suggest that inhibitors of JNK signaling may provide a promising therapeutic strategy. JNK3 knockout mice exhibit amelioration of neurodegeneration in animal models of Parkinson's and Alzheimer's disease (Kyriakis et al., 2001; Zhang et al., 2005; and Hunot et al., 2004). JNK1 phosphorylates IRS-1, a key molecule in the insulin-sensing pathway which down-regulates insulin signaling, and JNK1 knockout mice are resistant to diet-induced obesity (Aguirre et al., 2000 and 2002; Hirosumi et al., 2002; and Sabio et al., 2010). JNK2, often in concert with JNK1, has been implicated in the pathology of autoimmune disorders, such as rheumatoid arthritis (Han et al., 2002) and asthma (Wong, W. S., 2005; Pelaia et al., 2005; Blease et al., 2003; Chialda et al., 2005); and a recent study suggests that JNK2 may play a role in cardiovascular disease and atherosclerosis as well (Osto et al., 2008).

The ability to gain selectivity among highly homologous kinases with similarly placed cysteine residues would set an important precedent for the large number of other kinases where a similar problem exists, and there is a need for new compounds that inhibit JNK signaling, particularly ones that selectively inhibit JNK2. Thus, the present invention is directed toward covalent inhibitors of JNK2 that target Cys116, a residue conserved in JNK1 and JNK3, based upon the compounds' ability to recognize conformations that are unique to JNK2.

SUMMARY OF THE INVENTION

The present invention provides compounds of Formula (I), and pharmaceutically acceptable salts, solvates, hydrates, polymorphs, co-crystals, tautomers, stereoisomers, isotopologues, prodrugs, and compositions thereof. The present invention further provides methods of using the inventive compounds, and pharmaceutically acceptable salts, solvates, hydrates, polymorphs, co-crystals, tautomers, stereoisomers, isotopologues, prodrugs, and compositions thereof, to study the inhibition of JNK and JNK signaling, as well as therapeutics for the prevention and treatment of diseases associated with JNK activity. In certain embodiments, the inventive compounds are used for the prevention and treatment of proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell.

In one aspect, the present disclosure provides compounds of Formula (I):

(I)

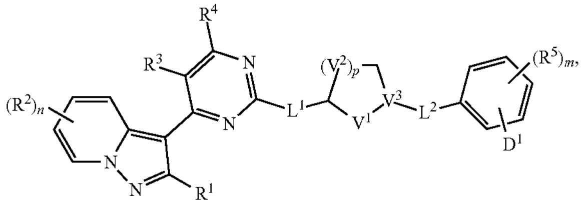

and pharmaceutically acceptable salts, solvates, hydrates, polymorphs, co-crystals, tautomers, stereoisomers, isotopologues, and prodrugs thereof, wherein:

$R^1$ is optionally substituted aryl or optionally substituted heteroaryl;

$R^2$, $R^3$, $R^4$, and $R^5$ are each independently hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $—NO_2$, —CN, —SCN, $—OR^{D1}$, $—N(R^{D1a})_2$, or $—SR^{D1}$, wherein $R^{D1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom;

n is 1, 2, or 3;

m is 1, 2, 3, or 4;

$L^1$ is O, S, or —N($R^a$)—, wherein $R^a$ is hydrogen, optionally substituted acyl, optionally substituted $C_{1-6}$ alkyl, or a nitrogen protecting group;

$L^2$ is O, S, —$NR^{L2a}$—, —C═O—, —$NR^{L2a}$C(═O)—, or —C(═O)$NR^{L2a}$—, wherein $R^{L2a}$ is hydrogen, optionally substituted acyl, optionally substituted $C_{1-6}$ alkyl, or a nitrogen protecting group;

$V^1$ is C($R^{1a}$)H;

$V^2$ is C($R^{1b}$)H;

$V^3$ is N or C($R^{1c}$);

$R^{1a}$ and $R^{1b}$ are independently hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{C1}$, —N($R^{C1}$)$_2$, or —$SR^{C1}$, wherein $R^{C1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or $R^{1a}$ and $R^{1b}$ are joined together to form an optionally substituted bridged ring;

$R^{1c}$ is hydrogen, or substituted or unsubstituted $C_{1-6}$ alkyl;

p is 1, 2, or 3;

$D^1$ is a warhead of any one of Formulae (i-1) to (i-42):

(i-1)

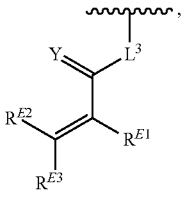

(i-2)

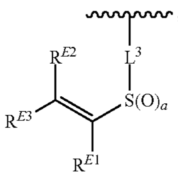

(i-3)

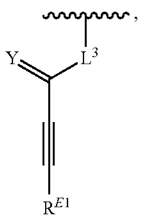

-continued (i-4)

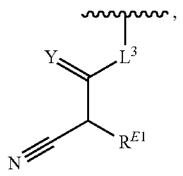

(i-5)

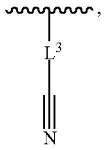

(i-6)

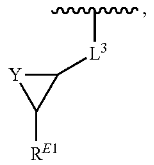

(i-7)

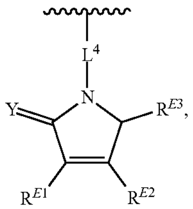

(i-8)

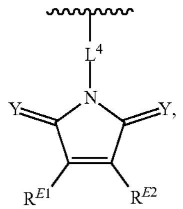

(i-9)

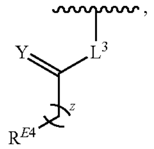

(i-10)

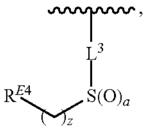

(i-11)

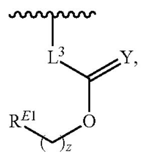

(i-12)

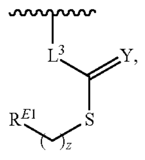

-continued
(i-13)
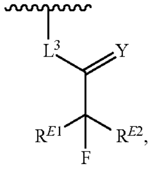
(i-14)
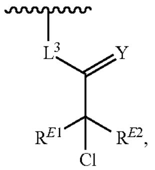
(i-15)
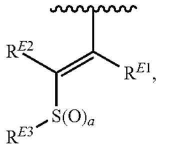
(i-16)
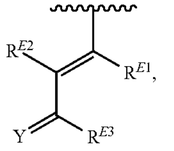
(i-17)
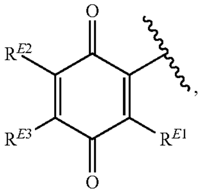
(i-18)
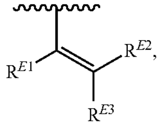
(i-19)
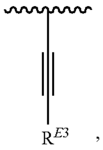
, and
(i-20)
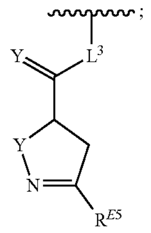
(i-21)
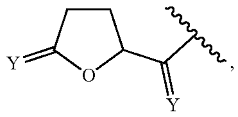
-continued
(i-22)
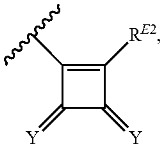
(i-23)
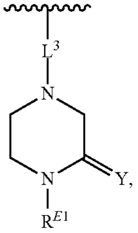
(i-24)
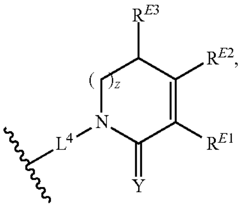
(i-25)
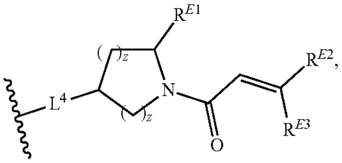
(i-26)
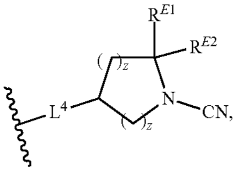
(i-27)
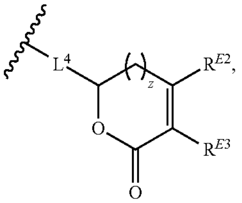
(i-28)
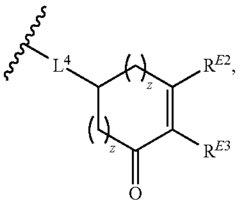
(i-29)
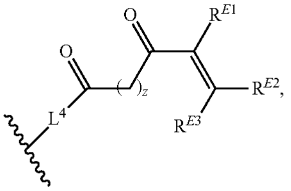

-continued (i-30)

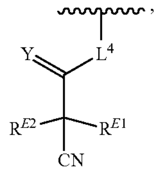

(i-31)

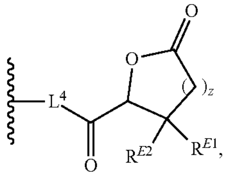

(i-32)

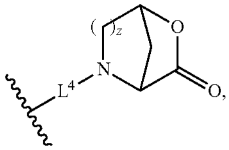

(i-33)

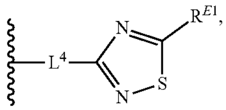

(i-34)

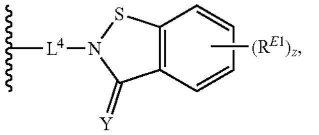

(i-35)

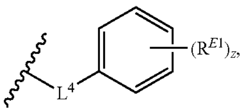

(i-36)

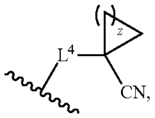

(i-37)

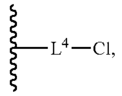

(i-38)

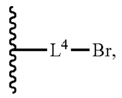

(i-39)

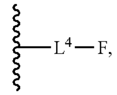

(i-40)

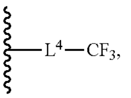

-continued (i-41)

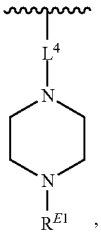

, or (i-42)

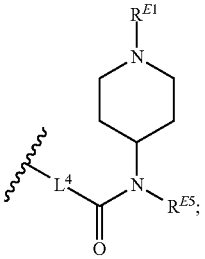

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}C(=O)$—, —$C(=O)NR^{L3a}$—, —SC(=O)—, —C(=O)S—, —OC(=O)—, —C(=O)O—, —$NR^{L3a}C(=S)$—, —$C(=S)NR^{L3a}$—, trans-$CR^{L3b}=CR^{L3b}$—, cis-$CR^{L3b}=CR^{L3b}$—, —C≡C—, —S(=O)—, —S(=O)O—, —OS(=O)—, —$S(=O)NR^{L3a}$, —$NR^{L3a}S(=O)$—, —$S(=O)_2$—, —$S(=O)_2O$—, —$OS(=O)_2$—, —$S(=O)_2NR^{L3a}$—, or —$NR^{L3a}S(=O)_2$—, wherein $R^{L3a}$ is hydrogen, substituted or unsubstituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, and —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, and —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E3a}$, —$CH_2N(R^{E3a})_2$, —$CH_2SR^{E3a}$, —$OR^{E3a}$, —$N(R^{E3a})_2$, and —$SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or $NR^{E6}$, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

Exemplary compounds of Formula (I) include, but are not limited to:

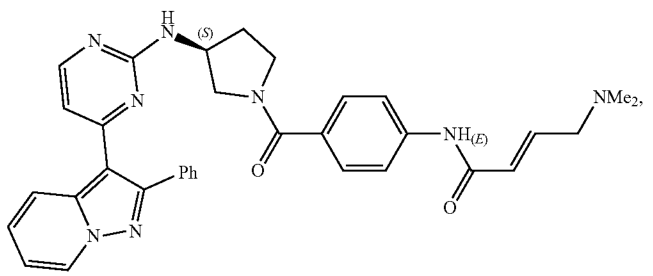

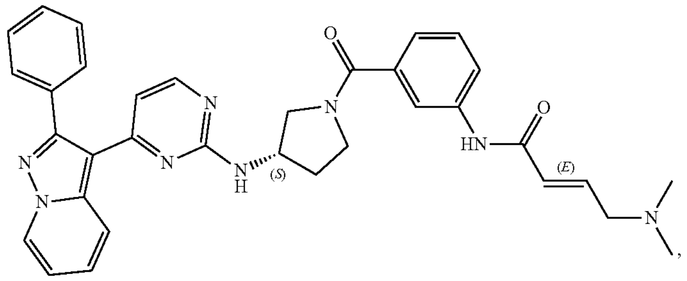

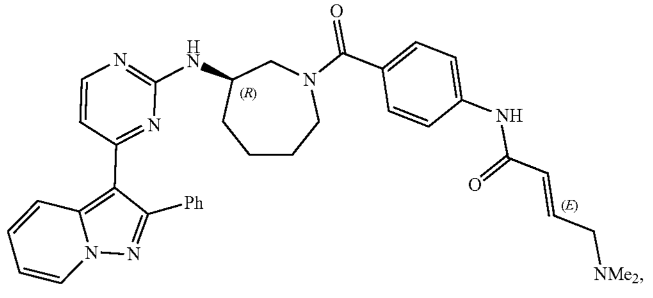

-continued

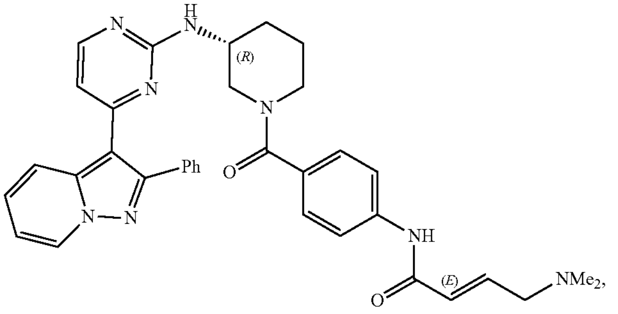

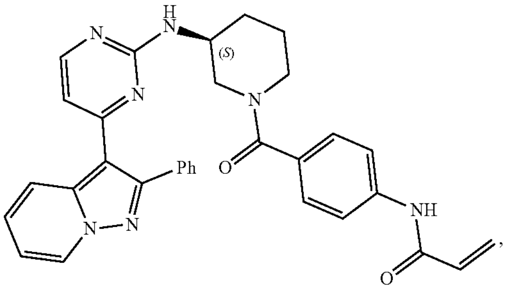

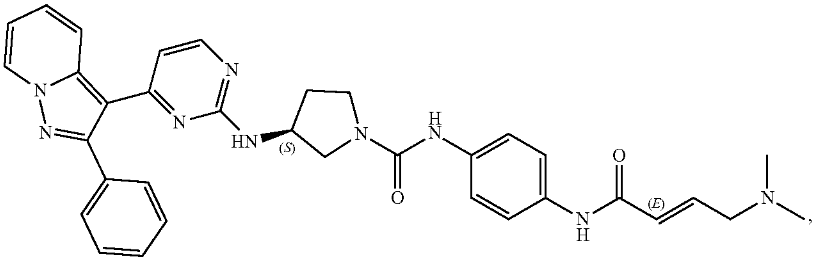

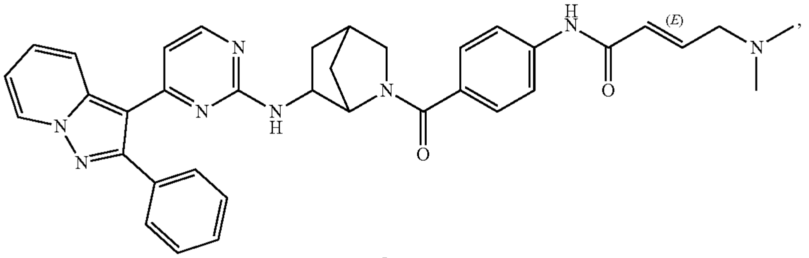

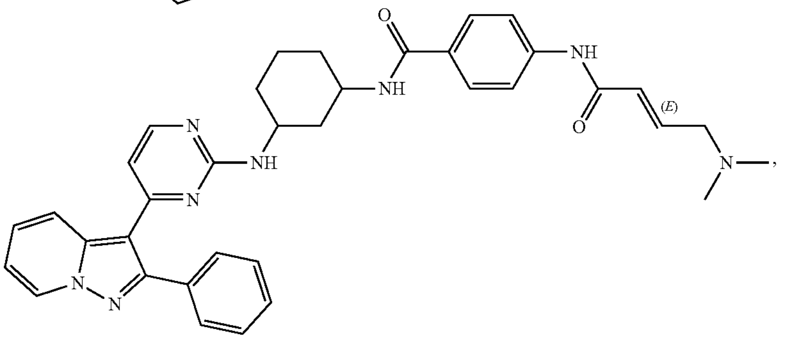

and pharmaceutically acceptable salts, solvates, hydrates, polymorphs, co-crystals, tautomers, stereoisomers, isotopologues, and prodrugs thereof.

In another aspect, the invention provides methods and compositions for the treatment of diseases in a subject, biological sample, tissue, or cell. The diseases being treated by the inventive methods include JNK-associated diseases. Exemplary diseases include, but are not limited to, proliferative diseases (e.g., cancer and benign neoplasms), inflammatory diseases, autoimmune diseases (e.g., rheumatoid arthritis), and cardiovascular diseases (e.g., atherosclerosis). The methods of the invention include administering to a subject in need of treatment of a disease a therapeutically effective amount of a compound of Formula (I). The compound of Formula (I) may be, e.g., I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, or I-30, or a pharmaceutically acceptable salt, solvate, hydrate, polymorph, co-crystal, tautomer, stereoisomer, isotopologues, or prodrug thereof.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease (e.g., proliferative diseases (e.g., cancer and benign neoplasms), inflammatory diseases (e.g., rheumatoid arthritis), autoimmune diseases, and cardiovascular diseases (e.g., atherosclerosis)) in a subject in need thereof. The pharmaceutical composition may be useful for inhibiting the activity of JNK (e.g., JNK2) in a subject, biological sample, tissue, or cell.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a disease (e.g., proliferative diseases (e.g., cancer and benign neoplasms), inflammatory diseases (e.g., rheumatoid arthritis), autoimmune diseases, and cardiovascular diseases (e.g., atherosclerosis)) in a subject in need thereof, or inhibiting the activity of a JNK (e.g., JNK2) in a biological sample, tissue, or cell.

In another aspect, described herein are methods for treating and/or preventing a disease (e.g., proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell. Exemplary proliferative diseases which may be treated include diseases associated with the overexpression or increased activity of a JNK (e.g., cancer or benign neoplasms).

Another aspect relates to methods of inhibiting the activity of a kinase (e.g., JNK (e.g., JNK2)) using a compound described herein in a biological sample (e.g., cell, or tissue).

In another aspect, described herein are methods of inhibiting the activity of a kinase (e.g., a JNK (e.g., JNK2)) using a compound described herein in a subject. Another aspect relates to methods of selectively inhibiting the activity of a kinase (e.g., JNK (e.g., JNK2)) using a compound described herein in a biological sample (e.g., cell, or tissue). In another aspect, described herein are methods of selectively inhibiting the activity of a kinase (e.g., a JNK (e.g., JNK2)) using a compound described herein in a subject.

In another aspect, the present disclosure provides compounds of Formula (I), and pharmaceutically acceptable salts, solvates, hydrates, polymorphs, co-crystals, tautomers, stereoisomers, isotopologues, prodrugs, and compositions thereof, for use in the treatment of a disease (e.g., proliferative diseases (e.g., cancer and benign neoplasms), inflammatory diseases (e.g., rheumatoid arthritis), autoimmune diseases, and cardiovascular diseases (e.g., atherosclerosis)) in a subject.

In another aspect, the present disclosure provides compounds of Formula (I), and pharmaceutically acceptable salts, solvates, hydrates, polymorphs, co-crystals, tautomers, stereoisomers, isotopologues, prodrugs, and compositions thereof, for use in selectively inhibiting the activity of a kinase (e.g., a JNK (e.g., JNK2)) in a subject, biological sample, tissue, or cell.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g., prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry*, $7^{th}$ Edition, John Wiley & Sons, Inc., New York, 2013; Richard C. Larock, *Comprehensive Organic Transformations*, John Wiley & Sons, Inc., New York, 2018; and Carruthers, Some Modem Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, the bond ∿ is a single bond, the dashed line --- is a single bond or absent, and the bond ═ or ═ is a single or double bond.

The term "isotopologue" refers to compounds that differ only in their isotopic composition. Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values ("range") is listed, it is intended to encompass each value and sub-range within the range. A range is inclusive of the values at the two ends of the range unless otherwise provided. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $-CH_2F$, $-CHF_2$, $-CF_3$, $-CH_2CH_2F$, $-CH_2CHF_2$, $-CH_2CF_3$, or benzyl (Bn)).

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 12 carbon atoms and 1 or more heteroatoms within the parent chain ("hetero$C_{1-12}$ alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$ alkyl. In certain embodiments, the heteroalkyl group is a substituted hetero$C_{1-12}$ alkyl.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═CHCH$_3$ or

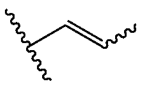

may be an (E)- or (Z)-double bond.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., —CH═CHCH$_3$ or

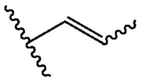

) may be in the (E)- or (Z)-configuration.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("hetero$C_{1-20}$ alkynyl"). In certain embodiments, a heteroalkynyl group refers to a group having from 1 to 10 carbon atoms, at least one triple bond, and 1 or more heteroatoms within the parent chain ("hetero$C_{1-10}$ alkynyl"). In some embodiments, a heteroalkynyl group has 1 to 9 carbon atoms, at least one triple bond, and 1 or more heteroatoms within the parent chain ("hetero$C_{1-9}$ alkynyl"). In some embodiments, a heteroalkynyl group has 1 to 8 carbon atoms, at least one triple bond, and 1 or more heteroatoms within the parent chain ("hetero$C_{1-8}$ alkynyl"). In some embodiments, a heteroalkynyl group has 1 to 7 carbon atoms, at least one triple bond, and 1 or more heteroatoms within the parent chain ("hetero$C_{1-7}$ alkynyl"). In some embodiments, a heteroalkynyl group has 1 to 6 carbon atoms, at least one triple bond, and 1 or more heteroatoms within the parent chain ("hetero$C_{1-6}$ alkynyl").

In some embodiments, a heteroalkynyl group has 1 to 5 carbon atoms, at least one triple bond, and 1 or 2 heteroatoms within the parent chain ("hetero$C_{1-5}$ alkynyl"). In some embodiments, a heteroalkynyl group has 1 to 4 carbon atoms, at least one triple bond, and lor 2 heteroatoms within the parent chain ("hetero$C_{1-4}$ alkynyl"). In some embodiments, a heteroalkynyl group has 1 to 3 carbon atoms, at least one triple bond, and 1 heteroatom within the parent chain ("hetero$C_{1-3}$ alkynyl"). In some embodiments, a heteroalkynyl group has 1 to 2 carbon atoms, at least one triple bond, and 1 heteroatom within the parent chain ("hetero$C_{1-2}$ alkynyl"). In some embodiments, a heteroalkynyl group has 1 to 6 carbon atoms, at least one triple bond, and 1 or 2 heteroatoms within the parent chain ("hetero$C_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{1-20}$ alkynyl. In certain embodiments, the heteroalkynyl group is a substituted hetero$C_{1-20}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5]undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C═C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The "saturated" or "fully saturated" refers to a moiety that does not contain a double or triple bond, e.g., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$—, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =NN($R^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{aa}$; each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_120$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_6$-10 aryl and 5-10 membered heteroaryl, or two $R^f$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —C$_2$O$_2$H, —CO$_2$(C$_{1-6}$ alkyl), —OC(=O)(C$_{1-6}$ alkyl), —OCO$_2$(C)C(=O)N, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{GG}$ substituents can be joined to form =O or =S; and each $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR—, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP $(R^{cc})_2$, —$OP(R^{cc})_3^+X^-$, —$OP(OR^{cc})_2$, —$OP(OR^{cc})_3^+X^-$, —$OP(=O)(R^{aa})_2$, —$OP(=O)(OR^{cc})_2$, and —$OP(=O)(N(R^{bb}))_2$, wherein $X^-$, $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —$S=SR^c$, —$SC(=S)SR^{aa}$, —$SC(=S)OR^{aa}$, —$SC(=S)\ N(R^{bb})_2$, —$SC(=O)SR^{aa}$, —$SC(=O)OR^{aa}$, —$SC(=O)N(R^{bb})_2$, and —$SC(=O)R^{aa}$, wherein $R^{aa}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —$NHC(=O)R_{aa}$, —$NHCO_2R^{aa}$, —$NHC(=O)N(R^{bb})_2$, —$NHC(=NR^{bb})N(R^{bb})_2$, —$NHSO_2R^{aa}$, —$NHP(=O)(OR^{cc})_2$, and —$NHP(=O)(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}C(=O)R^{aa}$, —$NR^{bb}CO_2R^{aa}$, —$NR^{bb}C(=O)N(R^{bb})_2$, —$NR^{bb}C(=NR^{bb})N(R^{bb})_2$, —$NR^{bb}SO_2R^{aa}$, —$NR^{bb}P(=O)(OR^{cc})_2$, and —$NR^{bb}P(=O)(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})_3$ and —$N(R^{bb})_3^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —$S(=O)R^{aa}$, wherein $R^{aa}$ is as defined herein.

The term "acyl" refers to a group having the general formula —$C(=O)R^{X1}$, —$C(=O)OR^{X1}$, —$C(=O)—O—C(=O)R^{X1}$, —$C(=O)SR^{X1}$, —$C(=O)N(R^{X1})_2$, —$C(=S)R^{X1}$, —$C(=S)N(R^{X1})_2$, and —$C(=S)S(R^{X1})$, —$C(=NR^{X1})R^{X1}$, —$C(=NR^{X1})OR^{X1}$, —$C(=NR^{X1})SR^{X1}$, and —$C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—$C(=O)R^{aa}$), carboxylic acids (—$CO_2H$), aldehydes (—CHO), esters (—$CO_2R^{aa}$, —$C(=O)SR^{aa}$, —$C(=S)SR^{aa}$), amides (—$C(=O)N(R^{bb})_2$, —$C(=O)NR^{bb}SO_2R^{aa}$, —$C(=S)N(R^{bb})_2$), and imines (—$C(=NR^{bb})R^{aa}$, —$C(=NR^{bb})OR^{aa}$), —$C(=NR^{bb})N(R^{bb})_2$), wherein $R^{aa}$ and $R^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{\circ})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis, T. W. Greene and P. G. M. Wuts,* 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as a "hydroxyl protecting group"). Oxygen protecting groups include, but are not limited to, —$R^{aa}$, —N($R^{bb}$)$_2$, —C(═O)S$R^{aa}$, —C(═O)$R^{aa}$, —C$O_2R^{aa}$, —C(═O)N($R^{bb}$)$_2$, —C(═N$R^{bb}$)$R^{aa}$, —C(═N$R^{bb}$)O$R^{aa}$, —C(═N$R^{bb}$)

$N(R^{bb})_2$, $—S(═O)R^{aa}$, $—SO_2R^{aa}$, $—Si(R^{cc})_3$, $—P(R^{cc})_2$, $—P(R^{cc})_3^+X^-$, $—P(OR^{cc})_2$, $—P(OR^{cc})_3^+X^-$, $—P(═O)(R^{aa})_2$, $—P(═O)(OR^{cc})_2$, and $—P(═O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{a}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(═O)(R^{cc})_2$, $—P(═O)(OR^{cc})_2$, and $—P(═O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

A "counterion" or "anionic counterion" is a negatively charged group associated with a positively charged group in order to maintain electronic neutrality. An anionic counterion may be monovalent (e.g., including one formal negative charge). An anionic counterion may also be multivalent (e.g., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., $—OC(═O)SR^{aa}$, $—OC(═O)R^{aa}$, $—OCO_2R^{aa}$, $—OC(═O)N(R^{bb})_2$, $—OC(═NR^{bb})R^{aa}$, $—OC(═NR^{bb})OR^{aa}$, $—OC(═NR^{bb})N(R^{bb})_2$, $—OS(═O)R^{aa}$, $—OSO_2R^{aa}$, $—OP(R^{cc})_2$, $—OP(R^{aa})_3$, $—OP(═O)_2R^{aa}$, $—OP(═O)(R^{aa})_2$, $—OP(═O)$ $(OR^{cc})_2$, $—OP(=O)_2N(R^{bb})_2$, and $—OP(=O)(NR^{bb})_2$, wherein $R^{aa}$, $R^{bb}$, and $R^{cc}$ are as defined herein).

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the $—CH_2OH$ side branch. The alternative form, in which the $—CH_2OH$ substituent and the anomeric hydroxyl are on the same side (cis) of the plane of the ring, is called a R anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans.

Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

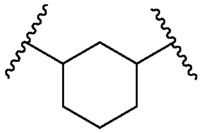 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C═C and/or C≡C bonds anywhere in the hydrocarbon chain. For instance, —CH═CH—$(CH_2)_2$—, —$CH_2$—C≡C—$CH_2$—, and —C≡C—CH═CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

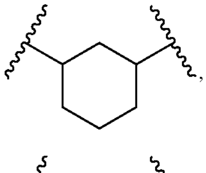,
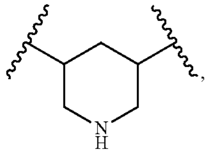,
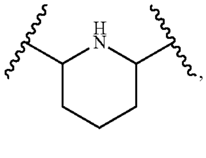,
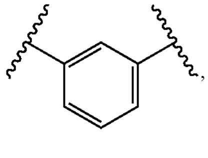,

-continued

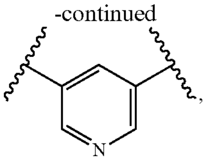, and

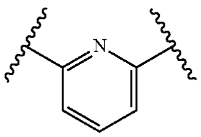 [SMILES: *c1cccc(*)n1]

are all examples of a hydrocarbon chain. In contrast, in certain embodiments,

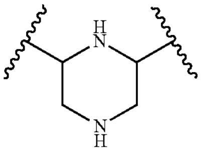
and
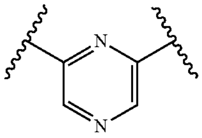

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

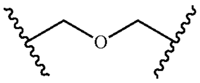 [SMILES: *COC*]

is a $C_3$ hydrocarbon chain wherein one chain atom is replaced with an oxygen atom.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R\cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot 0.5\ H_2O$)), and polyhydrates (x is a number greater than 1, e.g., dihydrates ($R\cdot 2\ H_2O$) and hexahydrates ($R\cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibition of JNK (e.g., JNK2).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for inhibition of JNK (e.g., JNK2).

As used herein the term "inhibit" or "inhibition" in the context of proteins, for example, in the context of JNK, refers to a reduction in the activity of the kinase. In some embodiments, the term refers to a reduction of the level of activity, e.g., JNK2 activity, to a level that is statistically significantly lower than an initial level, which may, for example, be a baseline level of activity. In some embodiments, the term refers to a reduction of the level of enzyme activity, e.g., JNK2 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMKla, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CKla, CKla2, CKlaps1, CKlaps2, CKlaps3, CKld, CKle, CKlg1, CK1g2, CKlg2ps, CK1g3, CK2a1, CK2a1-rs, CK2a2, CLIK1, CLIKIL, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRKIA, DYRKIB, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erkl, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obsen, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKpsl, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Weel, WeelB, WeelBps, Weelpsl, Weelps2, Wnkl, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "inhibition," "inhibiting," "inhibit," or "inhibitor" refer to the ability of a compound to reduce, slow, halt or prevent activity of a particular biological process (e.g., a kinase) in a cell relative to vehicle.

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon $\alpha$, interferon $\gamma$), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

When a compound, pharmaceutical composition, method, use, or kit is referred to as "selectively," "specifically," or "competitively" inhibiting a JNK kinase, pharmaceutical composition, method, use, or kit inhibits the HMT to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different HMT.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

DETAILED DESCRIPTION OF CERTAIN EMBODIMENTS OF THE INVENTION

Figure 1:
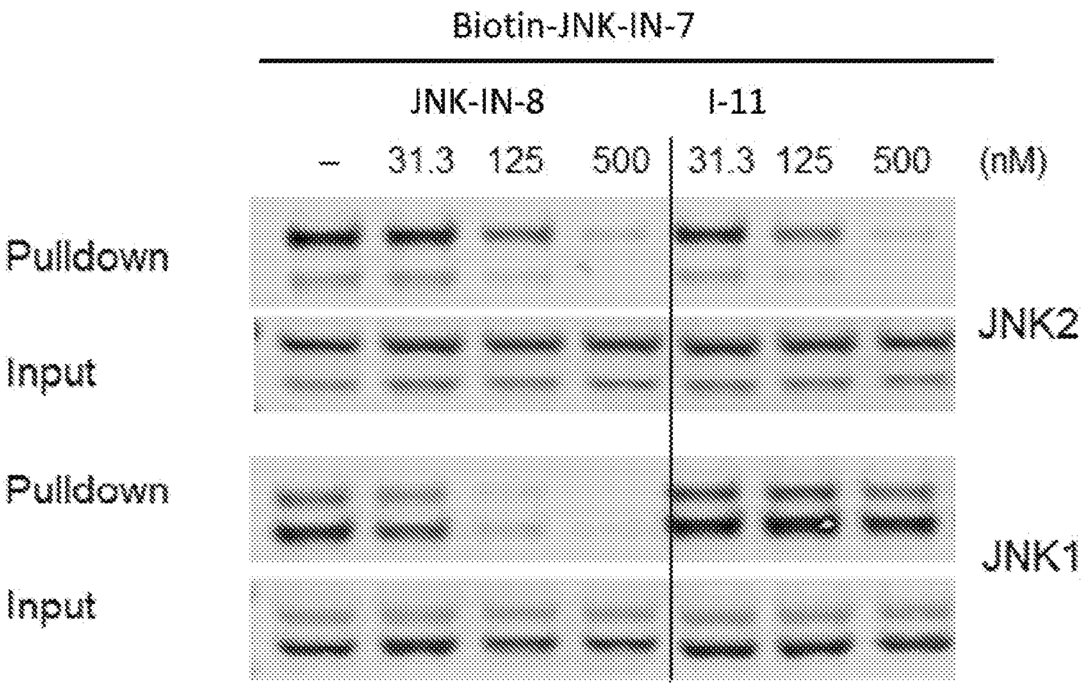
FIG. 1 shows competition pulldown experiments from multiple myeloma MM1.S cells with a biotin-JNK-IN-7 as probe.

The present invention provides compounds that inhibit a kinase, and pharmaceutical compositions thereof, for the prevention and treatment of a subject with a disease. In certain embodiments, the compounds selectively inhibit a kinase. In certain embodiments, the compounds inhibit JNKs. In certain embodiments, the compounds selectively inhibit JNKs. In certain embodiments, the compounds irreversibly inhibit JNK. The present invention further provides methods of using the compounds described herein, e.g., as biological probes to study the inhibition of JNK activity, and as therapeutics, e.g., in the prevention and treatment of diseases associated with JNK activity. In certain embodiments, the diseases include, but are not limited to, proliferative diseases (e.g., cancer and benign neoplasms), inflammatory diseases (e.g., rheumatoid arthritis), autoimmune diseases, and cardiovascular diseases (e.g., atherosclerosis) in a subject, biological sample, tissue, or cell.

Compounds

Certain aspects of the present disclosure relate to the compounds described herein. The compounds described herein may be useful in treating and/or preventing a disease (e.g., proliferative diseases (e.g., cancer and benign neoplasms), inflammatory diseases (e.g., rheumatoid arthritis), autoimmune diseases, cardiovascular diseases (e.g., atherosclerosis)), or diseases associated with the activity of a JNK (e.g., JNK2) in a subject, or inhibiting the activity of a JNK (e.g., JNK2) in a subject, biological sample, tissue, or cell. In certain embodiments, a compound described herein is a compound of Formula (I), or a pharmaceutically acceptable salt, solvate, hydrate, polymorph, co-crystal, tautomer, stereoisomer, isotopologue, or prodrug thereof. In certain embodiments, a compound described herein is a compound of Formula (I), or a pharmaceutically acceptable salt thereof.

In certain embodiments, a compound described herein is of Formula (I):

(I)

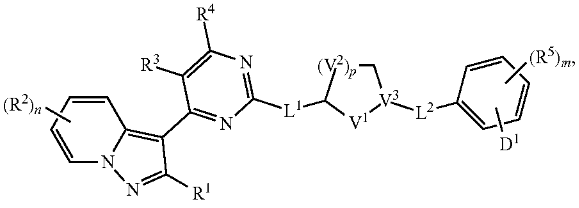

or a pharmaceutically acceptable salt, solvate, hydrate, tautomer, or stereoisomer thereof, wherein:

$R^1$ is optionally substituted aryl or optionally substituted heteroaryl;

$R^2$, $R^3$, $R^4$, and $R^5$ are each independently hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$NO_2$, —CN, —SCN, —$OR^{D1}$, —$N(R^{D1})_2$ or —$SR^{D1}$, wherein $R^{D1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom;

n is 1, 2, or 3;

m is 1, 2, 3, or 4;

$L^1$ is O, S, or —$N(R^a)$—, wherein $R^a$ is hydrogen, optionally substituted acyl, optionally substituted $C_{1-6}$ alkyl, or a nitrogen protecting group;

$L^2$ is O, S, —$N(R^{L2a})$, —C(=O)—, —$NR^{L2a}C(=O)$—, or —$C(=O)NR^{L2a}$— wherein $R^{L2a}$ is hydrogen, optionally substituted acyl, optionally substituted $C_{1-6}$ alkyl, or a nitrogen protecting group;

$V^1$ is $C(R^{1a})H$;

$V^2$ is $C(R^{1b})H$;

$V^3$ is N or $C(R^{1c})$;

$R^{1a}$ and $R^{1b}$ are independently hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{C1}$, —$N(R^{C1})_2$, or —$SR^{C1}$, wherein $R^{C1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or $R^{1a}$ and $R^{1b}$ are joined together to form an optionally substituted bridged ring;

$R^{1c}$ is hydrogen, or substituted or unsubstituted $C_{1-6}$ alkyl;

p is 1, 2, or 3;

$D^1$ is a warhead of any one of Formulae (i-1) to (i-42):

(i-1)

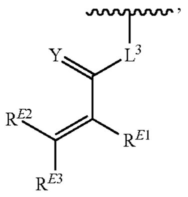

(i-2)

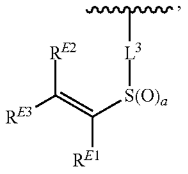

(i-3)

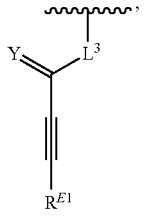

(i-4)

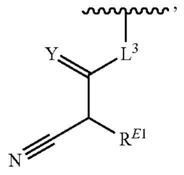

(i-5)

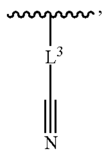

(i-6)

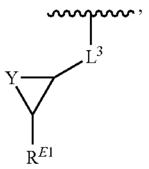

-continued (i-7)

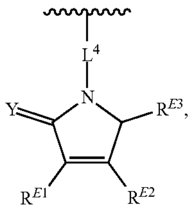

(i-8)

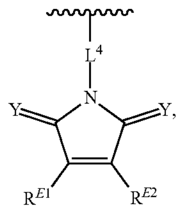

(i-9)

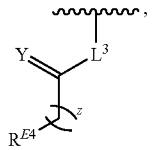

(i-10)

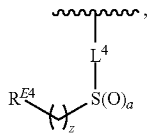

(i-11)

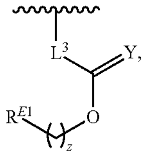

(i-12)

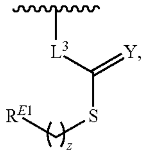

(i-13)

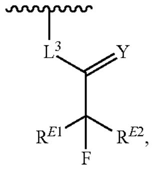

(i-14)

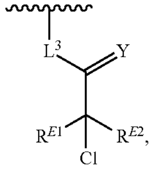

(i-15)

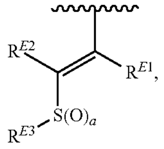

-continued
(i-16)
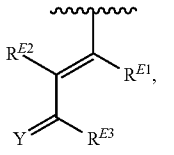
(i-17)
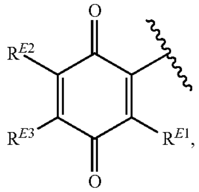
(i-18)
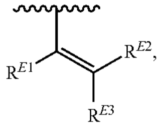
(i-19)
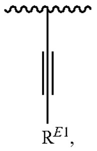
(i-20)
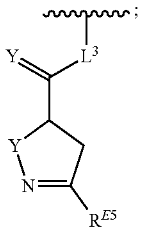
(i-21)
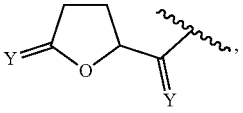
(i-22)
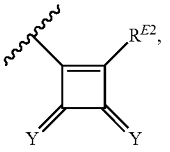
(i-23)
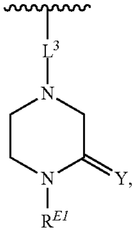
-continued
(i-24)
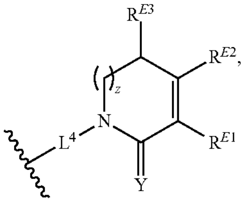
(i-25)
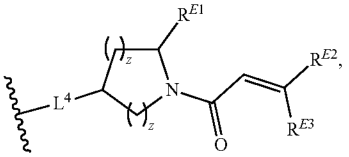
(i-26)
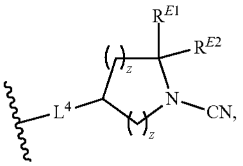
(i-27)
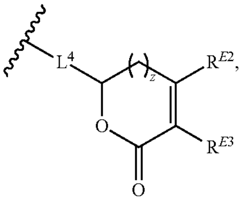
(i-28)
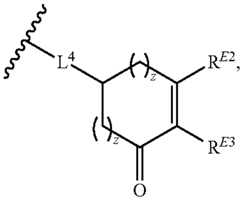
(i-29)
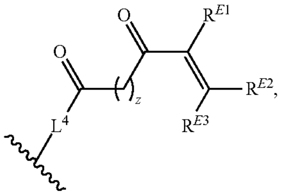
(i-30)
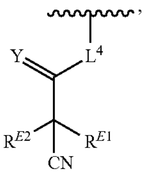
(i-31)
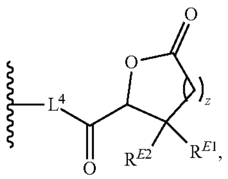

-continued (i-32)

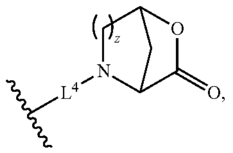

(i-33)

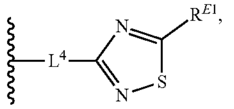

(i-34)

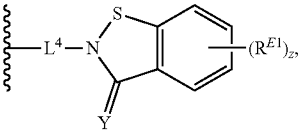

(i-35)

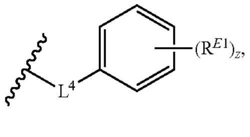

(i-36)

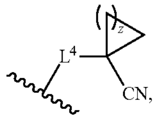

(i-37)

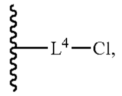

(i-38)

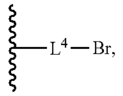

(i-39)

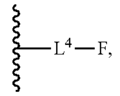

(i-40)

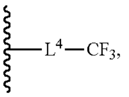

(i-41)

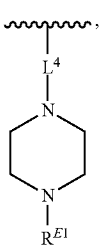

and

-continued (i-42)

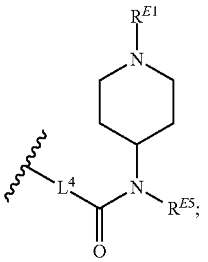

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$, —$NR^{L3a}$S(═O)—, —$S(=O)_2$—, —$S(=O)_2O$—, —$OS(=O)_2$—, —$S(=O)_2NR^{L3a}$—, or —$NR^{L3a}S(=O)_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, or —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, or —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, $—CH_2OR^{E3a}$, $—CH_2N(R^{E3a})_2$, $—CH_2SR^{E3a}$, $—OR^{E3a}$, $—N(R^{E3a})_2$, or $—SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or $NR^{E6}$, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

Formula (I) contains the substituent $R^1$. In certain embodiments, RV is optionally substituted aryl. In certain embodiments, $R^1$ is substituted phenyl. In certain embodiments, $R^1$ is unsubstituted phenyl. In certain embodiments, $R^1$ is 4-methoxyphenyl. In certain embodiments, $R^1$ is 4-chlorophenyl. In certain embodiments, $R^1$ is not hydrogen. In certain embodiments, $R^1$ is optionally substituted heteroaryl. In certain embodiments, $R^1$ is substituted or unsubstituted pyridine. In certain embodiments, $R^1$ is unsubstituted pyridine. In certain embodiments, $R^1$ is substituted or unsubstituted pyrimidine.

Formula (I) includes the substituents $R^2$, $R^3$, $R^4$, and $R^5$. In certain embodiments, Formula (I) includes one or more instances of substituent $R^2$, $R^3$, $R^4$, or $R^5$. In certain embodiments, n is 1. In certain embodiments, n is 2. In certain embodiments, n is 3. In certain embodiments, m is 1. In certain embodiments, m is 2. In certain embodiments, m is 3. In certain embodiments, m is 4. In certain embodiments, at least one instance of $R^2$, $R^3$, $R^4$, or $R^5$ is hydrogen. In certain embodiments, at least one instance of $R^2$, $R^3$, $R^4$, or $R^5$ is halogen. In certain embodiments, at least one instance of $R^2$, $R^3$, $R^4$, or $R^5$ is optionally substituted acyl. In certain embodiments, at least one instance of $R^2$, $R^3$, $R^4$, or $R^5$ optionally substituted alkyl (e.g., $C_{1-6}$ alkyl, e.g., Me, Et, Pr, or Bu). In certain embodiments, at least one instance of $R^2$, $R^3$, $R^4$, or $R^5$ optionally substituted alkenyl (e.g., substituted or unsubstituted vinyl or substituted or unsubstituted allyl). In certain embodiments, at least one instance of $R^2$, $R^3$, $R^4$, or $R^5$ is optionally substituted alkynyl (e.g., $C_{2-6}$ alkynyl). In certain embodiments, at least one instance of $R^2$ is optionally substituted carbocyclyl. In certain embodiments, at least one instance of $R^2$, $R^3$, $R^4$, or $R^5$ is optionally substituted heterocyclyl. In certain embodiments, at least one instance of $R^2$ is optionally substituted aryl. In certain embodiments, at least one instance of $R^2$, $R^3$, $R^4$, or $R^5$ is optionally substituted heteroaryl. In certain embodiments, at least one instance of $R^2$, $R^3$, $R^4$, or $R^5$ is $—NO_2$. In certain embodiments, at least one instance of $R^2$, $R^3$, $R^4$, or $R^5$ is —CN. In certain embodiments, at least one instance of $R^2$ is —SCN. In certain embodiments, at least one instance of $R^2$, $R^3$, $R^4$, or $R^5$ is $OR^{D1}$, wherein $R^{D1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, at least one instance of $R^2$, $R^3$, $R^4$, or $R^5$ is $N(R^{D1a})_2$, wherein $R^{D1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, at least one instance of $R^2$ is $SR^{D1}$, wherein $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group.

In certain embodiments, $R^3$ and $R^4$ are the same. In certain embodiments, $R^3$ and $R^4$ are different. In certain embodiments, $R^3$ is hydrogen, and $R^4$ is hydrogen. In certain embodiments, $R^3$ is hydrogen, $R^4$ is hydrogen, and $R^1$ is not hydrogen. In certain embodiments, $R^3$ is hydrogen, $R^4$ is hydrogen, and $R^1$ is optionally substituted aryl. In certain embodiments, $R^3$ is hydrogen, $R^4$ is hydrogen, and $R^1$ is phenyl. In certain embodiments, $R^3$ is hydrogen, $R^4$ is hydrogen, and $R^1$ is 4-methoxyphenyl. In certain embodiments, $R^3$ is hydrogen, $R^4$ is hydrogen, and $R^1$ is 4-chlorophenyl. In certain embodiments, $R^3$ is hydrogen, $R^4$ is hydrogen, and $R^1$ is heteroaryl. In certain embodiments, $R^3$ is hydrogen, $R^4$ is hydrogen, and $R^1$ is pyridyl.

In certain embodiments, $R^2$ is hydrogen, $R^3$ is hydrogen, and $R^4$ is hydrogen. In certain embodiments, $R^2$ is hydrogen, $R^3$ is hydrogen, $R^4$ is hydrogen, and $R^1$ is not hydrogen. In certain embodiments, $R^2$ is hydrogen, $R^3$ is hydrogen, $R^4$ is hydrogen, and $R^1$ is optionally substituted aryl. In certain embodiments, $R^2$ is hydrogen, $R^3$ is hydrogen, $R^4$ is hydrogen, and $R^1$ is phenyl. In certain embodiments, $R^2$ is hydrogen, $R^3$ is hydrogen, $R^4$ is hydrogen, and $R^1$ is 4-methoxyphenyl. In certain embodiments, $R^2$ is hydrogen, $R^3$ is hydrogen, $R^4$ is hydrogen, and $R^1$ is 4-chlorophenyl. In certain embodiments, $R^2$ is hydrogen, $R^3$ is hydrogen, $R^4$ is hydrogen, and $R^1$ is heteroaryl. In certain embodiments, $R^2$ is hydrogen, $R^3$ is hydrogen, $R^4$ is hydrogen, and $R^1$ is pyridyl.

In certain embodiments, $R^2$ is hydrogen, $R^3$ is hydrogen, $R^4$ is hydrogen, and $R^5$ is hydrogen. In certain embodiments, $R^2$ is hydrogen, $R^3$ is hydrogen, $R^4$ is hydrogen, $R^5$ is hydrogen, and $R^1$ is not hydrogen. In certain embodiments, $R^2$ is hydrogen, $R^3$ is hydrogen, $R^4$ is hydrogen, $R^5$ is hydrogen, and $R^1$ is optionally substituted aryl. In certain embodiments, $R^2$ is hydrogen, $R^3$ is hydrogen, $R^4$ is hydrogen, $R^5$ is hydrogen, and $R^1$ is phenyl. In certain embodiments, $R^2$ is hydrogen, $R^3$ is hydrogen, $R^4$ is hydrogen, $R^5$ is hydrogen, and $R^1$ is 4-methoxyphenyl. In certain embodiments, $R^2$ is hydrogen, $R^3$ is hydrogen, $R^4$ is hydrogen, $R^5$ is hydrogen, and $R^1$ is 4-chlorophenyl. In certain embodiments, $R^2$ is hydrogen, $R^3$ is hydrogen, $R^4$ is hydrogen, $R^5$ is hydrogen, and $R^1$ is heteroaryl. In certain embodiments, $R^2$ is hydrogen, $R^3$ is hydrogen, $R^4$ is hydrogen, $R^5$ is hydrogen, and $R^1$ is pyridyl.

In certain embodiments, $R^2$ is methyl. In certain embodiments, $R^2$ is methyl, $R^3$ is hydrogen, and $R^4$ is hydrogen. In certain embodiments, $R^2$ is methyl, $R^3$ is hydrogen, $R^4$ is hydrogen, and $R^1$ is not hydrogen. In certain embodiments, $R^2$ is methyl, $R^3$ is hydrogen, $R^4$ is hydrogen, and $R^1$ is optionally substituted aryl. In certain embodiments, $R^2$ is methyl, $R^3$ is hydrogen, $R^4$ is hydrogen, and $R^1$ is phenyl. In certain embodiments, $R^2$ is methyl, $R^3$ is hydrogen, $R^4$ is hydrogen, and $R^1$ is 4-methoxyphenyl. In certain embodiments, $R^2$ is methyl, $R^3$ is hydrogen, $R^4$ is hydrogen, and $R^1$ is 4-chlorophenyl. In certain embodiments, $R^2$ is methyl, $R^3$ is hydrogen, $R^4$ is hydrogen, and $R^1$ is heteroaryl. In certain embodiments, $R^2$ is methyl, $R^3$ is hydrogen, $R^4$ is hydrogen, and $R^1$ is pyridyl.

In certain embodiments, $R^2$ is methoxy. In certain embodiments, $R^2$ is methoxy, $R^3$ is hydrogen, and $R^4$ is hydrogen. In certain embodiments, $R^2$ is methoxy, $R^3$ is hydrogen, $R^4$ is hydrogen, and $R^1$ is not hydrogen. In certain embodiments, $R^2$ is methoxy, $R^3$ is hydrogen, $R^4$ is hydrogen, and $R^1$ is optionally substituted aryl. In certain embodiments, $R^2$ is methoxy, $R^3$ is hydrogen, $R^4$ is hydrogen, and $R^1$ is phenyl. In certain embodiments, $R^2$ is methoxy, $R^3$ is hydrogen, $R^4$ is hydrogen, and $R^1$ is 4-methoxyphenyl. In certain embodiments, $R^2$ is methoxy, $R^3$ is hydrogen, $R^4$ is hydrogen, and $R^1$ is 4-chlorophenyl. In certain embodiments, $R^2$ is methoxy, $R^3$ is hydrogen, $R^4$ is hydrogen, and $R^1$ is heteroaryl. In certain embodiments, $R^2$ is methoxy, $R^3$ is hydrogen, $R^4$ is hydrogen, and $R^1$ is pyridyl.

Formula (I) includes substituent $L^1$. In certain embodiments, $L^1$ is —O—. In certain embodiments, $L^1$ is —S—. In certain embodiments, $L^1$ is —$N(R^a)$— as valency permits, wherein $R^a$ is independently hydrogen, substituted or unsubstituted $C_{1-6}$ alkyl, or a nitrogen protecting group. In certain embodiments, $R^a$ is hydrogen. In certain embodiments, $R^a$ is $C_{1-6}$ alkyl. In certain embodiments, $R^a$ is substituted or unsubstituted methyl. In certain embodiments, $L^1$ is —NH—.

Formula (I) includes substituent $L^2$. In certain embodiments, $L^2$ is —O—. In certain embodiments, $L^2$ is —S—. In certain embodiments, $L^2$ is $N(R^{L2a})$ as valency permits, wherein $R^{L2a}$ is independently hydrogen, substituted or unsubstituted $C_{1-6}$ alkyl, or a nitrogen protecting group. In certain embodiments, $R^{L2a}$ is hydrogen. In certain embodiments, $R^{L2a}$ is $C_{1-6}$ alkyl. In certain embodiments, $R^{L2a}$ is substituted or unsubstituted methyl. In certain embodiments, $L^2$ is —C(=O)—. In certain embodiments, $L^2$ is —$NR^{L2a}C$(=O)—, wherein $R^{L2a}$ is hydrogen, optionally substituted acyl, optionally substituted $C_{1-6}$ alkyl, or a nitrogen protecting group. In certain embodiments, $L^2$ is —C(=O)$NR^{L2a}$—, wherein $R^{L2a}$ is hydrogen, optionally substituted acyl, optionally substituted $C_{1-6}$ alkyl, or a nitrogen protecting group. In certain embodiments, $L^2$ is —C(=O)NH—.

Formula (I) includes the substituent $V^1$. In certain embodiments, $V^1$ is of the formula: $C(R^{1a})H$. In certain embodiments, $R^{1a}$ is hydrogen. In certain embodiments, $R^{1a}$ is halogen. In certain embodiments, $R^1a$ is optionally substituted acyl. In certain embodiments, $R^{1a}$ is optionally substituted alkyl. In certain embodiments, $R^{1a}$ is optionally substituted alkenyl. In certain embodiments, $R^1a$ is optionally substituted alkynyl. In certain embodiments, the $R^{1a}$ forms a bicyclic ring system with another atom in the ring. In certain embodiments, $R^{1a}$ is optionally substituted carbocyclyl. In certain embodiments, $R^{1a}$ is optionally substituted heterocyclyl. In certain embodiments, $R^{1a}$ is optionally substituted aryl. In certain embodiments, $R^{1a}$ is optionally substituted heteroaryl. In certain embodiments, $R^{1a}$ is —CN. In certain embodiments, $R^{1a}$ is —$OR^{C1}$, wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1a}$ is —$N(R^{C1})_2$ wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1a}$ is —$SR^{C1}$ wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom.

Certain instances of Formula (I) include the substituent $V^2$. In certain embodiments, Formula (I) contains no instances of $V^2$. In certain embodiments, p is 0. In certain embodiments, p is 1. In certain embodiments, p is 2. In certain embodiments, p is 3. In certain embodiments, $V^2$ is of the formula: $C(R^{1b})H$. In certain embodiments, $R^{1b}$ is hydrogen. In certain embodiments, $R^{1b}$ is halogen. In certain embodiments, $R^{1b}$ is optionally substituted acyl. In certain embodiments, $R^{1b}$ is optionally substituted alkyl. In certain embodiments, $R^{1b}$ is optionally substituted alkenyl. In certain embodiments, $R^{1b}$ is optionally substituted alkynyl. In certain embodiments, $R^{1b}$ is optionally substituted carbocyclyl. In certain embodiments, $R^{1b}$ is optionally substituted heterocyclyl. In certain embodiments, $R^{1b}$ is optionally substituted aryl. In certain embodiments, $R^{1b}$ is optionally substituted heteroaryl. In certain embodiments, $R^{1b}$ is —(=O)—. In certain embodiments, $R^{1b}$ is —CN. In certain embodiments, $R^{1b}$ is —$OR^{C1}$ wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1b}$ is —$N(R^{C1})_2$ wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1b}$ is —$SR^{C1}$, wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1a}$ and $R^{1b}$ are joined together to form an optionally substituted bridged ring.

In certain embodiments, $V_1$ is —$CH_2$—, and $V_2$ is —$CH_2$—. In certain embodiments, $V_1$ is —$CH_2$—, and $V_2$ is —C(H)F—. In certain embodiments, $V_1$ is —$CH_2$—, and $V_2$ is —C(H)Me-. In certain embodiments, $V_1$ is —$CH_2$—, $V_2$ is —$CH_2$—, and p=1. In certain embodiments, $V_1$ is —$CH_2$—, $V_2$ is —$CH_2$—, and p=2. In certain embodiments, $V_1$ is —$CH_2$—, $V_2$ is —$CH_2$—, and p=3. In certain embodiments, $V_1$ is —$CH_2$—, $V_2$ is —$CH_2$—, and $V_3$ is —CH—. In certain embodiments, $V_1$ is —$CH_2$—, $V_2$ is —$CH_2$—, and $V_3$ is —N—.

Formula (I) includes the substituent $V^3$. In certain embodiments, $V^3$ is —N—. In certain embodiments, $V^3$ is of the formula: —C($R^{1c}$)—. In certain embodiments, $R^{1c}$ is hydrogen. In certain embodiments, $R^{1c}$ is halogen. In certain embodiments, $R^{1c}$ is optionally substituted acyl. In certain embodiments, $R^{1c}$ is optionally substituted alkyl. In certain embodiments, $R^{1c}$ is optionally substituted alkenyl. In certain embodiments, $R^{1c}$ is optionally substituted alkynyl. In certain embodiments, $R^{1c}$ is optionally substituted carbocyclyl. In certain embodiments, $R^{1c}$ is optionally substituted heterocyclyl. In certain embodiments, $R^{1c}$ is optionally substituted aryl. In certain embodiments, $R^{1c}$ is optionally substituted heteroaryl. In certain embodiments, $R^{1c}$ is —CN. In certain embodiments, $R^{1c}$ is —$OR^{C1}$ wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1c}$ is —$N(R^{C1})_2$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom. In certain embodiments, $R^{1c}$ is —$SR^{C1}$ wherein each occurrence of $R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom.

In certain embodiments, $V^1$ is —$CH_2$—, $V_2$ is —$CH_2$—, and $V_3$ is —N—. In certain embodiments, $V^1$ is —$CH_2$—, $V_2$ is —C(Me)H—, and $V_3$ is —N—. In certain embodiments, $V^1$ is —$CH_2$—, $V_2$ is —C(F)H—, and $V_3$ is —N—. In certain embodiments, Formula (I) is of the formula:

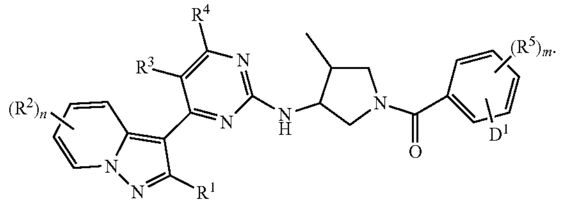

In certain embodiments, Formula (I) is of the formula:

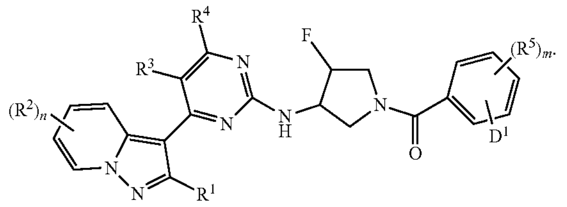

In certain embodiments, $V^1$ is —$CH_2$, $V_2$ is —$CH_2$—, and $V_3$ is —CH. In certain embodiments, $V^1$ is —$CH_2$, $V_2$ is —$CH_2$, $V_3$ is —CH, and p=2.

In certain embodiments, $L^1$ is —NH—, $V^1$ is —$CH_2$—, $V_3$ is —N, and $V_2$ is —$CH_2$. In certain embodiments, $L^1$ is —NH—, $V^1$ is $CH_2$, $V_3$ is N, $V_2$ is $CH_2$, and p=0. In certain embodiments, $L^1$ is —NH, $V^1$ is $CH_2$, $V_3$ is N, $V_2$ is $CH_2$, and p=1. In certain embodiments, $L^1$ is —NH—, $V^1$ is $CH_2$, $V_3$ is N, $V_2$ is $CH_2$, and p=2. In certain embodiments, $L^1$ is —NH—, $V^1$ is —$CH_2$—, $V_3$ is —N—, $V_2$ is —$CH_2$—, and p=3. In certain embodiments, $L^1$ is —NH—, $V^1$ is —$CH_2$—, $V_3$ is —N—, $V_2$ is —$CH_2$—, and p=$^3$.

In certain embodiments, Formula (I) is of the formula:

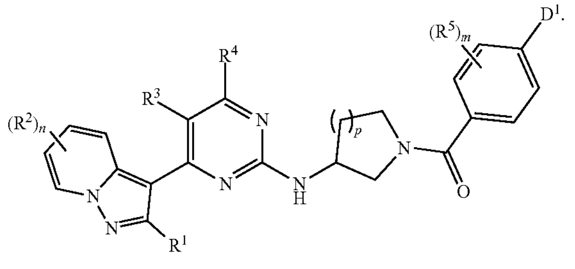

In certain embodiments, Formula (I) is of the formula:

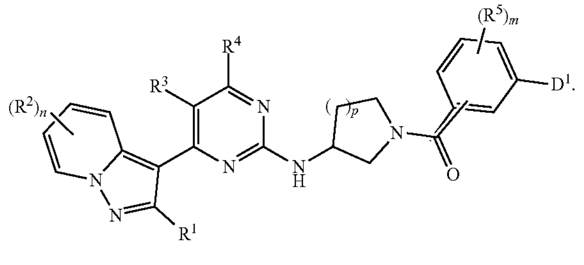

In certain embodiments, Formula (I) is of the formula:

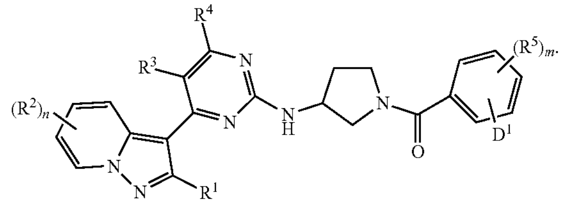

In certain embodiments, Formula (I) is of the formula:

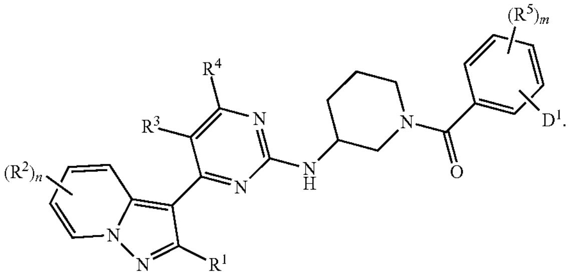

In certain embodiments, Formula (I) is of the formula:

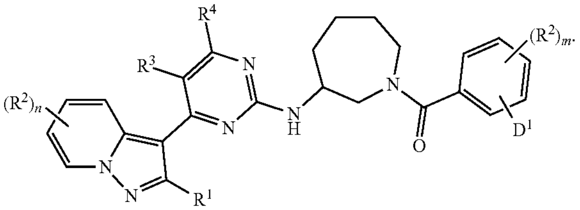

In certain embodiments, $L^1$ is —NH—, $V^1$ is $C(R^{1a})H$, $V_3$ is N, and one instance of $V_2$ is $C(R^{1b})H$, wherein $R^{1a}$ and $R^{1b}$ are joined together to form an optionally substituted bridged ring. In certain embodiments, Formula (I) is of the formula:

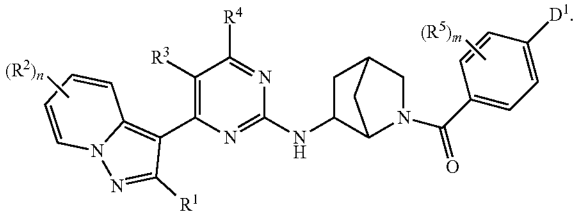

In certain embodiments, Formula (I) is of the formula:

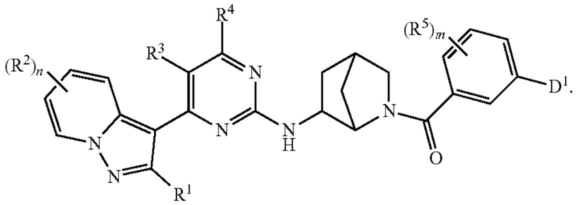

In certain embodiments, $L^1$ is —NH—, $V^1$ is $CH_2$, $V_3$ is CH, and $V_2$ is $CH_2$. In certain embodiments, Formula (I) is of the formula:

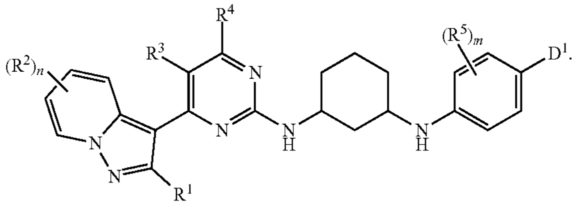

In certain embodiments, Formula (I) is of the formula:

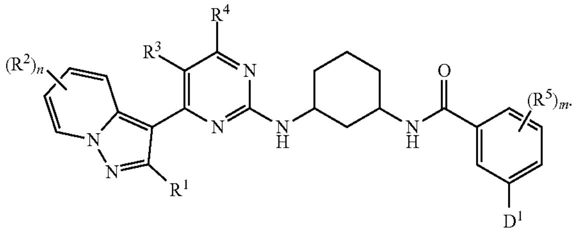

As generally defined herein, Formula (I) includes substituent $D^1$, wherein $D^1$ is a warhead of Formulae (i-1) to (i-42):

(i-1)

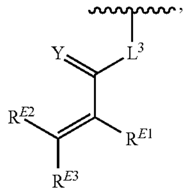

(i-2)

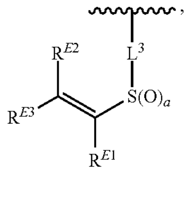

-continued
(i-3)
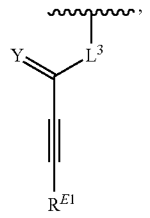
(i-4)
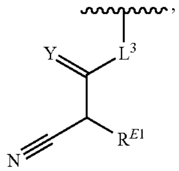
(i-5)
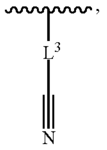
(i-6)
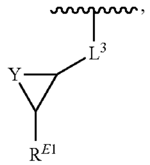
(i-7)
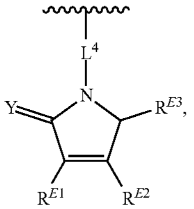
(i-8)
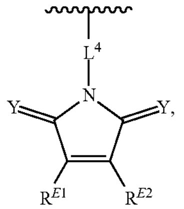
(i-9)
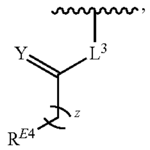
(i-10)
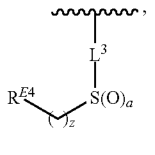
-continued
(i-11)
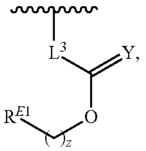
(i-12)
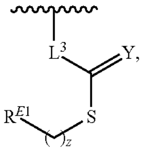
(i-13)
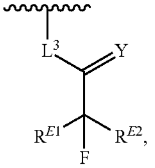
(i-14)
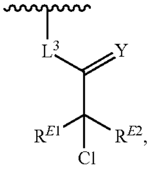
(i-15)
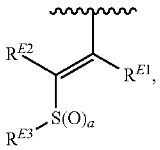
(i-16)
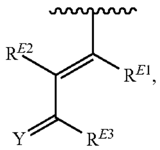
(i-17)
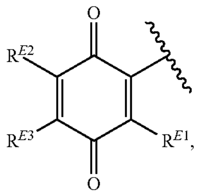
(i-18)
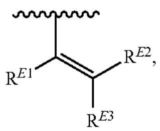
(i-19)
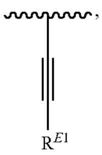

-continued
(i-20)
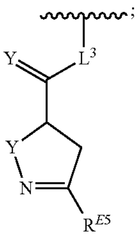
(i-21)
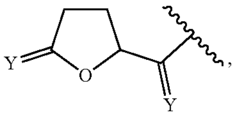
(i-22)
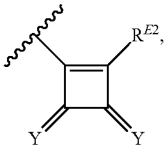
(i-23)
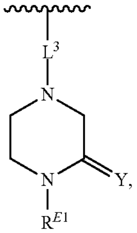
(i-24)
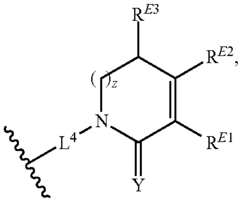
(i-25)
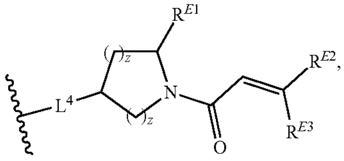
(i-26)
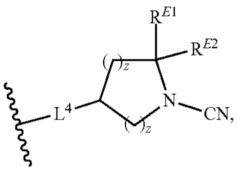
(i-27)
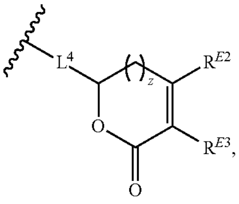
-continued
(i-28)
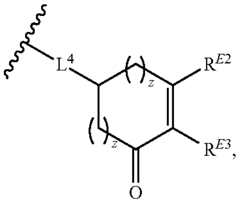
(i-29)
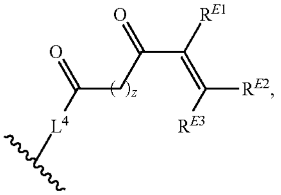
(i-30)
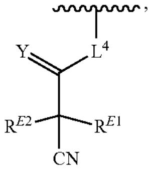
(i-31)
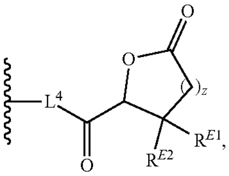
(i-32)
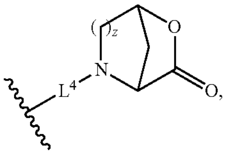
(i-33)
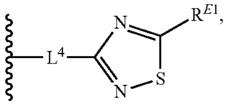
(i-34)
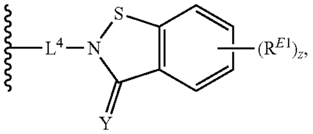
(i-35)
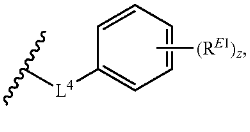
(i-36)
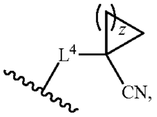
(i-37)
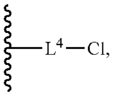

-continued (i-38)

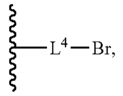

(i-39)

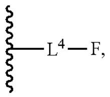

(i-40)

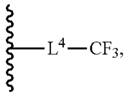

(i-41)

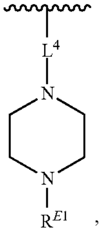

, and (i-42)

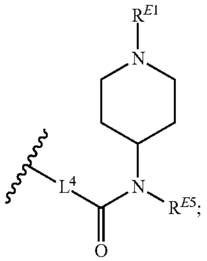

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}C(=O)$—, —$C(=O)NR^{L3a}$—, —SC(=O)—, —C(=O)S—, —OC(=O)—, —C(=O)O—, —$NR^{L3a}C(=S)$—, —$C(=S)NR^{L3a}$—, trans-$CR^{L3b}=CR^{L3b}$—, cis-$CR^{L3b}=CR^{L3b}$—, —C≡C—, —S(=O)—, —S(=O)O—, —OS(=O)—, —$S(=O)NR^{L3a}$, —$NR^{L3a}S(=O)$—, —$S(=O)_2$—, —$S(=O)_2O$—, —$OS(=O)_2$—, —$S(=O)_2NR^{L3a}$—, or —$NR^{L3a}S(=O)_2$—, wherein $R^{L3a}$ is hydrogen, substituted or unsubstituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L^4$ is a bond, or an optionally substituted $C_{1-4}$ hydrocarbon chain; $R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, and —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, and —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E3a}$, —$CH_2N(R^{E3a})_2$, —$CH_2SR^{E3a}$, —$OR^{E3a}$, —$N(R^{E3a})_2$, and —$SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or $NR^{E6}$, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

In certain embodiments, $D^1$ is a warhead of Formula (i-1) through (i-42). In certain embodiments, the warhead is of formula:

(i-1)

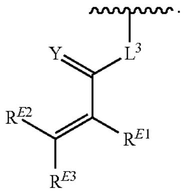

In certain embodiments, $D^1$ is a warhead of formula:

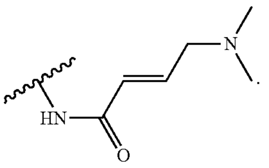 [SMILES: *NC(=O)/C=C/CN(C)C]

In certain embodiments, $D^1$ is a warhead of formula:

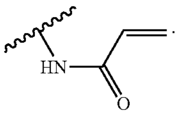 [SMILES: *NC(=O)C=C]

In certain embodiments, $D^1$ is a warhead of formula:

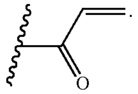 [SMILES: *C(=O)C=C]

In certain embodiments, $D^1$ is of formula:

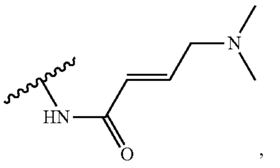

,

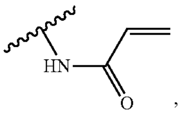

, or

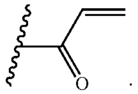

In certain embodiments, $L^3$ is a bond. In certain embodiments, $L^3$ is —NH—. In certain embodiments, $R^{E1}$ and $R^{E2}$ are hydrogen. In certain embodiments, $R^{E1}$, $R^{E2}$, and $R^{E3}$ are hydrogen. In certain embodiments, $R^{E3}$ is —$CH_2NMe_2$.

In certain embodiments, the warhead is of formula (i-2)

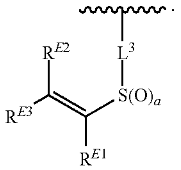

In certain embodiments, the warhead is of formula (i-3)

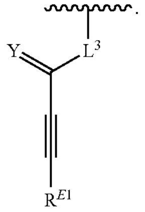

In certain embodiments, the warhead is of formula (i-4)

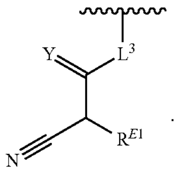

In certain embodiments, the warhead is of formula (i-5)

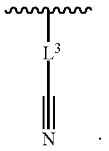

In certain embodiments, the warhead is of formula (i-6)

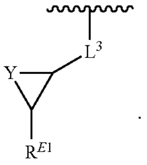

In certain embodiments, the warhead is of formula

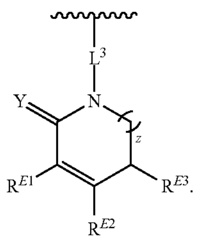

(i-7)

In certain embodiments, the warhead is of formula

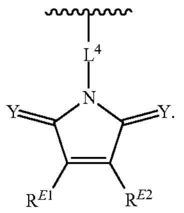

(i-8)

In certain embodiments, the warhead is of formula:

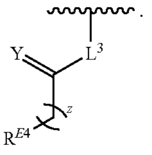

(i-9)

9). In certain embodiments, the warhead is of formula;

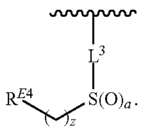

(i-10)

In certain embodiments, the warhead is of formula:

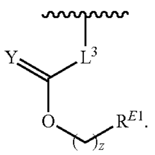

(i-11)

In certain embodiments, the warhead is of formula

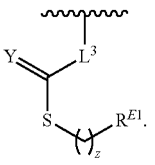

(i-12)

In certain embodiments, the warhead is of formula

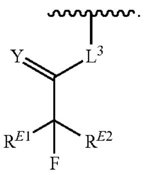

(i-13)

In certain embodiments, the warhead is of formula

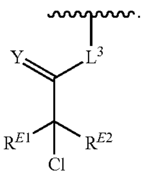

(i-14)

In certain embodiments, the warhead is of formula

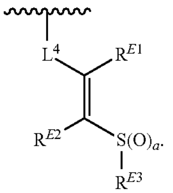

(i-15)

In certain embodiments, the warhead is of formula

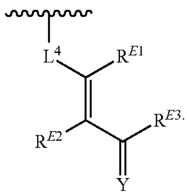

(i-16)

In certain embodiments, the warhead is of formula (i-17)

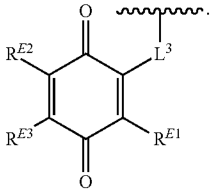

In certain embodiments, the warhead is of formula (i-18)

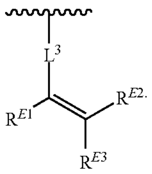

In certain embodiments, the warhead is of formula (i-19)

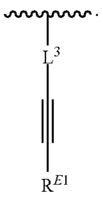

In certain embodiments, the warhead is of formula (i-20)

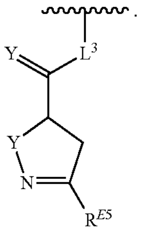

In certain embodiments, the warhead is (i-21)

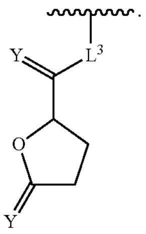

In certain embodiments, the warhead is of formula (i-22)

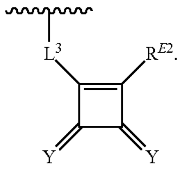

In certain embodiments, the warhead is of formula (i-23)

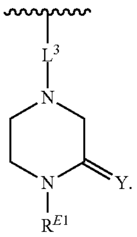

In certain embodiments, the warhead is of formula (i-24)

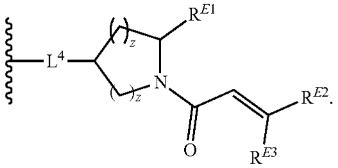

In certain embodiments, the warhead is of formula (i-25)

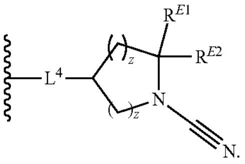

In certain embodiments, the warhead is of formula (i-26)

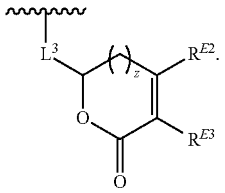

In certain embodiments, the warhead is of formula

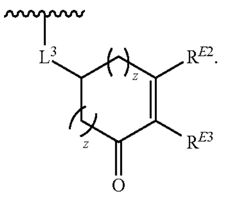

(i-27)

In certain embodiments, the warhead is of formula

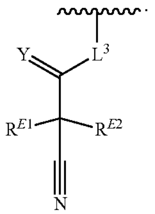

(i-28)

(i-28). In certain embodiments, the warhead is of formula

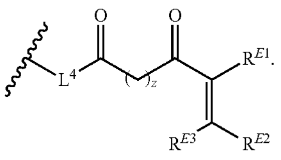

(i-29)

In certain embodiments, the warhead is of formula

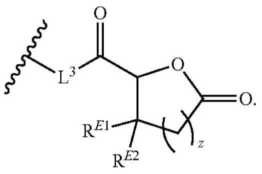

(i-30)

In certain embodiments, the warhead is of formula

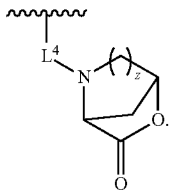

(i-31)

In certain embodiments, the warhead is of formula

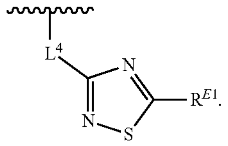

(i-32)

In certain embodiments, the warhead is of formula

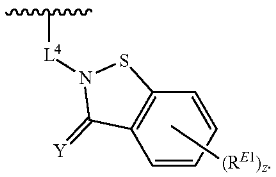

(i-33)

In certain embodiments, the warhead is of formula

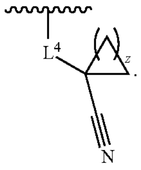

(i-34)

In certain embodiments, the warhead is of formula

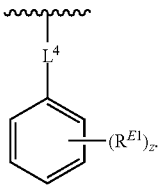

(i-35)

In certain embodiments, the warhead is of formula

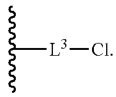

(i-36)

In certain embodiments, the warhead is of formula

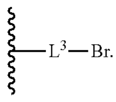

(i-37)

In certain embodiments, the warhead is of formula (i-38)

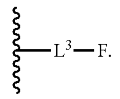

In certain embodiments, the warhead is of formula (i-39)

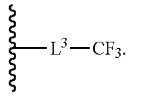

39). In certain embodiments, the warhead is of formula (i-40)

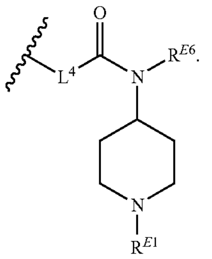

In certain embodiments, the warhead is of formula (i-41)

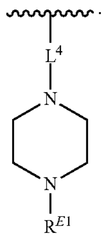

In certain embodiments, the warhead is of formula (i-42)

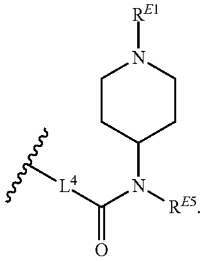

In certain embodiments, the warhead is of the formula,

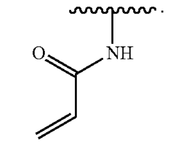

In certain embodiments, the warhead is of the formula,

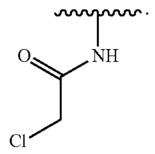 [SMILES: *NC(=O)CCl]

In certain embodiments, $L^3$ is a bond (e.g., a single bond, a double bond, or a triple bond). In certain embodiments, $L^3$ is a single bond. In certain embodiments, $L^3$ is a double bond. In certain embodiments, $L^3$ is a triple bond. In certain embodiments, $L^3$ is an optionally substituted $C_{1-4}$ hydrocarbon chain, optionally wherein one or more carbon units of the hydrocarbon chain are independently replaced with —C═O—, —O—, —S—, —NR$^{L3a}$—, —NR$^{L3a}$C(═O)—, —C(═O)NR$^{L3a}$—, —SC(═O)—, —C(═O)S—, —OC(═O)—, —C(═O)O—, —NR$^{L3a}$C(═S)—, —C(═S)NR$^{L3a}$—, trans-CR$^{L3b}$═CR$^{L3b}$—, cis-CR$^{L3b}$═CR$^{L3b}$, —C≡C—, —S(═O)—, —S(═O)O—, —OS(═O)—, —S(═O)NR$^{L3a}$, —NR$^{L3a}$S(═O)—, —S(═O)$_2$—, —S(═O)$_2$O—, —OS(═O)$_2$—, —S(═O)$_2$NR$^{L3a}$—, or —NR$^{L3a}$S(═O)$_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring. In certain embodiments, $L^4$ is a bond (e.g., a single bond, a double bond, or a triple bond). In certain embodiments, $L^4$ is an optionally substituted branched $C_{1-6}$ hydrocarbon chain (e.g., i-Pr). In certain embodiments, $L^4$ is an optionally substituted unbranched $C_{1-6}$ hydrocarbon chain (e.g., n-Pr, or n-Bu). In certain embodiments, at least one instance of $R^{E1}$ is H. In certain embodiments, at least one instance of $R^{E1}$ is halogen (e.g., F, Cl, Br, or I). In certain embodiments, at least one instance of $R^{E1}$ is optionally substituted alkyl (e.g., Me, or Et). In certain embodiments, at least one instance of $R^{E1}$ is optionally substituted alkenyl (e.g., optionally substituted vinyl). In certain embodiments, at least one instance of $R^{E1}$ is optionally substituted alkynyl. In certain embodiments, at least one instance of $R^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E1}$ is substituted or unsubstituted aryl (e.g., substituted or unsubstituted, 6- to 10-membered aryl). In certain embodiments, at least one instance of $R^{E1}$ is substituted or unsubstituted phenyl. In certain embodiments, at least one instance of $R^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E1}$ is —CN. In certain embodiments, at least one instance of $R^{E1}$ is —$CH_2OR^{EE}$, wherein each instance of $R^{E}$E is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E1}$ is —$CH_2N(R^{EF})_2$ or —$N(R^{EF})_2$, wherein each instance of $R^{E}$F is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E1}$ is —$CH_2SR^{EE}$ or —$SR^{EE}$ (e.g., —$CH_2SMe$ or —SMe). In certain embodiments, at least one instance of $R^{E1}$ is —$OR^{EE}$ (e.g., —OMe). In certain embodiments, at least one instance of $R^{E1}$ is —$Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$).

In certain embodiments, at least one instance of $R^{E2}$ is H. In certain embodiments, at least one instance of $R^{E2}$ is halogen (e.g., F, Cl, Br, or I). In certain embodiments, at least one instance of $R^{E2}$ is optionally substituted alkyl (e.g., Me, or Et). In certain embodiments, at least one instance of $R^{E2}$ is optionally substituted alkenyl (e.g., optionally substituted vinyl). In certain embodiments, at least one instance of $R^{E2}$ is optionally substituted alkynyl. In certain embodiments, at least one instance of $R^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E2}$ is —CN. In certain embodiments, at least one instance of $R^{E2}$ is —$CH_2OR^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E2}$ is —$CH_2N(R^{EF})_2$ or —$N(R^{EF})_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E2}$ is —$CH_2SR^{EE}$ or —$SR^{EE}$ (e.g., —$CH_2SMe$ or —SMe). In certain embodiments, at least one instance of $R^{E2}$ is —$OR^{EE}$ (e.g., —OMe). In certain embodiments, at least one instance of $R^{E2}$ is —$Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$). In certain embodiments, at least one instance of $R^{E3}$ is H. In certain embodiments, at least one instance of $R^{E3}$ is halogen (e.g., F, Cl, Br, or I). In certain embodiments, at least one instance of $R^{E3}$ is optionally substituted alkyl (e.g., Me, or Et). In certain embodiments, at least one instance of $R^{E3}$ is optionally substituted alkenyl (e.g., optionally substituted vinyl). In certain embodiments, at least one instance of $R^{E3}$ is optionally substituted alkynyl. In certain embodiments, at least one instance of $R^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E3}$ is —CN. In certain embodiments, at least one instance of $R^{E3}$ is —$CH_2OR^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E3}$ is —$CH_2N(R^{EF})_2$ or —$N(R^{EF})_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E3}$ is —$CH_2SR^{EE}$ or —$SR^{EE}$ (e.g., —$CH_2SMe$ or —SMe). In certain embodiments, at least one instance of $R^{E3}$ is —$OR^{EE}$ (e.g., —OMe). In certain embodiments, at least one instance of $R^{E3}$ is —$Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$). In certain embodiments, $R^{E1}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E2}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E2}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E1}$ and $R^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E4}$ is a leaving group (e.g., halogen, or a sulfonic acid ester, e.g., —O(tosylate) or —O(mesylate)). In certain embodiments, $R^{E5}$ is halogen (e.g., F, Cl, Br, or I). In certain embodiments, $R^{E6}$ is H. In certain embodiments, $R^{E6}$ is substituted or unsubstituted $C_{1-6}$ alkyl (e.g., Me, is —$CF_3$, Bn, Et, perfluoroethyl, Pr, perfluoropropyl, Bu, or perfluorobutyl). In certain embodiments, $R^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is $NR^{E7}$, wherein $R^{E7}$ is hydrogen, substituted or unsubstituted $C_{1-6}$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

In certain embodiments, the compound of Formula (I) is of the formula:

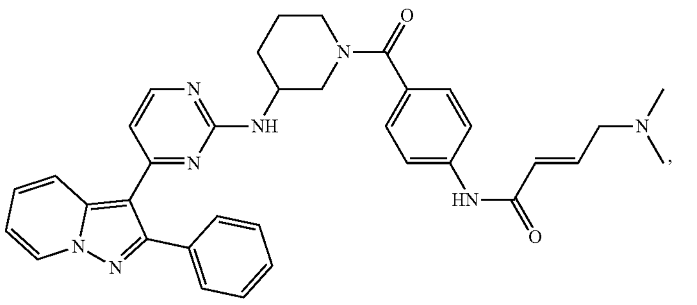

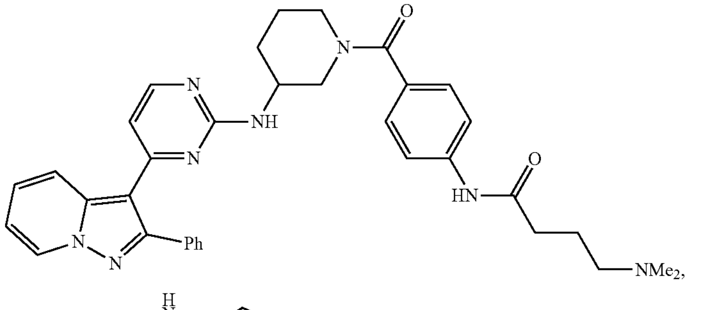

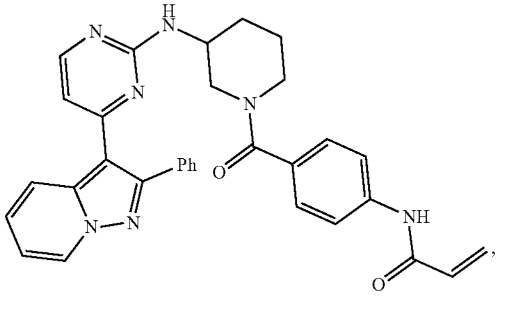

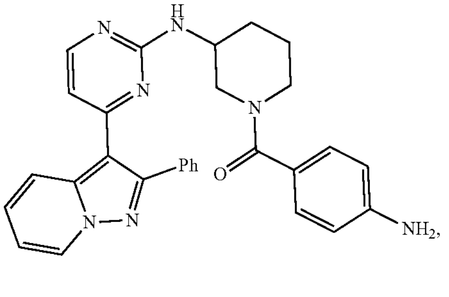

-continued
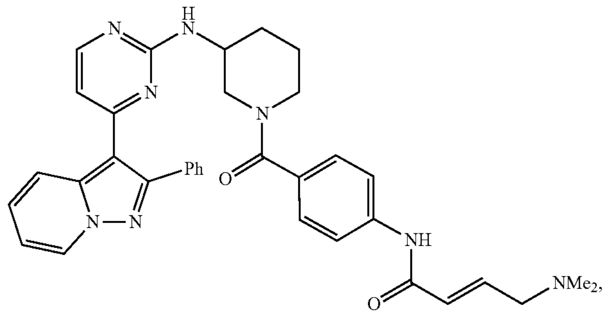
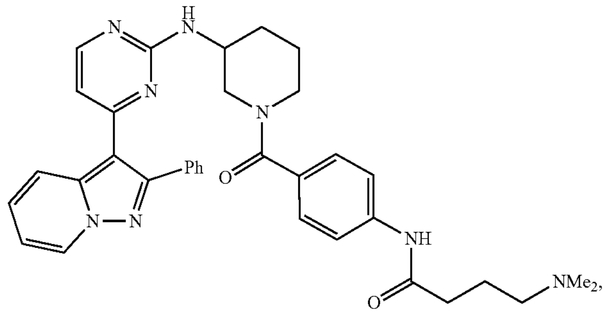
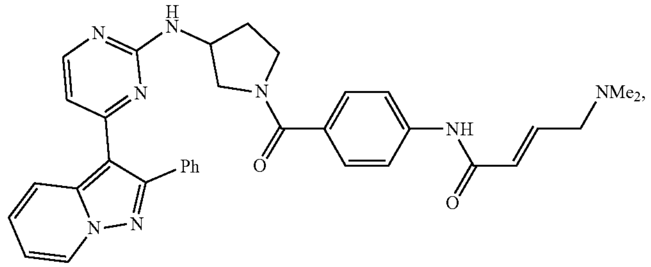
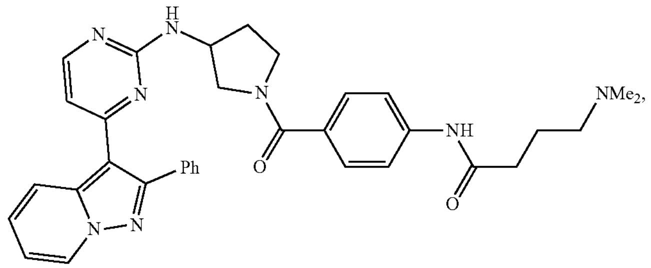
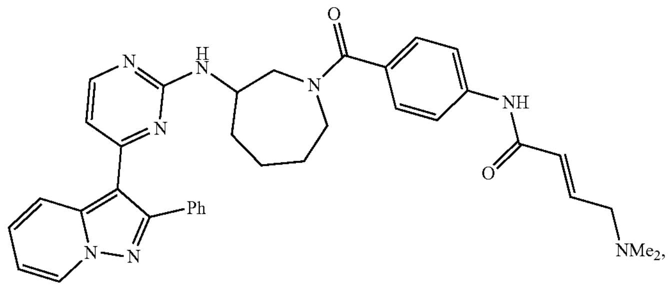

-continued
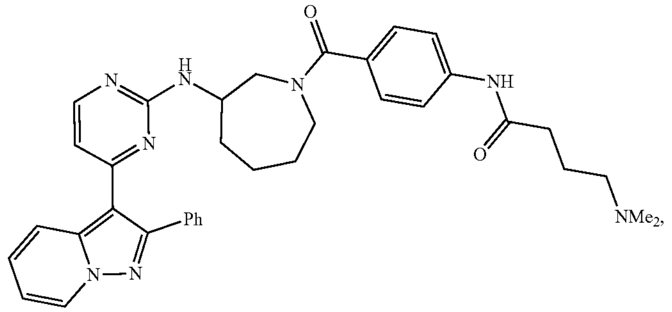
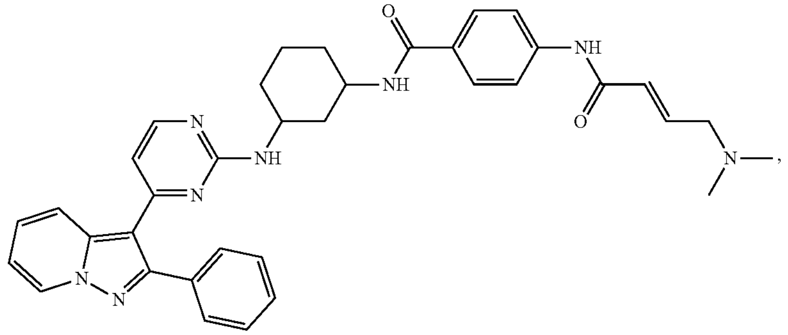
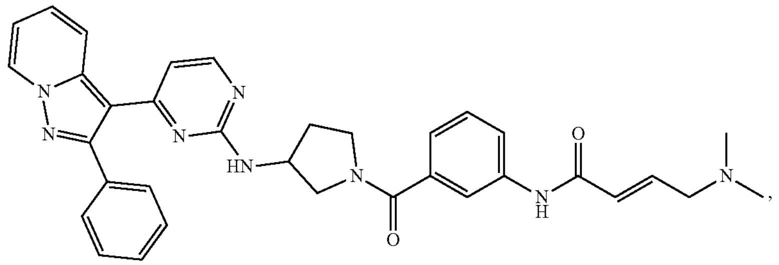
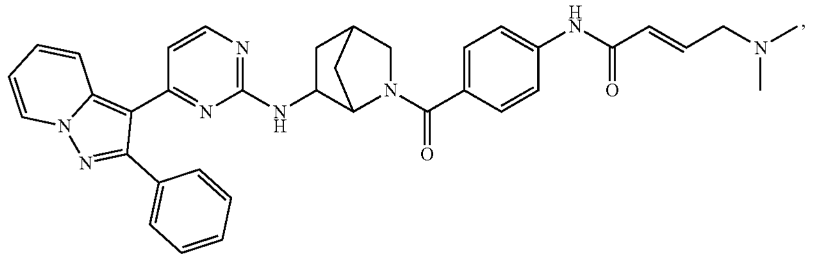
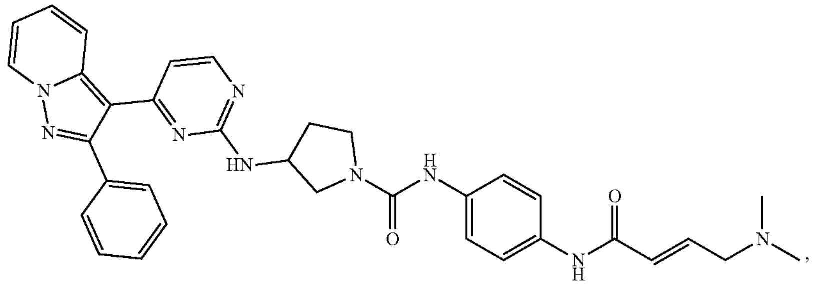
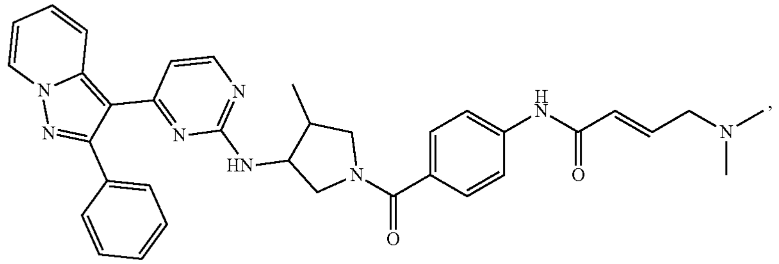

-continued
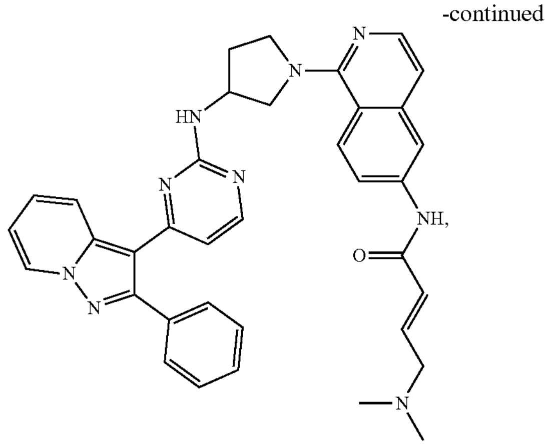
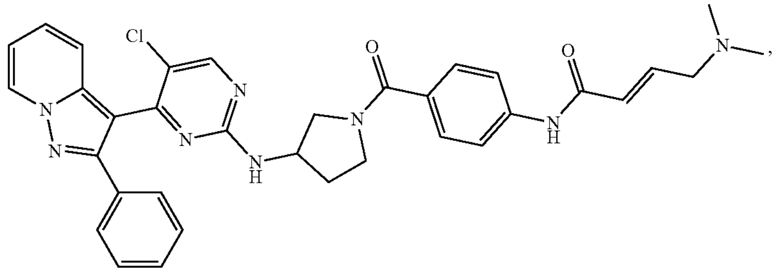
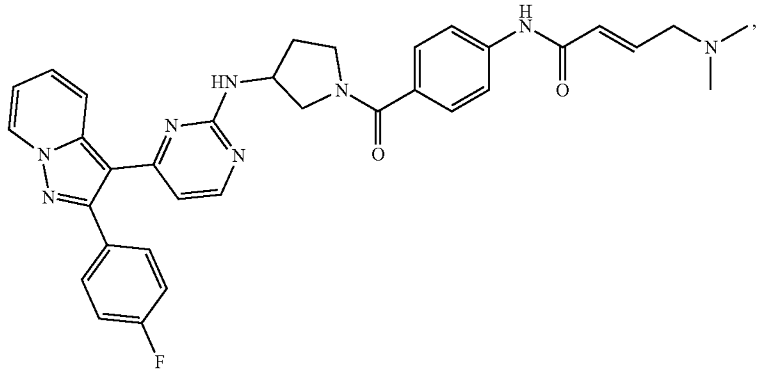
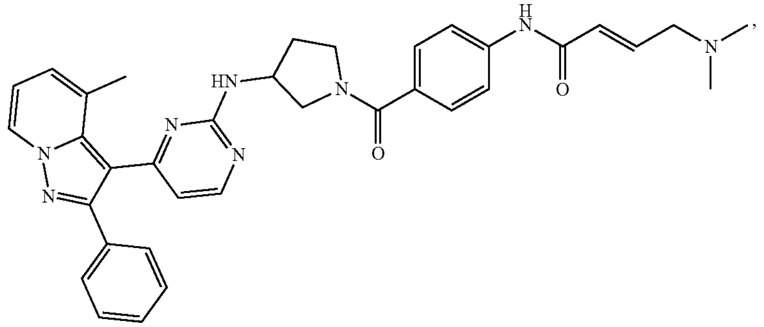
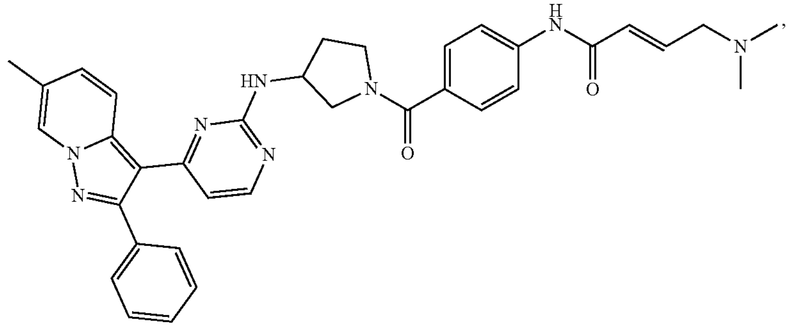

-continued

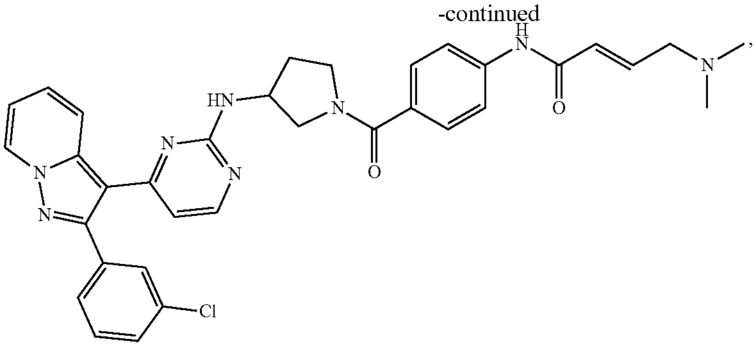

,

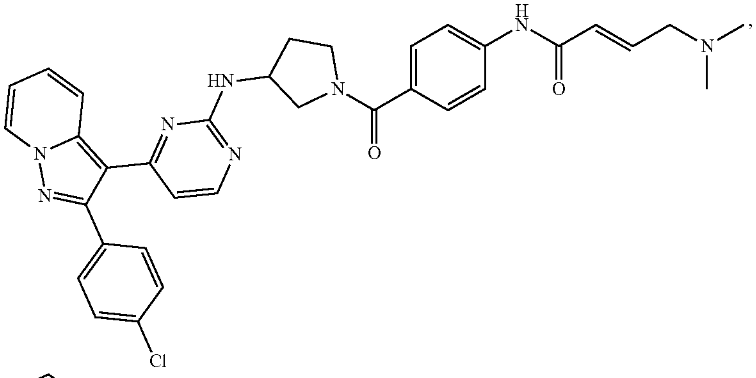

,

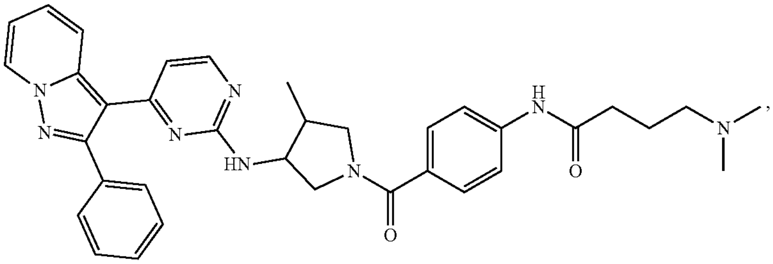

,

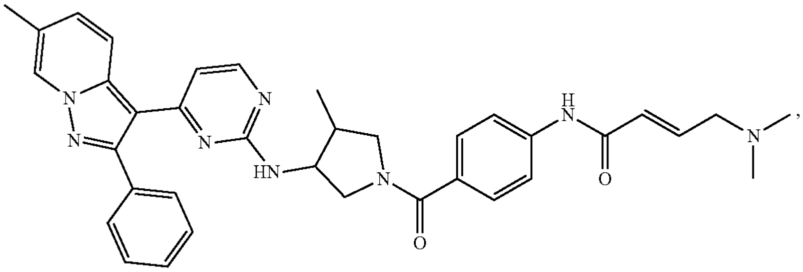

,

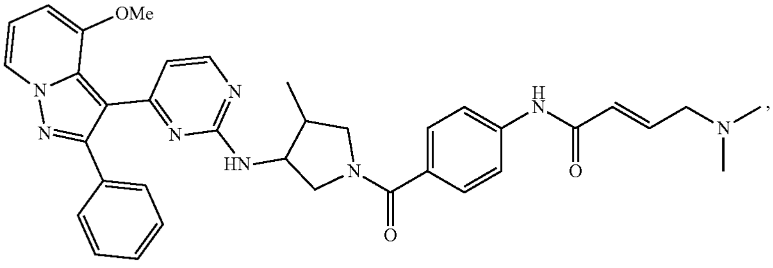

, or a pharmaceutically acceptable salts, solvates, hydrates, polymorphs, co-crystals, tautomers, stereoisomers, isotopologue, and prodrugs thereof.

In certain embodiments, a compound described herein is a compound of Formula (I), or a pharmaceutically acceptable salt, solvate, hydrate, polymorph, co-derivative, crystal, tautomer, stereoisomer, isotopologue, or prodrug thereof. In certain embodiments, a compound described herein is a compound of Formula (I), or a pharmaceutically acceptable salt thereof.

Methods of Treatment and Uses

The present disclosure provides methods of modulating (e.g., inhibiting or increasing) the activity (e.g., aberrant activity, or undesired activity, such as increased or decreased activity) of a kinase (e.g., JNK (e.g., JNK2)). The present disclosure provides methods of modulating (e.g., inhibiting or increasing) the activity (e.g., aberrant activity, such as increased or decreased activity) of a JNK (e.g., JNK2) in a subject, biological sample, tissue, or cell. The present disclosure also provides methods for the treatment of a wide range of diseases, such as diseases associated with the aberrant activity (e.g., increased activity) of a kinase, e.g., proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell. The present disclosure provides methods for the treatment and/or prevention of a proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell.

The present disclosure further provides methods of using the compounds described herein, e.g., as biological probes to study the inhibition of the activity of a kinase (e.g., JNK (e.g., JNK2)), and as therapeutics, e.g., in the treatment and/or prevention of diseases associated with the overexpression and/or aberrant activity of the kinase (e.g., JNK (e.g., JNK2)). In certain embodiments, the compounds covalently inhibit JNKs (e.g., JNK2). In certain embodiments, the diseases treated and/or prevented include, but are not limited to, proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell. In certain embodiments, the cancer is associated with the overexpression and/or aberrant activity of a kinase (e.g., JNK (e.g., JNK2)). Also provided by the present disclosure are pharmaceutical compositions, kits, methods, and uses of a compound of Formula (I) as described herein.

Certain compounds described herein bind, covalently modify, and/or inhibit a kinase. In certain embodiments, the compounds described herein irreversibly inhibit a kinase. In certain embodiments, the kinase is a JNK. In certain embodiments, the kinase is JNK2. In certain embodiments, the compounds described herein covalently bind to the kinase (e.g., JNK (e.g., JNK2)). In certain embodiments, the compounds described herein non-reversibly bind to the kinase (e.g., JNK (e.g., JNK2)). In certain embodiments, the compounds described herein modulate the activity of a kinase (e.g., JNK (e.g., JNK1, JNK2, JNK3)). In certain embodiments, the compounds described herein inhibit the activity of a kinase (e.g., a JNK (e.g., JNK2)). In certain embodiments, the compounds described herein irreversibly inhibit the activity of a kinase (e.g., JNK (e.g., JNK2)).

The binding affinity of a compound described herein to a kinase (e.g., JNK (e.g., JNK2)) may be measured by the dissociation constant ($K_d$) value of an adduct of the compound and the kinase (e.g., JNK (e.g., JNK2)) using methods known in the art (e.g., isothermal titration calorimetry (ITC)). In certain embodiments, the $K_d$ value of the adduct is not more than about 100 μM, not more than about 10 μM, not more than about 1 μM, not more than about 100 nM, not more than about 10 nM, or not more than about 1 nM.

In certain embodiments, the activity of a kinase (e.g., JNK (e.g., JNK2)) is inhibited by a compound described herein. The inhibition of the activity of a kinase (e.g., JNK (e.g., JNK2)) by a compound described herein may be measured by determining the half maximal inhibitory concentration ($IC_{50}$) of the compound when the compound, or a pharmaceutical composition thereof, is contacted with the kinase (e.g., JNK (e.g., JNK2)). The $IC_{50}$ values may be obtained using methods known in the art (e.g., by a competition binding assay). In certain embodiments, the $IC_{50}$ value of a compound described herein is not more than about 1 mM, not more than about 100 μM, not more than about 10 μM, not more than about 1 μM, not more than about 100 nM, not more than about 10 nM, or not more than about 1 nM.

In some embodiments, the activity of the kinase being inhibited is selectively inhibited by the compounds or pharmaceutical compositions described herein, compared to the activity of a different protein (e.g., a different kinase). In certain embodiments, the activity of a JNK (e.g., JNK2) is selectively inhibited by a compound or pharmaceutical composition described herein, compared to the activity of a different protein (e.g., a different kinase). In certain embodiments, the activity of JNK2 is selectively inhibited by a compound or pharmaceutical composition described herein, compared to the activity of another JNK (e.g., JNK1 or JNK3).

The selectivity of a compound or pharmaceutical composition described herein in inhibiting the activity of a kinase over a different protein (e.g., a different kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the kinase. The selectivity of a compound or pharmaceutical composition described herein for a kinase over a different protein may also be measured by the quotient of the $K_d$ value of an adduct of the compound or pharmaceutical composition and the different protein over the $K_d$ value of an adduct of the compound or pharmaceutical composition and the kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

The compounds described herein may selectively modulate the activity of a kinase (e.g., JNK (e.g., JNK2)). In certain embodiments, the compounds selectively increase the activity of a kinase (e.g., JNK (e.g., JNK2)) In certain embodiments, the compounds selectively inhibit the activity of a kinase (e.g., JNK (e.g., JNK2)). In certain embodiments, the compounds inhibit the activity of two or more kinases (e.g., JNK (e.g., JNK1, JNK2, JNK3)) to some extent.

In certain embodiments, the present disclosure provides selective inhibitors of a kinase (e.g., JNK (e.g., JNK2). In certain embodiments, the inventive compounds selectively inhibit the activity of a JNK (e.g., JNK2). The selectivity of a compound described herein for inhibiting the activity of a first kinase (e.g., JNK (e.g., JNK2)) over a second kinase (e.g., JNK (e.g., JNK1, JNK3)) may be measured by the quotient of the $IC_{50}$ value of the compound in inhibiting the activity of the second kinase (e.g., JNK (e.g., JNK1, JNK3) over the $IC_{50}$ value of the compound in inhibiting the activity of the first kinase (e.g., JNK (e.g., JNK2). The selectivity of a compound described herein in modulating the activity of a first kinase (e.g., JNK (e.g., JNK2) over a second kinase (e.g., JNK (e.g., JNK1, JNK3)) may also be measured by the quotient of the $K_d$ value of an adduct of the compound and the second JNK (e.g., JNK1, JNK3) over the $K_d$ value of an adduct of the compound and the first JNK (e.g., JNK2). In certain embodiments, the selectivity is at least about 1-fold, at least about 3-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold.

Table 1 shows the results of an $IC_{50}$ assay for JNK kinase inhibition for JNK1, JNK2, and JNK3 with exemplary compounds of the disclosure.
TABLE 1
$IC_{50}$ assay with exemplary compounds
| Structure | ID | JNK1 (nM) | JNK2 (nM) | JNK3 (nM) |
|---|---|---|---|---|
| 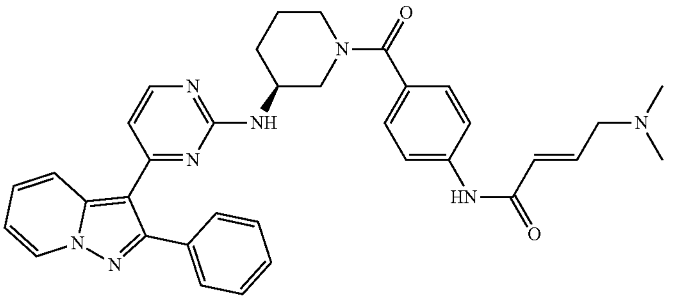 [SMILES: CN(C)C/C=C/C(=O)Nc1ccc(C(=O)N2CCC[C@H](Nc3nccc(-c4c(-c5ccccc5)nn5ccccc45)n3)C2)cc1] | I-1 | 44.7 | 3.65 | 2.36 |
| 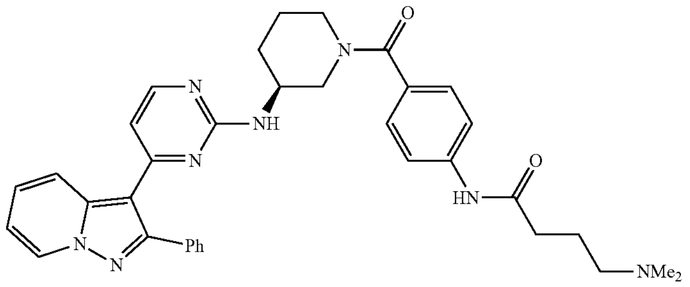 [SMILES: CN(C)CCCC(=O)Nc1ccc(C(=O)N2CCC[C@H](Nc3nccc(-c4c(-c5ccccc5)nn5ccccc45)n3)C2)cc1] | I-2 | 64 | 11 | 20 |
| 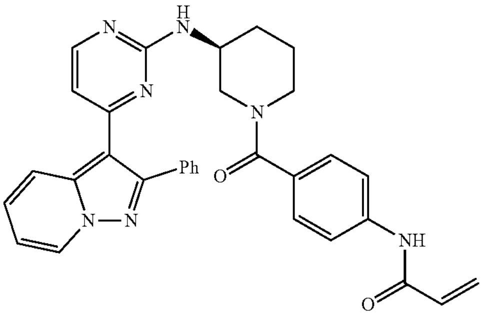 [SMILES: C=CC(=O)Nc1ccc(C(=O)N2CCC[C@H](Nc3nccc(-c4c(-c5ccccc5)nn5ccccc45)n3)C2)cc1] | I-3 | 26 | 5.67 | 16.2 |
| 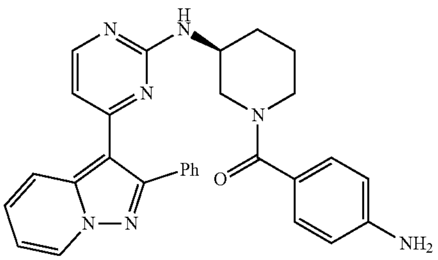 [SMILES: Nc1ccc(C(=O)N2CCC[C@H](Nc3nccc(-c4c(-c5ccccc5)nn5ccccc45)n3)C2)cc1] | I-4 | 21.4 | 2.88 | 22.5 |

TABLE 1-continued
| IC50 assay with exemplary compounds | | | | |
|---|---|---|---|---|
| Structure | ID | JNK1 (nM) | JNK2 (nM) | JNK3 (nM) |
| 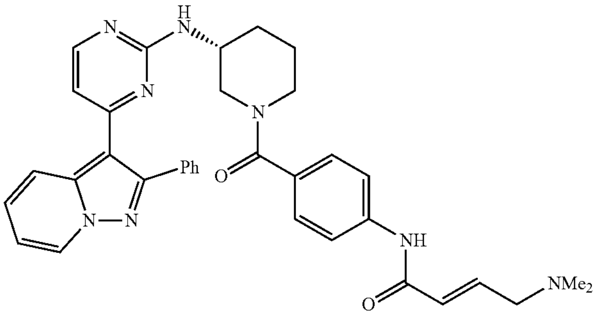 [SMILES: CN(C)C/C=C/C(=O)Nc1ccc(C(=O)N2CCC[C@@H](Nc3nccc(-c4c(-c5ccccc5)nn5ccccc45)n3)C2)cc1] | I-5 | 569 | 24 | 15 |
| 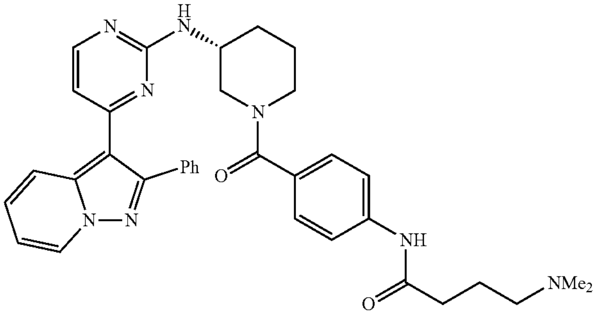 [SMILES: CN(C)CCCC(=O)Nc1ccc(C(=O)N2CCC[C@@H](Nc3nccc(-c4c(-c5ccccc5)nn5ccccc45)n3)C2)cc1] | I-6 | 278 | 40 | 1090 |
| 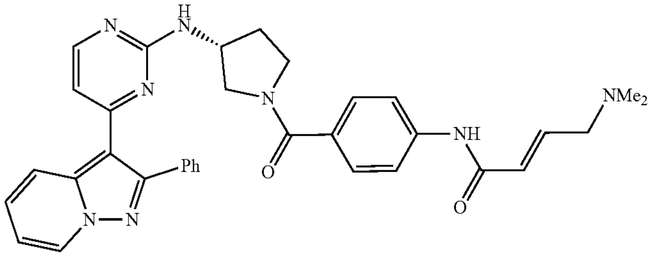 [SMILES: CN(C)C/C=C/C(=O)Nc1ccc(C(=O)N2CC[C@@H](Nc3nccc(-c4c(-c5ccccc5)nn5ccccc45)n3)C2)cc1] | I-7 | 12.5 | 2.75 | 25 |
| 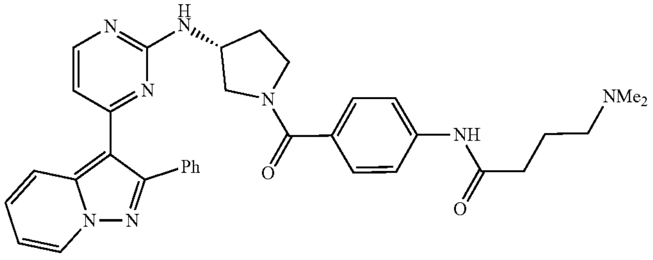 [SMILES: CN(C)CCCC(=O)Nc1ccc(C(=O)N2CC[C@@H](Nc3nccc(-c4c(-c5ccccc5)nn5ccccc45)n3)C2)cc1] | I-8 | 73.4 | 5.59 | 21.4 |
| 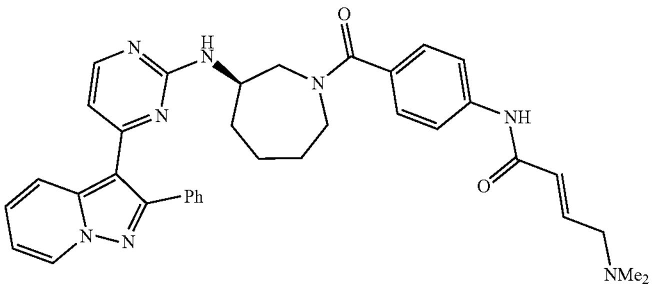 [SMILES: CN(C)C/C=C/C(=O)Nc1ccc(C(=O)N2CCCC[C@@H](Nc3nccc(-c4c(-c5ccccc5)nn5ccccc45)n3)C2)cc1] | I-9 | 403 | 15.9 | 96.1 |

TABLE 1-continued
| IC$_{50}$ assay with exemplary compounds | | | | |
|---|---|---|---|---|
| Structure | ID | JNK1 (nM) | JNK2 (nM) | JNK3 (nM) |
| 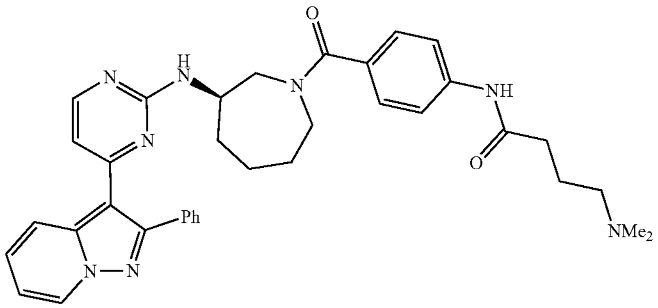 [SMILES: CN(C)CCCC(=O)Nc1ccc(C(=O)N2CCCC[C@@H](Nc3nccc(-c4c(-c5ccccc5)nn5ccccc45)n3)C2)cc1] | I-10 | 243 | 7.88 | 48.1 |
| 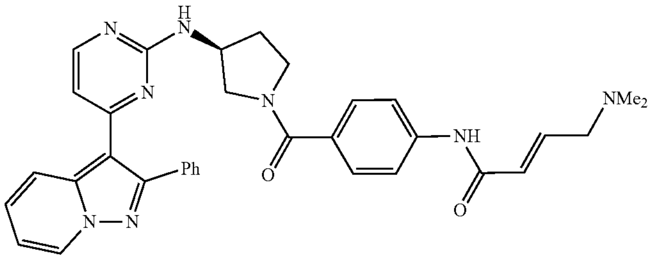 [SMILES: CN(C)C/C=C/C(=O)Nc1ccc(C(=O)N2CC[C@H](Nc3nccc(-c4c(-c5ccccc5)nn5ccccc45)n3)C2)cc1] | I-11 | 152 | 4.91 | 51.4 |
| 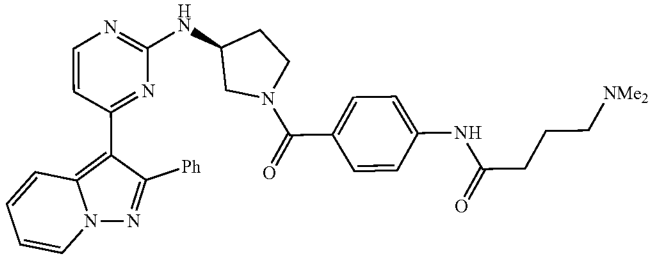 [SMILES: CN(C)CCCC(=O)Nc1ccc(C(=O)N2CC[C@H](Nc3nccc(-c4c(-c5ccccc5)nn5ccccc45)n3)C2)cc1] | I-12 | 320 | 17.6 | 110 |
| 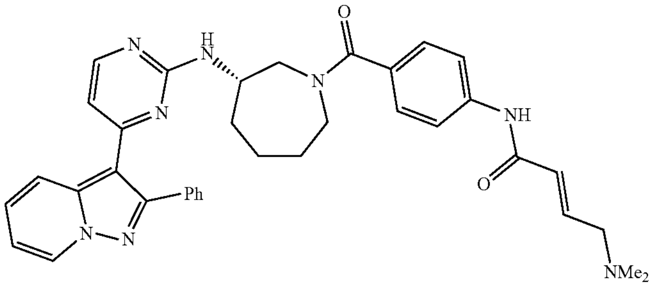 [SMILES: CN(C)C/C=C/C(=O)Nc1ccc(C(=O)N2CCCC[C@H](Nc3nccc(-c4c(-c5ccccc5)nn5ccccc45)n3)C2)cc1] | I-13 | 308 | 31 | 20 |
| 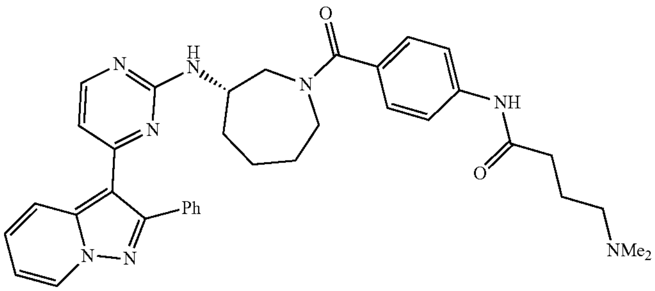 [SMILES: CN(C)CCCC(=O)Nc1ccc(C(=O)N2CCCC[C@H](Nc3nccc(-c4c(-c5ccccc5)nn5ccccc45)n3)C2)cc1] | I-14 | 314 | 29 | 252 |

TABLE 1-continued
| IC$_{50}$ assay with exemplary compounds | | | | |
|---|---|---|---|---|
| Structure | ID | JNK1 (nM) | JNK2 (nM) | JNK3 (nM) |
| 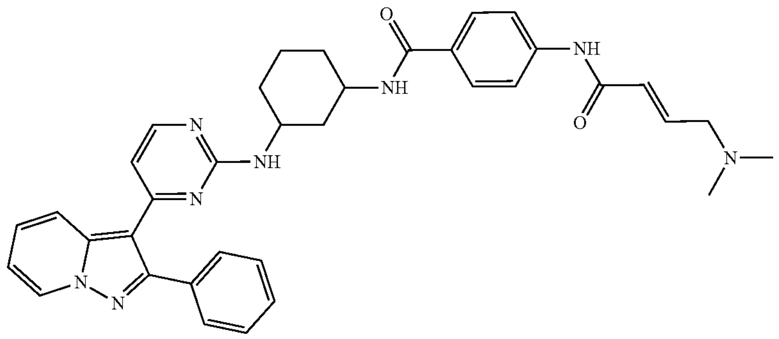 [SMILES: CN(C)C/C=C/C(=O)Nc1ccc(C(=O)NC2CCCC(Nc3nccc(-c4c(-c5ccccc5)nn5ccccc45)n3)C2)cc1] | I-15 | 481 | 38.9 | 40.3 |
| 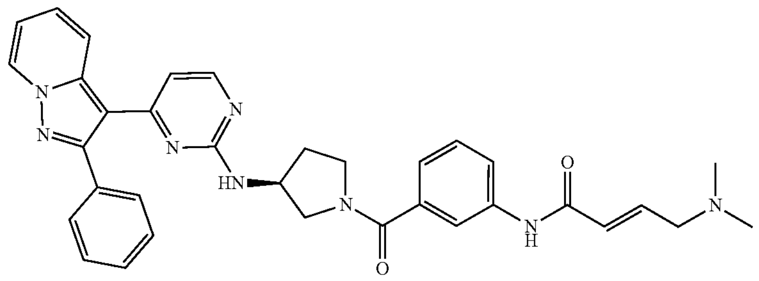 [SMILES: CN(C)C/C=C/C(=O)Nc1cccc(C(=O)N2CC[C@H](Nc3nccc(-c4c(-c5ccccc5)nn5ccccc45)n3)C2)c1] | I-16 | 37.6 | 6.94 | 10.9 |
| 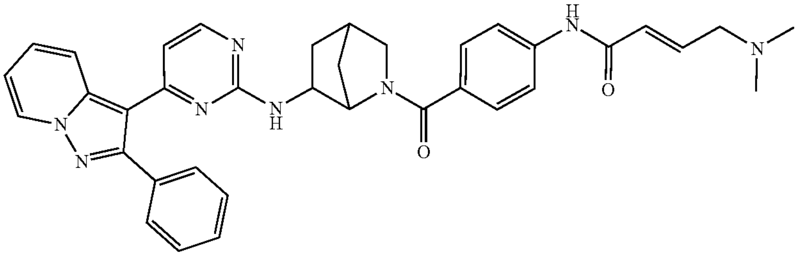 [SMILES: CN(C)C/C=C/C(=O)Nc1ccc(C(=O)N2CC3CC(Nc4nccc(-c5c(-c6ccccc6)nn6ccccc56)n4)C2C3)cc1] | I-17 | >10000 | 7890 | >10000 |
| 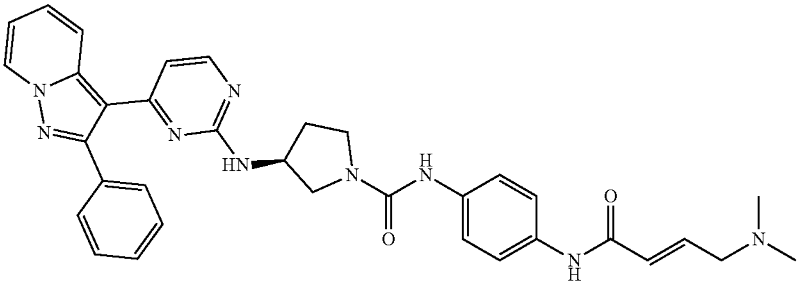 [SMILES: CN(C)C/C=C/C(=O)Nc1ccc(NC(=O)N2CC[C@H](Nc3nccc(-c4c(-c5ccccc5)nn5ccccc45)n3)C2)cc1] | I-18 | 99.3 | 12.4 | 15.7 |
| 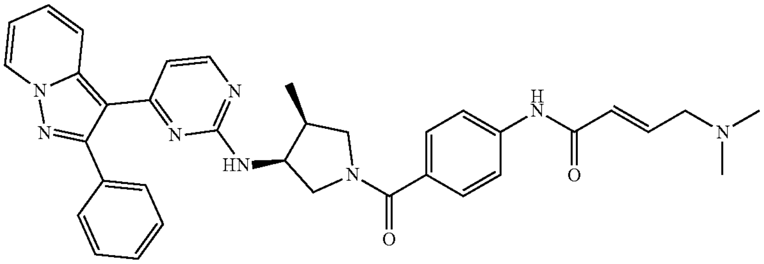 [SMILES: C[C@H]1CN(C(=O)c2ccc(NC(=O)/C=C/CN(C)C)cc2)C[C@H]1Nc1nccc(-c2c(-c3ccccc3)nn3ccccc23)n1] | I-19 | 2080 | 71 | 82.1 |

TABLE 1-continued
| IC$_{50}$ assay with exemplary compounds | | | | |
|---|---|---|---|---|
| Structure | ID | JNK1 (nM) | JNK2 (nM) | JNK3 (nM) |
| 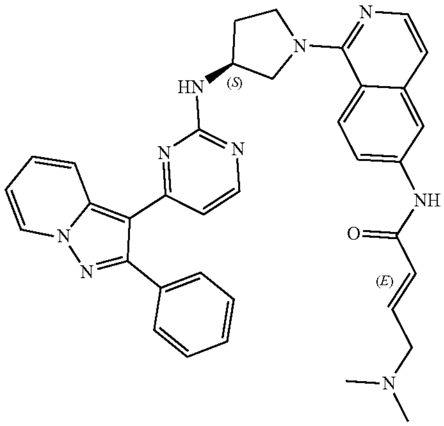 | I-20 | 168 | 10 | 12 |
| 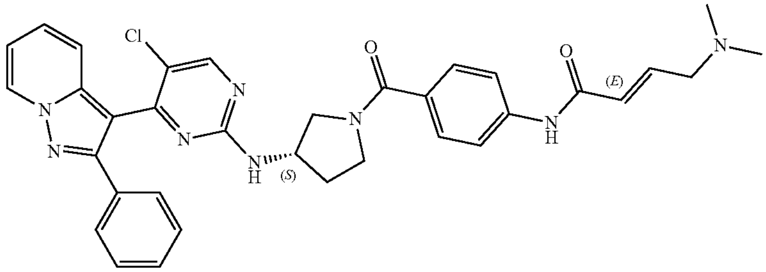 | I-21 | 3360 | 585 | 359 |
| 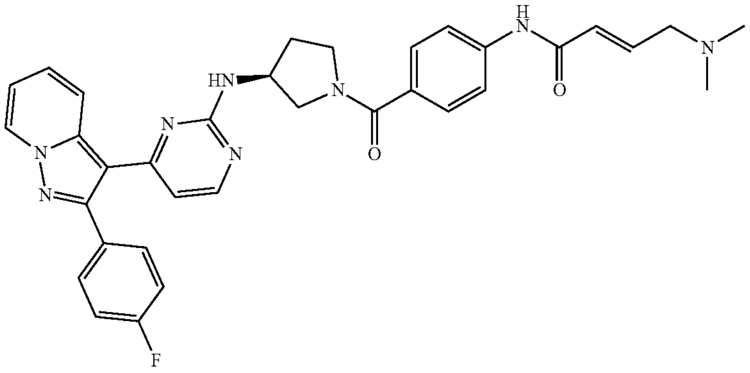 [SMILES: CN(C)C/C=C/C(=O)Nc1ccc(C(=O)N2CC[C@H](Nc3nccc(-c4c(-c5ccc(F)cc5)nn5ccccc45)n3)C2)cc1] | I-22 | 85 | 5.57 | 3.87 |
| 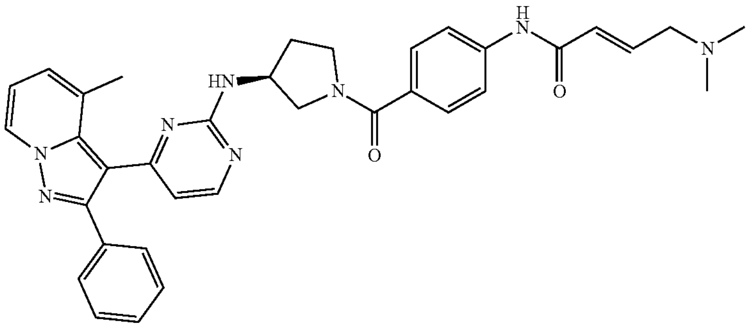 [SMILES: Cc1cccn2nc(-c3ccccc3)c(-c3ccnc(N[C@H]4CCN(C(=O)c5ccc(NC(=O)/C=C/CN(C)C)cc5)C4)n3)c12] | I-23 | 1140 | 142 | 396 |

TABLE 1-continued
IC$_{50}$ assay with exemplary compounds
| Structure | ID | JNK1 (nM) | JNK2 (nM) | JNK3 (nM) |
|---|---|---|---|---|
| 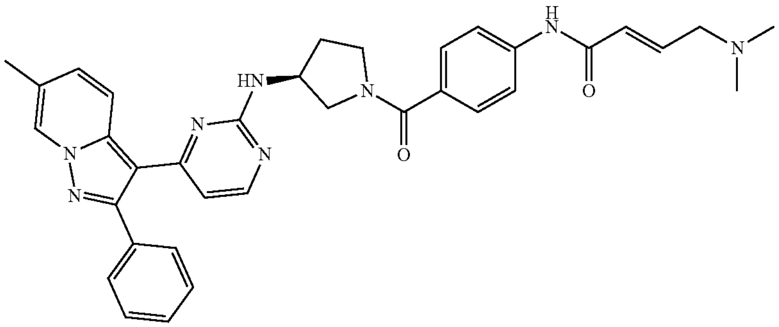 | I-24 | 18.4 | 0.952 | 5.53 |
| 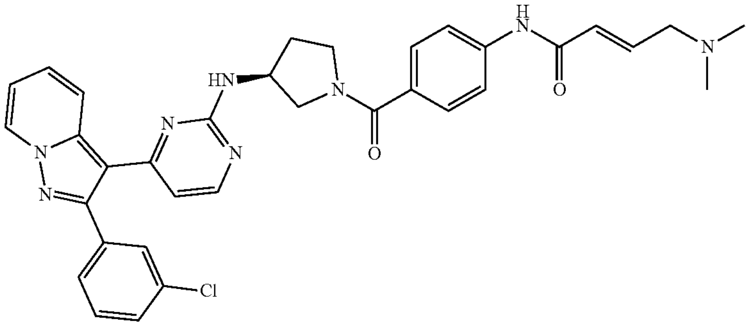 [SMILES: CN(C)C/C=C/C(=O)Nc1ccc(C(=O)N2CC[C@H](Nc3nccc(-c4c(-c5cccc(Cl)c5)nn5ccccc45)n3)C2)cc1] | I-25 | 90.7 | 3.92 | 18.3 |
| 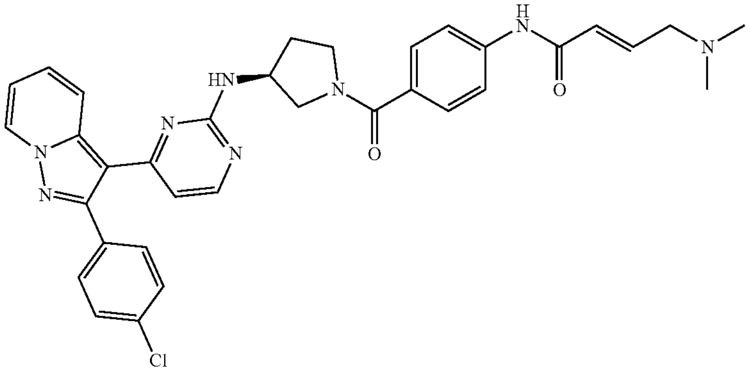 [SMILES: CN(C)C/C=C/C(=O)Nc1ccc(C(=O)N2CC[C@H](Nc3nccc(-c4c(-c5ccc(Cl)cc5)nn5ccccc45)n3)C2)cc1] | I-26 | 8.90 | 67.6 | 10.3 |
| 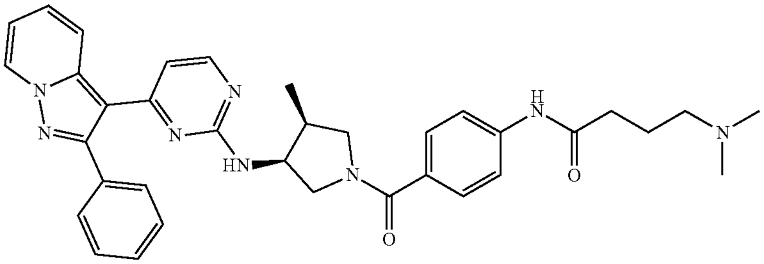 [SMILES: C[C@H]1CN(C(=O)c2ccc(NC(=O)CCCN(C)C)cc2)C[C@H]1Nc1nccc(-c2c(-c3ccccc3)nn3ccccc23)n1] | I-27 | 2600 | 99.5 | 790 |

TABLE 1-continued
| IC$_{50}$ assay with exemplary compounds | | | | |
|---|---|---|---|---|
| Structure | ID | JNK1 (nM) | JNK2 (nM) | JNK3 (nM) |
| 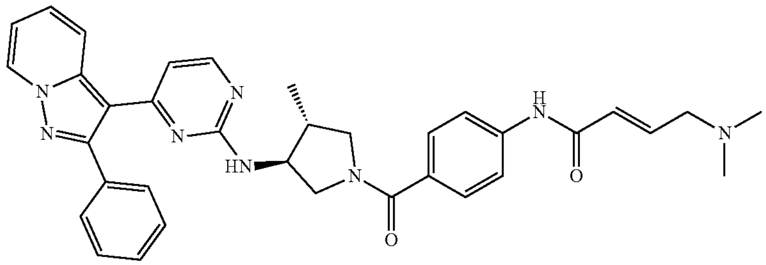 [SMILES: C[C@@H]1CN(C(=O)c2ccc(NC(=O)/C=C/CN(C)C)cc2)C[C@H]1Nc1nccc(-c2c(-c3ccccc3)nn3ccccc23)n1] | I-28 | 223 | 17.6 | 60.1 |
| 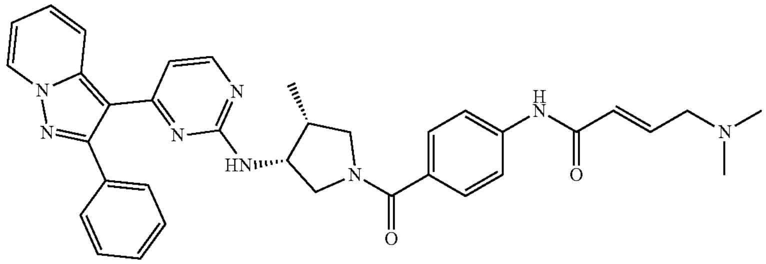 [SMILES: C[C@@H]1CN(C(=O)c2ccc(NC(=O)/C=C/CN(C)C)cc2)C[C@@H]1Nc1nccc(-c2c(-c3ccccc3)nn3ccccc23)n1] | I-29 | 261 | 35.6 | 132 |
| 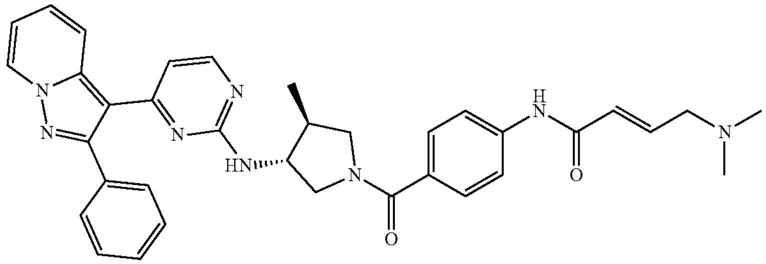 [SMILES: C[C@H]1CN(C(=O)c2ccc(NC(=O)/C=C/CN(C)C)cc2)C[C@@H]1Nc1nccc(-c2c(-c3ccccc3)nn3ccccc23)n1] | I-30 | 89.9 | 5.48 | 26.2 |
| 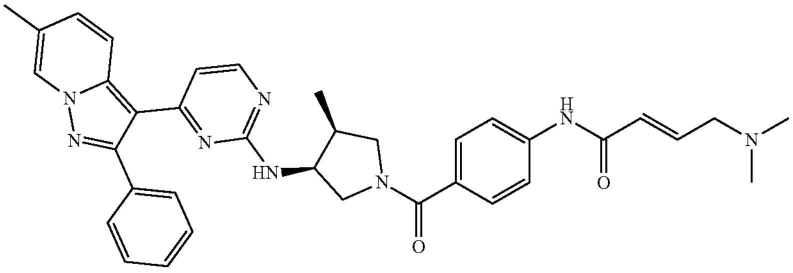 | I-31 | 2390 | 85.8 | 274 |
| 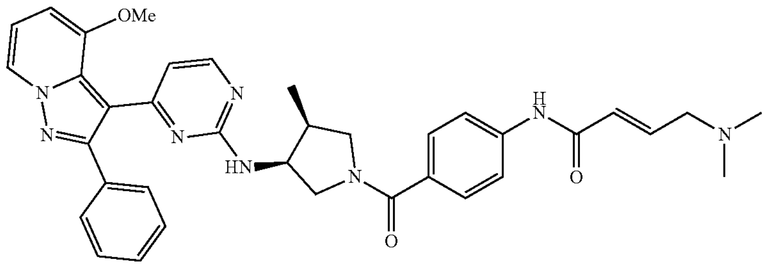 [SMILES: COc1cccn2nc(-c3ccccc3)c(-c3ccnc(N[C@@H]4CN(C(=O)c5ccc(NC(=O)/C=C/CN(C)C)cc5)C[C@@H]4C)n3)c12] | I-32 | 1810 | 222 | >3,330 |

It is expected that the compounds described herein may be useful in treating and/or preventing diseases associated with aberrant activity (e.g., increased activity, undesired activity, abnormal activity) of a kinase (e.g., a JNK (e.g., JNK2)). It is known in the art that kinases are implicated in a wide range of diseases and conditions, such as proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell. Therefore, the compounds described herein are expected to be useful in treating and/or preventing diseases (e.g., proliferative diseases, inflammatory diseases, autoimmune diseases, cardiovascular diseases).

The present disclosure also provides a compound of Formula (I), or a pharmaceutically acceptable salt, co-crystal, tautomer, stereoisomer, solvate, hydrate, polymorph, isotopologue, or prodrug, or composition thereof, for use in the treatment of diseases, such as proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell.

The present disclosure also provides uses of a compound of Formula (I), or a pharmaceutically acceptable salt, co-crystal, tautomer, stereoisomer, solvate, hydrate, polymorph, isotopologue, or prodrug, or composition thereof, in the manufacture of a medicament for the treatment of diseases, such as proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell.

In another aspect, the present disclosure provides methods of modulating the activity of a kinase (e.g., JNK (e.g., JNK2)) in a subject, biological sample, tissue, or cell. In certain embodiments, provided are methods of inhibiting the activity of a kinase in a subject (e.g., JNK (e.g., JNK2)). In certain embodiments, provided are methods of inhibiting the activity of a kinase in a cell (e.g., JNK (e.g., JNK2)). In certain embodiments, provided are methods of increasing the activity of a kinase (e.g., JNK (e.g., JNK1, JNK2, or JNK3)) in a subject. The compounds described herein may exhibit kinase inhibitory activity; the ability to inhibit a kinase; the ability to inhibit a JNK; the ability to inhibit JNK2, without inhibiting another JNK (e.g., JNK1 or JNK3), a therapeutic effect and/or preventative effect in the treatment of cancers; a therapeutic effect and/or preventative effect in the treatment of proliferative diseases (e.g., cancer and benign neoplasms), inflammatory diseases (e.g., rheumatoid arthritis), autoimmune diseases, and cardiovascular diseases (e.g., atherosclerosis)); and/or a therapeutic profile (e.g., optimum safety and curative effect) that is superior to existing chemotherapeutic agents, or agents for treating proliferative diseases (e.g., cancer and benign neoplasms), inflammatory diseases (e.g., rheumatoid arthritis), autoimmune diseases, and cardiovascular diseases (e.g., atherosclerosis)).

In certain embodiments, provided are methods of decreasing the activity of a kinase (e.g., JNK (e.g., JNK2)) in a subject or biological sample (e.g., cell, tissue) by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a kinase (e.g., JNK (e.g., JNK2, JNK3)) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a kinase (e.g., JNK (e.g., JNK2, JNK3)) in a subject, biological sample, tissue, or cell is selectively inhibited by the method. In some embodiments, the activity of a kinase (e.g., JNK (e.g., JNK1, JNK2, JNK3)) in a subject or cell is selectively decreased by the method.

Without wishing to be bound by any particular theory, the compounds described herein are able to bind (e.g., covalently modify) the JNK being inhibited. In certain embodiments, a compound described herein is able to bind (e.g., covalently modify) the JNK. In certain embodiments, the compound described herein is able to covalently bind a cysteine residue of the JNK. In certain embodiments, the compound is capable of covalently modifying Cys116 of a JNK. In certain embodiments, the compound is capable of covalently modifying Cys116 of a JNK. In certain embodiments, the compound is capable of covalently modifying Cys116 of JNK2. In certain embodiments, the compound is capable of covalently modifying JNK2.

In another aspect, the present disclosure provides methods of inhibiting the activity of a kinase in a subject, the methods comprising administering to the subject an effective amount (e.g., therapeutically effective amount) of a compound, or pharmaceutical composition thereof, as described herein. In another aspect, the present disclosure provides methods of inhibiting the activity of a kinase (e.g., JNK (e.g., JNK2)) in a biological sample, the methods comprising contacting the biological sample with an effective amount of a compound, or pharmaceutical composition thereof, as described herein. In another aspect, the present disclosure provides methods of inhibiting the activity of a kinase in a tissue or cell, the methods comprising contacting the tissue or cell with an effective amount of a compound, or pharmaceutical composition thereof, as described herein.

In another aspect, the present disclosure provides methods of inhibiting the activity of a kinase (e.g., JNK (e.g., JNK2)) in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate.

In certain embodiments, the subject is a non-human transgenic animal, such as a transgenic mouse or transgenic pig. In certain embodiments, the subject is a fish or reptile. In certain embodiments, the subject is an animal. The animal may be of either sex and may be at any stage of development. In certain embodiments, the subject described herein is a human. In certain embodiments, the subject is a non-human animal. In certain embodiments, the subject is a mammal.

In certain embodiments, the cell being contacted with a compound or composition described herein is in vitro. In certain embodiments, the cell being contacted with a compound or composition described herein is in vivo.

In certain embodiments, the biological sample being contacted with the compound or composition is breast tissue, bone marrow, lymph node, lymph tissue, spleen, or blood. In certain embodiments, the biological sample being contacted with the compound or composition is a tumor or cancerous tissue. In certain embodiments, the biological sample being contacted with the compound or composition is serum, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

In certain embodiments, the cell or tissue being contacted with the compound or composition is present in vitro. In certain embodiments, the cell or tissue being contacted with the compound or composition is present in vivo. In certain embodiments, the cell or tissue being contacted with the compound or composition is present ex vivo. In certain embodiments, the cell or tissue being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant white blood cell. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a breast carcinoma cell. In certain embodiments, the cell being contacted with the compound or composition is a sarcoma cell. In certain embodiments, the cell being contacted with the compound or composition is a sarcoma cell from breast tissue.

The disease (e.g., proliferative disease, inflammatory disease, autoimmune disease, or cardiovascular disease) to be treated or prevented using the compounds described herein may be associated with increased activity of a kinase, such as a JNK (e.g., JNK2). The disease (e.g., proliferative disease, inflammatory disease, autoimmune disease, or cardiovascular disease) to be treated or prevented using the compounds described herein may be associated with the overexpression of a kinase, such as a JNK (e.g., JNK2).

In certain embodiments, the disease (e.g., proliferative disease, inflammatory disease, autoimmune disease, or cardiovascular disease) to be treated or prevented using the compounds described herein may be associated with the overexpression of a JNK (e.g., JNK2). A disease (e.g., proliferative disease, inflammatory disease, autoimmune disease, or cardiovascular disease) may be associated with aberrant activity of a JNK (e.g., JNK2). Aberrant activity of a JNK (e.g., JNK2) may be elevated and/or inappropriate and/or undesired activity of the JNK. The compounds described herein, and pharmaceutically acceptable salts, solvates, hydrates, polymorphs, co-crystals, tautomers, stereoisomers, isotopologue, prodrugs, and compositions thereof, may inhibit the activity of a JNK (e.g., JNK2) and be useful in treating and/or preventing diseases (e.g., proliferative diseases, inflammatory diseases, autoimmune diseases, or cardiovascular diseases). The compounds described herein, and pharmaceutically acceptable salts, solvates, hydrates, polymorphs, co-crystals, tautomers, stereoisomers, isotopologues, prodrugs, and compositions thereof, may inhibit the activity of a JNK and be useful in treating and/or preventing diseases (e.g., proliferative diseases, inflammatory disease, autoimmune disease, or cardiovascular disease). The compounds described herein, and pharmaceutically acceptable salts, solvates, hydrates, polymorphs, co-crystals, tautomers, stereoisomers, isotopologue, prodrugs, and compositions thereof, may inhibit the activity of a JNK and be useful in treating and/or preventing diseases (e.g., proliferative diseases, inflammatory disease, autoimmune disease, or cardiovascular disease).

In certain embodiments, the disease (e.g., proliferative disease, inflammatory disease, autoimmune disease, or cardiovascular disease) to be treated or prevented using the compounds described herein is cancer. All types of cancers disclosed herein or known in the art are contemplated as being within the scope of the invention. In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myeloid leukemia (AML).

In certain embodiments, the proliferative disease is acute monocytic leukemia (AMoL). In certain embodiments, the proliferative disease is myelodysplastic syndrome (MDS). In certain embodiments, the proliferative disease is a carcinoma. In certain embodiments, the proliferative disease is lymphoma. In certain embodiments, the proliferative disease is T-cell lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is colon cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the proliferative disease is triple-negative breast cancer (TNBC). In certain embodiments, the proliferative disease is a bone cancer. In certain embodiments, the proliferative disease is sarcoma. In certain embodiments, the proliferative disease is osteosarcoma. In certain embodiments, the proliferative disease is Kaposi's sarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is liver cancer. In some embodiments, the proliferative disease is pancreatic cancer. In some embodiments, the proliferative disease is gastric cancer. In some embodiments, the proliferative disease is ovarian cancer. In some embodiments, the proliferative disease is ovarian cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of a kinase (e.g., JNK (e.g., JNK1, JNK2, JNK3)). In certain embodiments, a therapeutically effective amount is an amount effective for treating a disease (e.g., a disease associated with aberrant activity of a JNK (e.g., proliferative diseases (e.g., cancer and benign neoplasms), inflammatory diseases (e.g., rheumatoid arthritis), autoimmune diseases, and cardiovascular diseases (e.g., atherosclerosis)) in a subject, biological sample, tissue, or cell.). In certain embodiments, a therapeutically effective amount is an amount effective for inducing apoptosis of a cell (e.g., cell in vivo or in vitro). In certain embodiments, a prophylactically effective amount is an amount effective for inhibiting the aberrant activity of a protein (e.g., JNK (e.g., JNK1, JNK2, or JNK3)). In certain embodiments, a prophylactically effective amount is an amount effective for preventing or keeping a subject in need thereof in remission of a disease (e.g., a disease associated with aberrant activity of a JNK (e.g., proliferative disease). In certain embodiments, a prophylactically effective amount is an amount effective for inhibiting the aberrant activity of a JNK, and preventing or keeping a subject in need thereof in remission of a disease (e.g., a disease associated with aberrant activity of a JNK (e.g., a proliferative disease)).

In certain embodiments, the effective amount is an amount effective for inhibiting the activity of a kinase (e.g., JNK (e.g., JNK1, JNK2, or JNK3)) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a JNK (e.g., JNK1, JNK2, or JNK3)) by not more than 10%, not more than 20%, not more than 30%, not more than 40%, not more than 50%, not more than 60%, not more than 70%, not more than 80%, not more than 90%, not more than 95%, or not more than 98%.

Another aspect of the disclosure relates to methods of inhibiting the activity of a kinase in a biological sample, tissue, cell, or subject. In certain embodiments, the JNK is JNK2. In certain embodiments, JNK2 is selectively inhibited over another kinase (e.g., JNK (e.g., JNK1, JNK3)). In certain embodiments, the activity of the kinase is aberrant activity of the kinase. In certain embodiments, the activity of the kinase is increased activity of the kinase. In certain embodiments, the inhibition of the activity of the kinase is irreversible. In certain embodiments, the methods of inhibiting the activity of the kinase include attaching a compound described herein to the kinase. In certain embodiments, the methods comprise covalently inhibiting a JNK (e.g., JNK2). The present invention provides methods of inhibiting cell growth in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopologue, or prodrug thereof, or a pharmaceutical composition thereof. All types of biological samples described herein or known in the art are contemplated as being within the scope of the invention. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a kinase. In certain embodiments, the additional pharmaceutical agent is an inhibitor of JNK. In certain embodiments, the additional pharmaceutical agent is an inhibitor of JNK1. In certain embodiments, the additional pharmaceutical agent is an inhibitor of JNK2. In certain embodiments, the additional pharmaceutical agent is an inhibitor of JNK3. In certain embodiments, the additional pharmaceutical agent is a selective inhibitor of a kinase. In certain embodiments, the additional pharmaceutical agent is a selective inhibitor of a JNK. In certain embodiments, the additional pharmaceutical agent is a selective inhibitor of JNK1. In certain embodiments, the additional pharmaceutical agent is a selective inhibitor of JNK2. In certain embodiments, the additional pharmaceutical agent is a selective inhibitor of JNK3. In certain embodiments, the additional pharmaceutical agent is a non-selective inhibitor of JNK1. In certain embodiments, the additional pharmaceutical agent is a non-selective inhibitor of JNK2. In certain embodiments, the additional pharmaceutical agent is a non-selective inhibitor of JNK3. In certain embodiments, the additional pharmaceutical agent is an anti-cancer agent (e.g., chemotherapeutics), anti-inflammatory agent, steroid, immunosuppressant, radiation therapy, or other agent. In certain embodiments, the additional pharmaceutical agent is an anti-proliferative agent. In certain embodiments, the additional pharmaceutical agent is an inhibitor of a kinase. In certain embodiments, the additional pharmaceutical agent is a non-selective inhibitor of a kinase. In certain embodiments, the additional pharmaceutical agent is an immunotherapy agent (e.g., PD1 inhibitor, PDL1 inhibitor). In certain embodiments, the additional pharmaceutical agent is an immune checkpoint inhibitor.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a BTK inhibitor. In certain embodiments, the additional pharmaceutical agent is ibrutinib.

In certain embodiments, the additional pharmaceutical agent is a kinase inhibitor (e.g., a JNK family kinase inhibitor). In certain embodiments, the additional pharmaceutical agent is a binder or inhibitor of a JNK (e.g., JNK1, JNK2, or JNK3)). In certain embodiments, the additional pharmaceutical agent is a binder or inhibitor of a JNK. In certain embodiments, the additional pharmaceutical agent is a binder or inhibitor of JNK1. In certain embodiments, the additional pharmaceutical agent is a binder or inhibitor of JNK2. In certain embodiments, the additional pharmaceutical agent is a binder or inhibitor of JNK3. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., transcription factor inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy. In some embodiments, the additional pharmaceutical agent is a BTK inhibitor (e.g., Ibrutinib), a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. Exemplary chemotherapeutic agents include alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as *vinca* alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant. Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine. In certain embodiments, a pharmaceutical composition described herein further comprises a combination of the additional pharmaceutical agents described herein.

The inventive compounds or compositions may synergistically augment inhibition of JNK induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In certain embodiments, a kit described herein includes a first container comprising a compound or pharmaceutical composition described herein. In certain embodiments, a kit described herein is useful in treating and/or preventing a disease, such as a proliferative diseases (e.g., cancer and benign neoplasms), inflammatory diseases (e.g., rheumatoid arthritis), autoimmune diseases, and cardiovascular diseases (e.g., atherosclerosis)) in a subject. In certain embodiments, a kit described herein is useful in inhibiting the activity of a kinase (e.g., a JNK (e.g., JNK2)) in a subject, biological sample, tissue, or cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease, (e.g., proliferative diseases (e.g., cancer and benign neoplasms), inflammatory diseases (e.g., rheumatoid arthritis), autoimmune diseases, and cardiovascular diseases (e.g., atherosclerosis)), preventing a disease (e.g., proliferative diseases (e.g., cancer and benign neoplasms), inflammatory diseases (e.g., rheumatoid arthritis), autoimmune diseases, and cardiovascular diseases (e.g., atherosclerosis)), inhibiting the activity of a kinase (e.g., JNK (e.g., JNK2)) in a subject, biological sample, tissue, or cell. A kit described herein may include one or more additional pharmaceutical agents described herein as a separate composition.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds of the Present Disclosure

Synthesis of I-1 and I-4

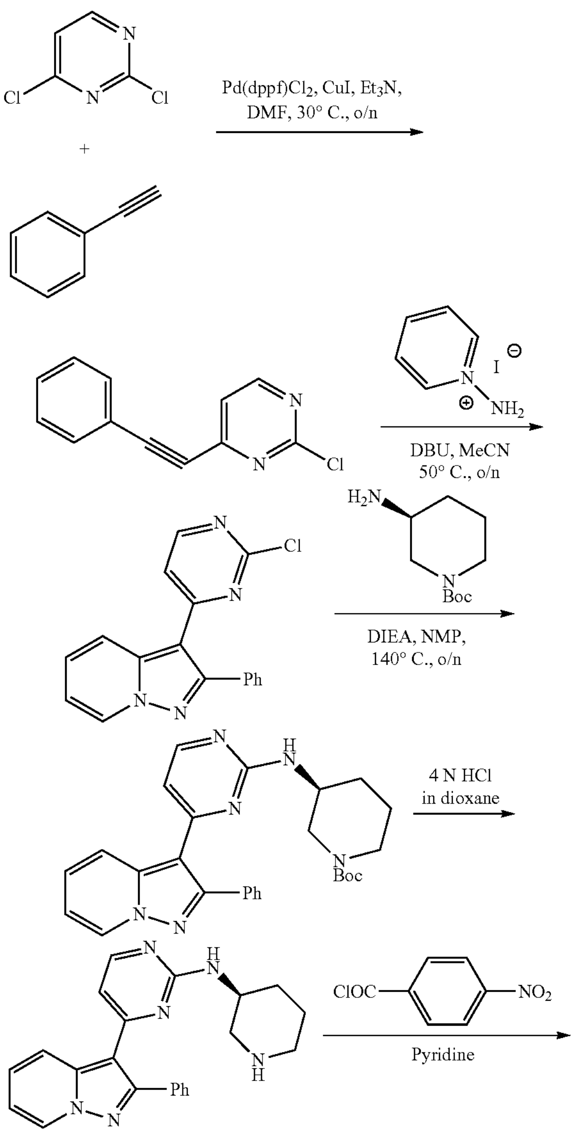

-continued

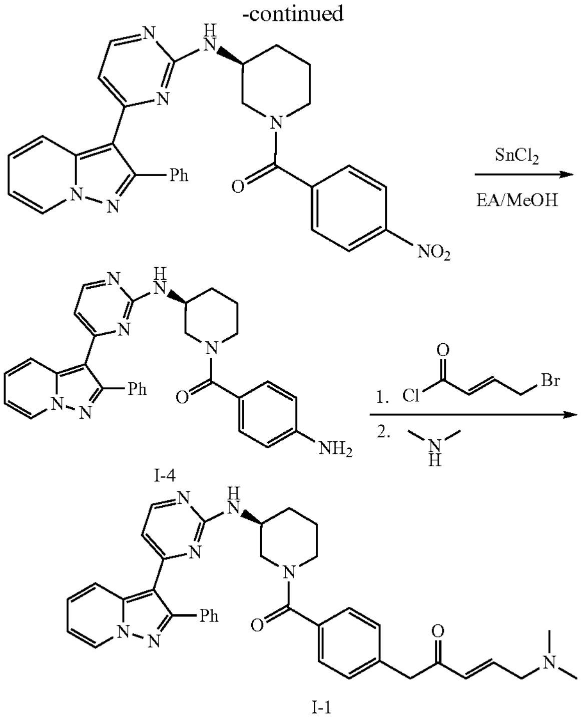

I-4

I-1

2-Chloro-4-(phenylethynyl)pyrimidine

To a solution of 2,4-dichloropyrimidine (600 mg, 4 mmol) and ethynylbenzene (500 mg, 4.8 mmol) in DMF (10 mL) were added Pd(dppf)$Cl_2$ (14 mg, 0.02 mmol), CuI (7.6 mg, 0.04 mmol) and $Et_3N$ (5.5 mL, 40 mmol) under $N_2$ atmosphere. The reaction mixture was stirred at 30° C. overnight. After cooling to room temperature, the reaction mixture was diluted with water (50 mL), extracted with ethyl acetate, dried over $Na_2SO_4$ and concentrated in vacuo. The residue was purified by column chromatography on silica gel (EA/hexane=1/4) to give the title compound (640 mg, 74%). LC/MS (ESI) m/z=215 $(M+H)^+$.

To a solution of 2-chloro-4-(phenylethynyl)pyrimidine (640 mg, 3 mmol) and 1-aminopyridinium iodide (800 mg, 3.6 mmol) in MeCN (10 mL) was added DBU (544 mg, 3.6 mmol) at 0° C. The reaction mixture was stirred at 50° C. overnight. After cooling to room temperature, the reaction mixture was diluted with water (200 mL), the precipitated solid was filtered to give the title compound (700 mg, 76%). LC/MS (ESI) m/z=307 $(M+H)^+$.

tert-butyl (S)-3-((4-(2-phenylpyrazolo[1,5-a]pyridin-3-yl)pyrimidin-2-yl)amino)piperidine-1-carboxylate To a solution of 3-(2-chloropyrimidin-4-yl)-2-phenylpyrazolo[1,5-a]pyridine (200 mg, 0.65 mmol) and tert-butyl (S)-3-aminopiperidine-1-carboxylate (195 mg, 1.5 mmol) in NMP (3 mL) was added DIEA (0.32 mL, 1.95 mmol). The reaction mixture was stirred at 140° C. overnight. The mixture was diluted with water (200 mL), extracted with ethyl acetate, washed with brine, dried over $Na_2SO_4$, and concentrated in vacuo. The residue was then used in the next step without any purification. LC/MS (ESI) m/z=471 $(M+H)^+$.

(S)-4-(2-phenylpyrazolo[1,5-a]pyridin-3-yl)-N-(piperidin-3-yl)pyrimidin-2-amine

To a solution of tert-butyl (S)-3-((4-(2-phenylpyrazolo[1,5-a]pyridin-3-yl)pyrimidin-2-yl)amino)piperidine-1-carboxylate (crude from last step) in dioxane (2 mL) was added 2 mL of HCl (4 N in dioxane). The reaction mixture was stirred at room temperature overnight, and then concentrated in vacuo. The residue was redissolved in MeOH, and then neutralized with 1 N $NaHCO_3$ aq to pH=9. The resulting mixture was extracted with isopropanol/chloroform (v/v=1/3). The combined organic layer was washed with brine, dried over $Na_2SO_4$ and concentrated in vacuo. The residue was purified by column chromatography on silica gel (1.75 N $NH_3$ in methanol/DCM=1/5) to give the title compound (93 mg, 38% for 2 steps). LC/MS (ESI) m/z=371 $(M+H)^+$.

(S)-(4-nitrophenyl)(3-((4-(2-phenylpyrazolo[1,5-a]pyridin-3-yl)pyrimidin-2-yl)amino)piperidin-1-yl)methanone To a solution of (S)-4-(2-phenylpyrazolo[1,5-a]pyridin-3-yl)-N-(piperidin-3-yl)pyrimidin-2-amine (93 mg, 0.25 mmol) in pyridine (3 mL) was added 4-nitrobenzoyl chloride (70 mg, 0.38 mmol). The reaction mixture was stirred at room temperature overnight, and then concentrated in vacuo. The residue was redissolved in water (200 mL), and then extracted with isopropanol/chloroform (v/v=1/3). The combined organic layer was concentrated in vacuo to give crude product, which was used to next step without any purification. LC/MS (ESI) m/z=520 $(M+H)^+$.

(S)-(4-aminophenyl)(3-((4-(2-phenylpyrazolo[1,5-a]pyridin-3-yl)pyrimidin-2-yl)amino)piperidin-1-yl)methanone (I-4)

To a solution of (S)-(4-nitrophenyl)(3-((4-(2-phenylpyrazolo[1,5-a]pyridin-3-yl)pyrimidin-2-yl)amino)piperidin-1-yl)methanone (crude from last step) in 5 mL of ethyl acetate/methanol (v/v=1/1) was added $SnCl_2$ (380 mg, 8 mmol). The reaction mixture was stirred at 80° C. for 2 h. After cooling to room temperature, the reaction mixture was diluted with $Na_2CO_3$ (sat. aq.). The resulting mixture was extracted with isopropanol/chloroform (v/v=1/3). The combined organic layer was concentrated in vacuo, and then purified by prep-HPLC (0.15% TFA in MeOH/$H_2O$, 0-100%) to give I-4 (68 mg, 45% for 2 steps) as TFA salt. LC/MS (ESI) m/z=490 $(M+H)^+$.

(S,E)-4-(dimethylamino)-N-(4-(3-((4-(2-phenylpyrazolo[1,5-a]pyridin-3-yl)pyrimidin-2-yl)amino)piperidine-1-carbonyl)phenyl)but-2-enamide To a solution of (S)-(4-aminophenyl)(3-((4-(2-phenylpyrazolo[1,5-a]pyridin-3-yl)pyrimidin-2-yl)amino)piperidin-1-yl)methanone (28 mg, 0.057 mmol) and DIEA (28 µL, 0.17 mmol) in anhydrous THF (1 mL) was added (E)-4-bromobut-2-enoyl chloride dropwise at 0° C. until the reaction finished. Then excess of dimethylamine (2 N in dioxane) was added. The mixture was stirred at room temperature for 1 h, and then concentrated in vacuo. The residue was purified by prep-HPLC (0.15% TFA in MeOH/$H_2O$, 0-100%) to give I-1 (30 mg, 73%) as TFA salt. LC/MS (ESI) m/z=601 $(M+H)^+$.

Synthesis of I-5

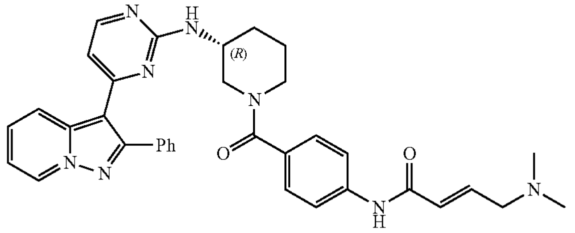

(R,E)-4-(dimethylamino)-N-(4-(3-((4-(2-phenylpyrazolo[1,5-a]pyridin-3-yl)pyrimidin-2-yl)amino)piperidine-1-carbonyl)phenyl)but-2-enamide I-5 (23 mg, 25%) is prepared by using the same procedure as for I-1. Tert-butyl (R)-3-aminopiperidine-1-carboxylate was used in the third step. LC/MS (ESI) m/z=601 $(M+H)^+$.

Synthesis of I-2

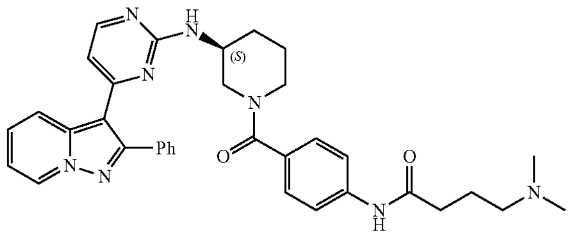

(S)-4-(dimethylamino)-N-(4-(3-((4-(2-phenylpyrazolo[1,5-a]pyridin-3-yl)pyrimidin-2-yl)amino)piperidine-1-carbonyl)phenyl)butanamide I-2 (24.8 mg, 39%) is prepared by using the same procedure as for I-1. 4-Chlorobutanoyl chloride was used in the last step. LC/MS (ESI) m/z=603 $(M+H)^+$.

Synthesis of I-3

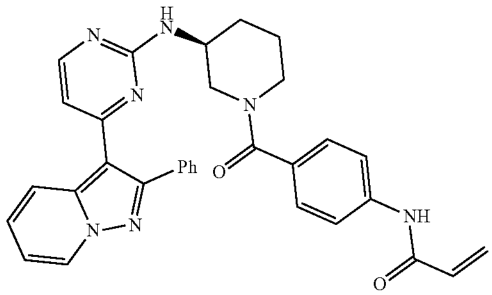 [SMILES: C=CC(=O)Nc1ccc(C(=O)N2CCC[C@H](Nc3nccc(-c4c(-c5ccccc5)nn5ccccc45)n3)C2)cc1]

(S)-N-(4-(3-((4-(2-phenylpyrazolo[1,5-a]pyridin-3-yl)pyrimidin-2-yl)amino)piperidine-1-carbonyl)phenyl)acrylamide I-3 (24.8 mg, 39%) is prepared by using the same procedure as for I-1. Acryloyl chloride was used in the last step. LC/MS (ESI) m/z=544 $(M+H)^+$.

Synthesis of I-6

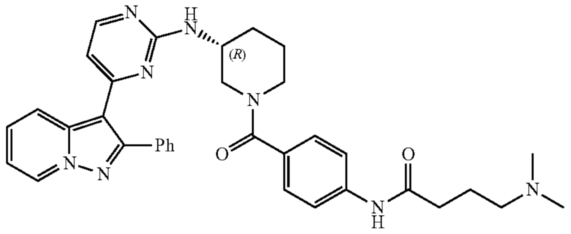

(R)-4-(dimethylamino)-N-(4-(3-((4-(2-phenylpyrazolo[1,5-a]pyridin-3-yl)pyrimidin-2-yl)amino)piperidine-1-carbonyl)phenyl)butanamide I-6 (24.8 mg, 80%) is prepared by using the same procedure as for I-5. 4-Chlorobutanoyl chloride was used in the last step. LC/MS (ESI) m/z=603 $(M+H)^+$.

Synthesis of I-15

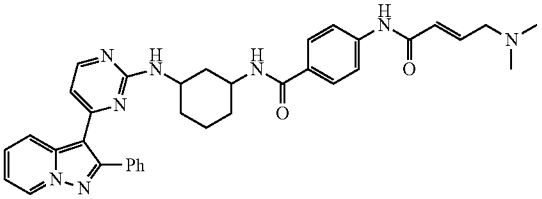

(E)-4-(4-(dimethylamino)but-2-enamido)-N-(3-((4-(2-phenylpyrazolo[1,5-a]pyridin-3-yl)pyrimidin-2-yl)amino)cyclohexyl)benzamide I-15 (34.4 mg, 95%) is prepared by using the same procedure as for I-1. Tert-butyl (3-aminocyclohexyl)carbamate was used in the third step. LC/MS (ESI) m/z=615 $(M+H)^+$.

Synthesis of 1-7

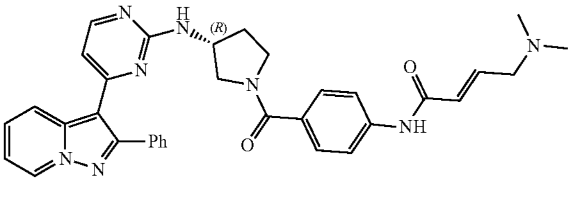

(R,E)-4-(dimethylamino)-N-(4-(3-((4-(2-phenylpyrazolo[1,5-a]pyridin-3-yl)pyrimidin-2-yl)amino)pyrrolidine-1-carbonyl)phenyl)but-2-enamide I-7 (20.1 mg, 57%) is prepared by using the same procedure as for I-1. Tert-butyl (R)-3-aminopyrrolidine-1-carboxylate was used in the third step. LC/MS (ESI) m/z=587 $(M+H)^+$.

Synthesis of I-9

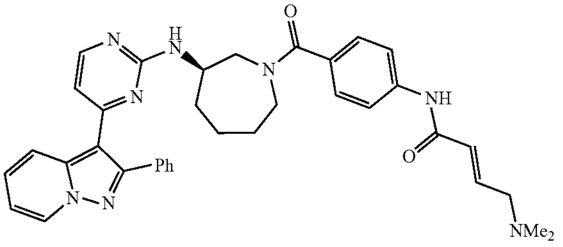 [SMILES: CN(C)C/C=C/C(=O)Nc1ccc(C(=O)N2CCCC[C@@H](Nc3nccc(-c4c(-c5ccccc5)nn5ccccc45)n3)C2)cc1]

(R,E)-4-(dimethylamino)-N-(4-(3-((4-(2-phenylpyrazolo[1,5-a]pyridin-3-yl)pyrimidin-2-yl)amino)azepane-1-carbonyl)phenyl)but-2-enamide I-9 (31.2 mg, 88%) is prepared by using the same procedure as for I-1. Tert-butyl (R)-3-aminoazepane-1-carboxylate was used in the third step. LC/MS (ESI) m/z=615 $(M+H)^+$.

Synthesis of I-10

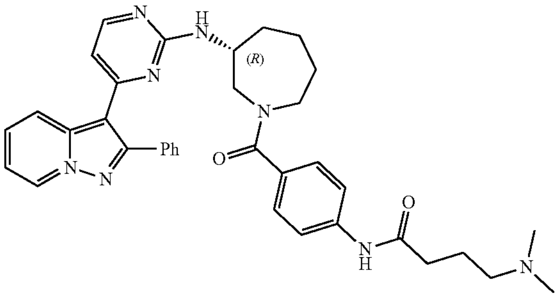

(R)-4-(dimethylamino)-N-(4-(3-((4-(2-phenylpyrazolo[1,5-a]pyridin-3-yl)pyrimidin-2-yl)amino)azepane-1-carbonyl)phenyl)butanamide I-10 (28.2 mg, 78%) is prepared by using the same procedure as for I-9. 4-Chlorobutanoyl chloride was used in the last step. LC/MS (ESI) m/z=617 $(M+H)^+$.

Synthesis of I-8

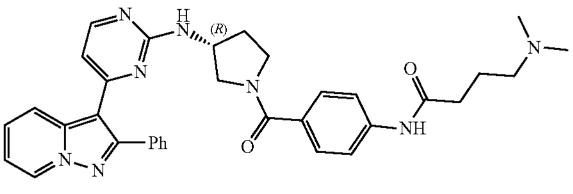

(R)-4-(dimethylamino)-N-(4-(3-((4-(2-phenylpyrazolo[1,5-a]pyridin-3-yl)pyrimidin-2-yl)amino)pyrrolidine-1-carbonyl)phenyl)butanamide I-8 (6.8 mg, 30%) is prepared by using the same procedure as for I-7. 4-Chlorobutanoyl chloride was used in the last step. LC/MS (ESI) m/z=589 $(M+H)^+$.

Synthesis of I-11

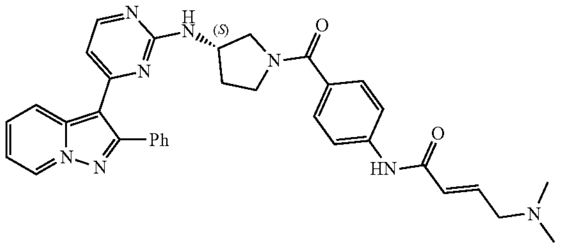

(S,E)-4-(dimethylamino)-N-(4-(3-((4-(2-phenylpyrazolo[1,5-a]pyridin-3-yl)pyrimidin-2-yl)amino)pyrrolidine-1-carbonyl)phenyl)but-2-enamide I-11 (18 mg, 51%) is prepared by using the same procedure as for I-1. Tert-butyl (S)-3-aminopyrrolidine-1-carboxylate was used in the third step. LC/MS (ESI) m/z=587 $(M+H)^+$.

Synthesis of I-12

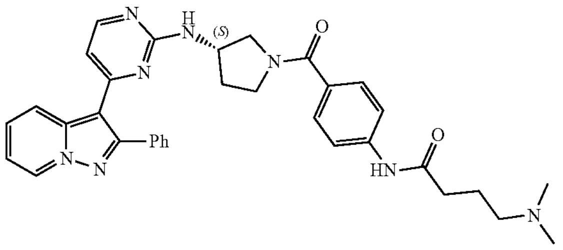

(S)-4-(dimethylamino)-N-(4-(3-((4-(2-phenylpyrazolo[1,5-a]pyridin-3-yl)pyrimidin-2-yl)amino)pyrrolidine-1-carbonyl)phenyl)butanamide I-12 (23.8 mg, 66%) is prepared by using the same procedure as for I-11. 4-Chlorobutanoyl chloride was used in the last step. LC/MS (ESI) m/z=589 $(M+H)^+$.

Synthesis of I-13

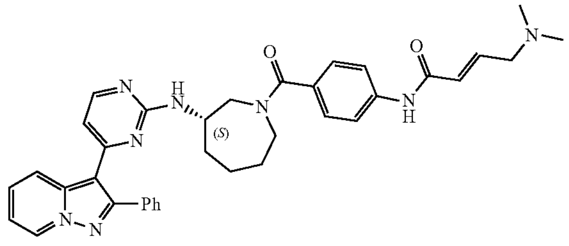

(S,E)-4-(dimethylamino)-N-(4-(3-((4-(2-phenylpyrazolo[1,5-a]pyridin-3-yl)pyrimidin-2-yl)amino)azepane-1-carbonyl)phenyl)but-2-enamide I-13 (26.6 mg, 75%) is prepared by using the same procedure as for I-1. Tert-butyl (S)-3-aminoazepane-1-carboxylate was used in the third step. LC/MS (ESI) m/z=615 $(M+H)^+$.

Synthesis of I-14

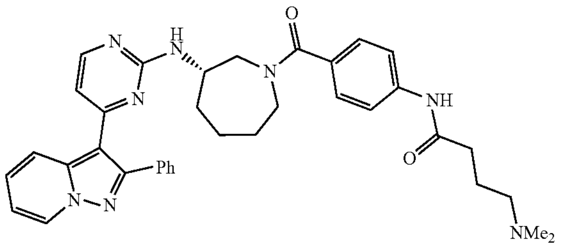 [SMILES: CN(C)CCCC(=O)Nc1ccc(C(=O)N2CCCC[C@H](Nc3nccc(-c4c(-c5ccccc5)nn5ccccc45)n3)C2)cc1]

(S)-4-(dimethylamino)-N-(4-(3-((4-(2-phenylpyrazolo[1,5-a]pyridin-3-yl)pyrimidin-2-yl)amino)azepane-1-carbonyl)phenyl)butanamide I-14 (12.8 mg, 36%) is prepared by using the same procedure as for I-13. 4-Chlorobutanoyl chloride was used in the last step. LC/MS (ESI) m/z=617 $(M+H)^+$.

Synthesis of I-16

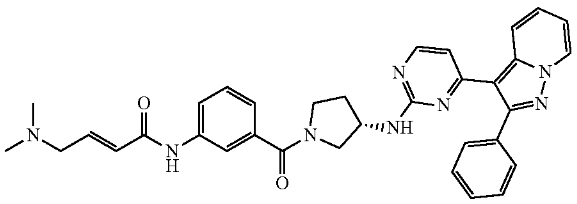 [SMILES: CN(C)C/C=C/C(=O)Nc1cccc(C(=O)N2CC[C@H](Nc3nccc(-c4c(-c5ccccc5)nn5ccccc45)n3)C2)c1]

(S,E)-4-(dimethylamino)-N-(3-(3-((4-(2-phenylpyrazolo[1,5-a]pyridin-3-yl)pyrimidin-2-yl)amino)pyrrolidine-1-carbonyl)phenyl)but-2-enamide I-16 (2.6 mg, 62%) is prepared by using the same procedure as for I-1. 3-nitrobenzoyl chloride was used in the fifth step. LC/MS (ESI) m/z=587 $(M+H)^+$.

Synthesis of I-17

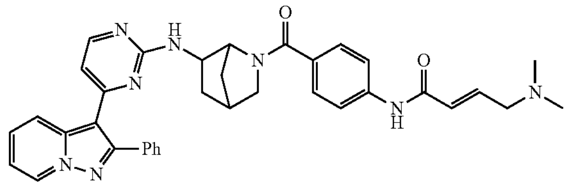

(E)-4-(dimethylamino)-N-(4-(6-((4-(2-phenylpyrazolo[1,5-a]pyridin-3-yl)pyrimidin-2-yl)amino)-2-azabicyclo[2.2.1]heptane-2-carbonyl)phenyl)but-2-enamide I-17 (7.6 mg, 44%) is prepared by using the same procedure as for I-1. Tert-butyl 6-amino-2-azabicyclo[2.2.1]heptane-2-carboxylate was used in the third step. LC/MS (ESI) m/z=613 $(M+H)^+$.

Synthesis of I-18

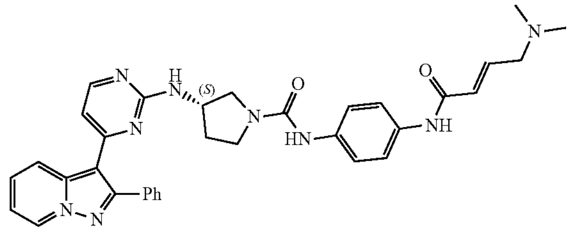

(S,E)-N-(4-(4-(dimethylamino)but-2-enamido)phenyl)-3-((4-(2-phenylpyrazolo[1,5-a]pyridin-3-yl)pyrimidin-2-yl)amino)pyrrolidine-1-carboxamide I-18 (10 mg, 50%) is prepared by using the similar procedure as for I-1. 1-Isocyanato-4-nitrobenzene was used in the fifth step. LC/MS (ESI) m/z=602 $(M+H)^+$.

Synthesis of I-19

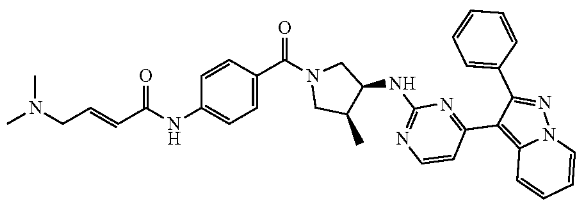 [SMILES: C[C@H]1CN(C(=O)c2ccc(NC(=O)/C=C/CN(C)C)cc2)C[C@H]1Nc1nccc(-c2c(-c3ccccc3)nn3ccccc23)n1]

(E)-4-(dimethylamino)-N-(4-((3S,4S)-3-methyl-4-((4-(2-phenylpyrazolo[1,5-a]pyridin-3-yl)pyrimidin-2-yl)amino)pyrrolidine-1-carbonyl)phenyl)but-2-enamide I-19 (1.4 mg, 15%) is prepared by using the similar procedure as for I-1. Tert-butyl (3S,4S)-3-amino-4-methylpyrrolidine-1-carboxylate was used in the third step. LC/MS (ESI) m/z=601 $(M+H)^+$.

Synthesis of I-20

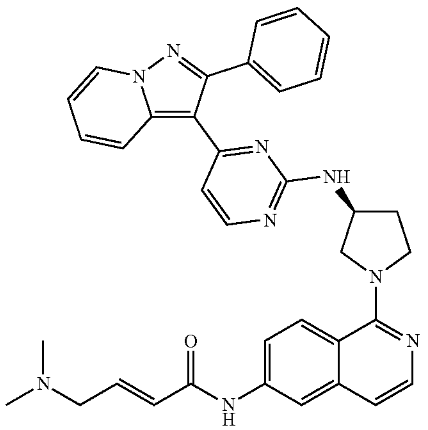 [SMILES: CN(C)C/C=C/C(=O)Nc1ccc2c(N3CC[C@H](Nc4nccc(-c5c(-c6ccccc6)nn6ccccc56)n4)C3)nccc2c1]

(S,E)-4-(dimethylamino)-N-(1-(3-((4-(2-phenylpyrazolo[1,5-a]pyridin-3-yl)pyrimidin-2-yl)amino)pyrrolidin-1-yl)isoquinolin-6-yl)but-2-enamide I-20 (4.8 mg, 19%) is prepared by using the similar procedure as for I-1. 1-chloro-6-nitroisoquinoline was used in the fifth step. LC/MS (ESI) m/z=610 $(M+H)^+$.

Synthesis of I-21

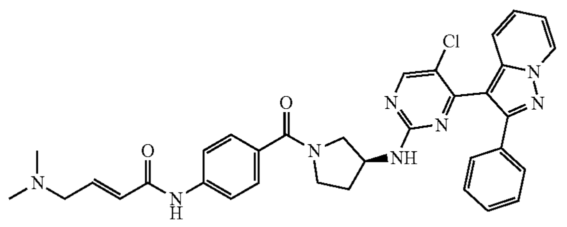 [SMILES: CN(C)C/C=C/C(=O)Nc1ccc(C(=O)N2CC[C@H](Nc3ncc(Cl)c(-c4c(-c5ccccc5)nn5ccccc45)n3)C2)cc1]

(S,E)-N-(4-(3-((5-chloro-4-(2-phenylpyrazolo[1,5-a]pyridin-3-yl)pyrimidin-2-yl)amino)pyrrolidine-1-carbonyl)phenyl)-4-(dimethylamino)but-2-enamide I-21 (7.5 mg, 26%) is prepared by using the similar procedure as for I-1. 2,4,5-Trichloropyrimidine was used in the first step. LC/MS (ESI) m/z=621 $(M+H)^+$.

Synthesis of I-22

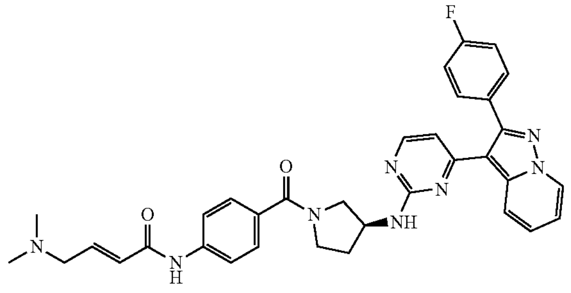 [SMILES: CN(C)C/C=C/C(=O)Nc1ccc(C(=O)N2CC[C@H](Nc3nccc(-c4c(-c5ccc(F)cc5)nn5ccccc45)n3)C2)cc1]

(S,E)-4-(dimethylamino)-N-(4-(3-((4-(2-(4-fluorophenyl)pyrazolo[1,5-a]pyridin-3-yl)pyrimidin-2-yl)amino)pyrrolidine-1-carbonyl)phenyl)but-2-enamide I-21 (5.1 mg, 21%) is prepared by using the similar procedure as for I-1. 1-ethynyl-4-fluorobenzene was used in the first step. LC/MS (ESI) m/z=605 $(M+H)^+$.

Synthesis of I-23

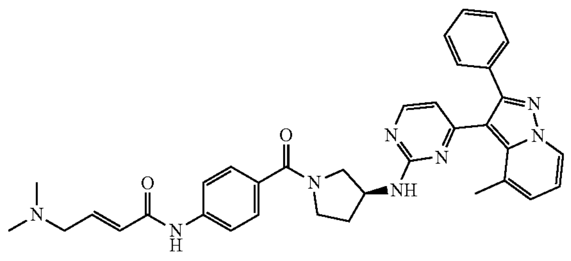 [SMILES: Cc1cccn2nc(-c3ccccc3)c(-c3ccnc(N[C@H]4CCN(C(=O)c5ccc(NC(=O)/C=C/CN(C)C)cc5)C4)n3)c12]

(S,E)-4-(dimethylamino)-N-(4-(3-((4-(4-methyl-2-phenylpyrazolo[1,5-a]pyridin-3-yl)pyrimidin-2-yl)amino)pyrrolidine-1-carbonyl)phenyl)but-2-enamide I-23 (27 mg, 53%) is prepared by using the similar procedure as for I-1. 1-Amino-3-methylpyridinium iodide was used in the second step. LC/MS (ESI) m/z=601 $(M+H)^+$.

Synthesis of I-24

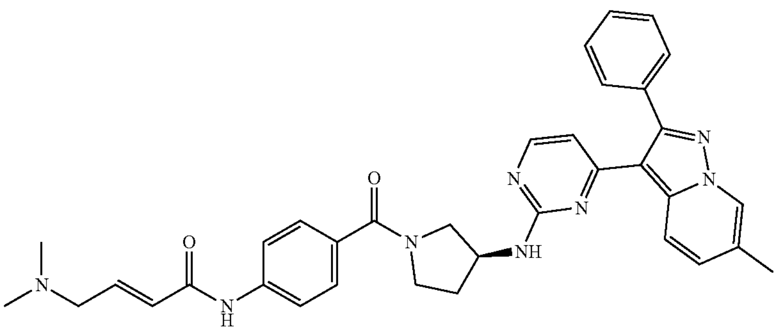

(S,E)-4-(dimethylamino)-N-(4-(3-((4-(6-methyl-2-phenylpyrazolo[1,5-a]pyridin-3-yl)pyrimidin-2-yl)amino)pyrrolidine-1-carbonyl)phenyl)but-2-enamide I-24 (20 mg, 51%) is prepared by using the similar procedure as for I-23. 3-(2-chloropyrimidin-4-yl)-6-methyl-2-phenylpyrazolo[1,5-a]pyridine was used in the third step. LC/MS (ESI) m/z=601 $(M+H)^+$.

Synthesis of I-25

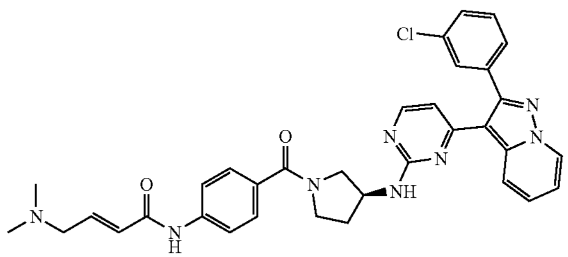 [SMILES: CN(C)C/C=C/C(=O)Nc1ccc(C(=O)N2CC[C@H](Nc3nccc(-c4c(-c5cccc(Cl)c5)nn5ccccc45)n3)C2)cc1]

(S,E)-N-(4-(3-((4-(2-(3-chlorophenyl)pyrazolo[1,5-a]pyridin-3-yl)pyrimidin-2-yl)amino)pyrrolidine-1-carbonyl)phenyl)-4-(dimethylamino)but-2-enamide I-25 (12.3 mg, 39%) is prepared by using the similar procedure as for I-1. 1-Chloro-3-ethynylbenzene was used in the first step. LC/MS (ESI) m/z=621 $(M+H)^+$.

Synthesis of I-26

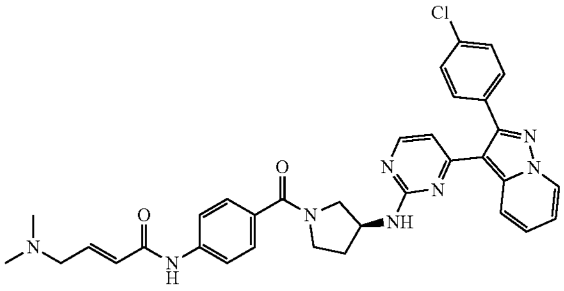 [SMILES: CN(C)C/C=C/C(=O)Nc1ccc(C(=O)N2CC[C@H](Nc3nccc(-c4c(-c5ccc(Cl)cc5)nn5ccccc45)n3)C2)cc1]

(S,E)-N-(4-(3-((4-(2-(4-chlorophenyl)pyrazolo[1,5-a]pyridin-3-yl)pyrimidin-2-yl)amino)pyrrolidine-1-carbonyl)phenyl)-4-(dimethylamino)but-2-enamide I-26 (21.1 mg, 29%) is prepared by using the similar procedure as for I-1. 1-chloro-4-ethynylbenzene was used in the first step. LC/MS (ESI) m/z=621 $(M+H)^+$.

Synthesis of I-27

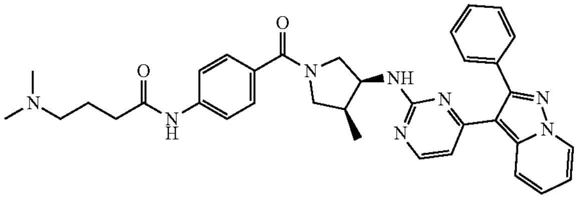 [SMILES: C[C@H]1CN(C(=O)c2ccc(NC(=O)CCCN(C)C)cc2)C[C@H]1Nc1nccc(-c2c(-c3ccccc3)nn3ccccc23)n1]

4-(dimethylamino)-N-(4-((3S,4S)-3-methyl-4-((4-(2-phenylpyrazolo[1,5-a]pyridin-3-yl)pyrimidin-2-yl)amino)pyrrolidine-1-carbonyl)phenyl)butanamide I-27 (4.8 mg, 40%) is prepared by using the similar procedure as for I-19. 4-Chlorobutanoyl chloride was used in the last step. LC/MS (ESI) m/z=603 $(M+H)^+$.

Synthesis of I-28

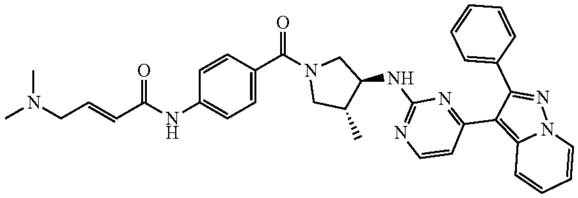 [SMILES: C[C@@H]1CN(C(=O)c2ccc(NC(=O)/C=C/CN(C)C)cc2)C[C@H]1Nc1nccc(-c2c(-c3ccccc3)nn3ccccc23)n1]

(E)-4-(dimethylamino)-N-(4-((3R,4S)-3-methyl-4-((4-(2-phenylpyrazolo[1,5-a]pyridin-3-yl)pyrimidin-2-yl)amino)pyrrolidine-1-carbonyl)phenyl)but-2-enamide I-28 (10 mg, 50%) is prepared by using the similar procedure as for I-1. Tert-butyl (3S,4R)-3-amino-4-methylpyrrolidine-1-carboxylate was used in the third step. LC/MS (ESI) m/z=601 $(M+H)^+$.

Synthesis of I-29

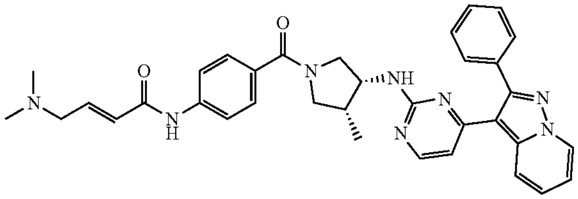 [SMILES: C[C@@H]1CN(C(=O)c2ccc(NC(=O)/C=C/CN(C)C)cc2)C[C@@H]1Nc1nccc(-c2c(-c3ccccc3)nn3ccccc23)n1]

(E)-4-(dimethylamino)-N-(4-((3R,4R)-3-methyl-4-((4-(2-phenylpyrazolo[1,5-a]pyridin-3-yl)pyrimidin-2-yl)amino)pyrrolidine-1-carbonyl)phenyl)but-2-enamide I-29 (10 mg, 57%) is prepared by using the similar procedure as for I-1. Tert-butyl (3R,4R)-3-amino-4-methylpyrrolidine-1-carboxylate was used in the third step. LC/MS (ESI) m/z=601 $(M+H)^+$.

Synthesis of I-30

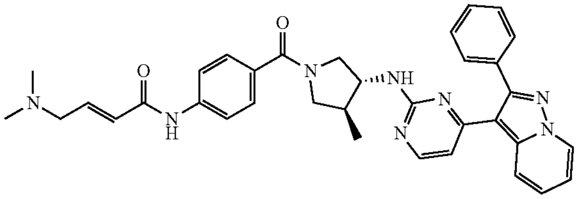 [SMILES: C[C@H]1CN(C(=O)c2ccc(NC(=O)/C=C/CN(C)C)cc2)C[C@@H]1Nc1nccc(-c2c(-c3ccccc3)nn3ccccc23)n1]

(E)-4-(dimethylamino)-N-(4-((3S,4R)-3-methyl-4-((4-(2-phenylpyrazolo[1,5-a]pyridin-3-yl)pyrimidin-2-yl)amino)pyrrolidine-1-carbonyl)phenyl)but-2-enamide I-30 is prepared by using the similar procedure as for I-1. Tert-butyl (3R,4S)-3-amino-4-methylpyrrolidine-1-carboxylate was used in the third step. LC/MS (ESI) m/z=601 $(M+H)^+$.

Synthesis of I-31

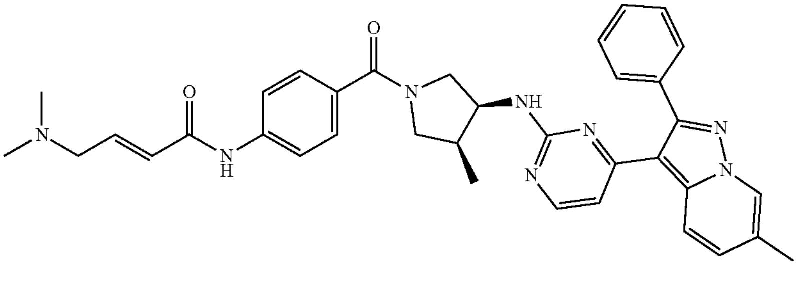

(E)-4-(dimethylamino)-N-(4-((3S,4S)-3-methyl-4-((4-(6-methyl-2-phenylpyrazolo[1,5-a]pyridin-3-yl)pyrimidin-2-yl)amino)pyrrolidine-1-carbonyl)phenyl)but-2-enamide I-31 (3 mg, 26%) is prepared by using the similar procedure as for I-24. 3-(2-chloropyrimidin-4-yl)-6-methyl-2-phenylpyrazolo[1,5-a]pyridine was used in the third step. LC/MS (ESI) m/z=601 $(M+H)^+$.

Synthesis of I-32

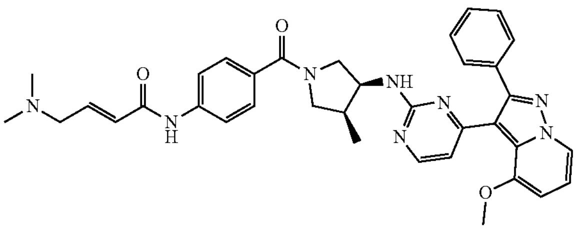 [SMILES: COc1cccn2nc(-c3ccccc3)c(-c3ccnc(N[C@@H]4CN(C(=O)c5ccc(NC(=O)/C=C/CN(C)C)cc5)C[C@@H]4C)n3)c12]

(E)-4-(dimethylamino)-N-(4-((3S,4S)-3-((4-(4-methoxy-2-phenylpyrazolo[1,5-a]pyridin-3-yl)pyrimidin-2-yl)amino)-4-methylpyrrolidine-1-carbonyl)phenyl)but-2-enamide I-32 (7.4 mg, 21%) is prepared by using the similar procedure as for I-1, except 1-amino-3-methoxypyridin-1-ium iodide was used in the second step. $^1$H NMR (500 MHz, DMSO-$d_6$) δ 10.29 (s, 1H), 8.38 (dd, J=9.4, 6.8 Hz, 1H), 8.25 (dd, J=25.3, 5.0 Hz, 1H), 7.70 (d, J=8.6 Hz, 2H), 7.47 (dd, J=23.2, 8.3 Hz, 4H), 7.40-7.18 (m, 4H), 6.92 (q, J=7.7 Hz, 1H), 6.74 (ddd, J=21.8, 15.6, 6.7 Hz, 3H), 6.42-6.22 (m, 1H), 3.86-3.56 (m, 5H), 3.22-3.01 (m, 4H), 2.26 (s, 7H), 1.25 (s, 3H). LC/MS (ESI) m/z=631 $(M+H)^+$.

Example 2. Pulldown Assay Comparing JNK-IN-8 Inhibition with I-11

Figure 2:
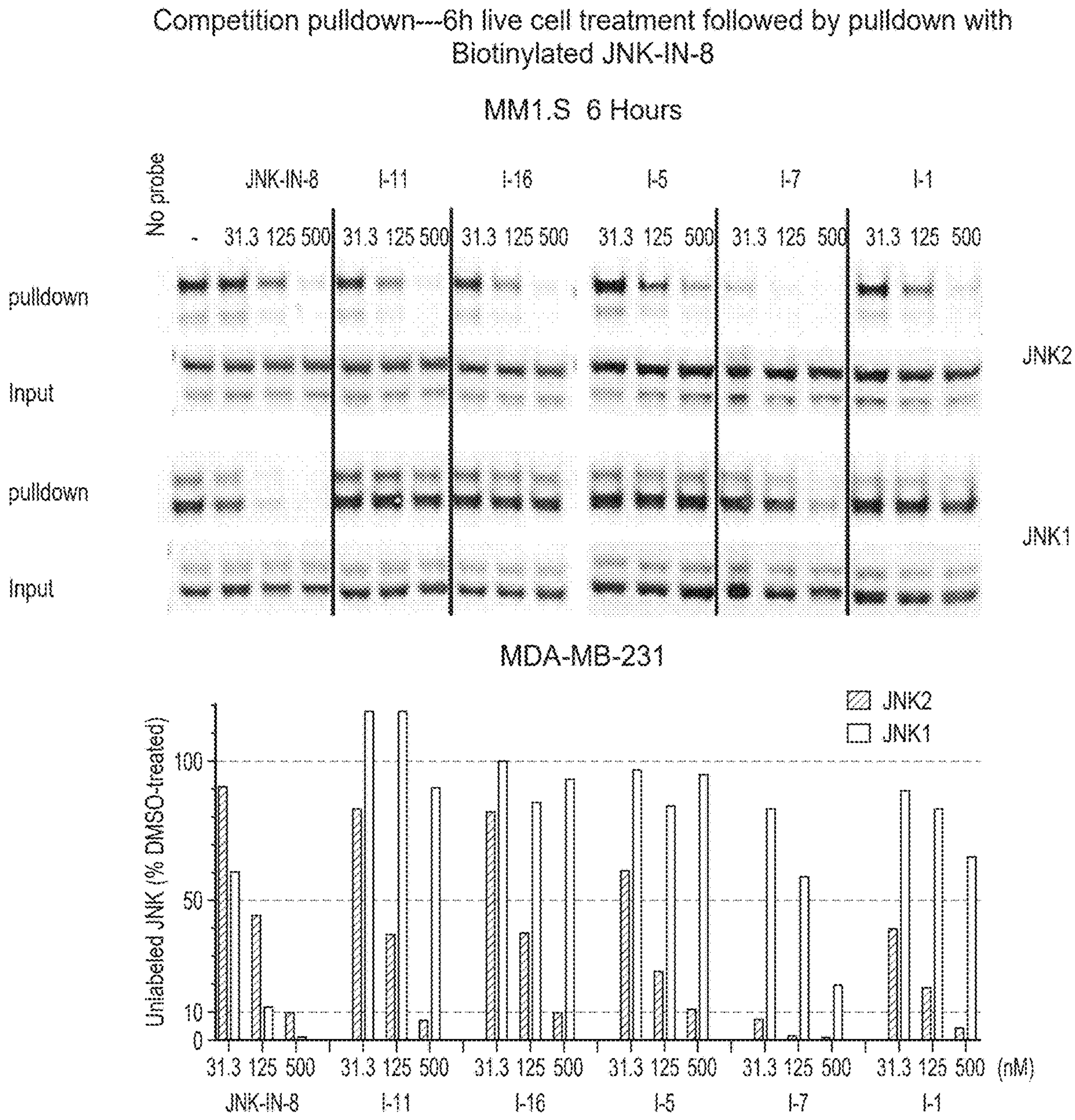
FIG. 2 shows competition pulldown assays using the MDA-MB-231 cell line.

Multiple myeloma cells MM1.S (FIG. 1) or triple negative breast cancer cells MDA-MB-231 (FIG. 2) were treated with I-11 or other testing compounds at indicated doses for 6 h. Whole cell lysates were prepared and 0.5 mg lysate was subject to pulldown of JNK1/2 using Biotinylated JNK-IN-7 (Biotin-JNK-IN-7) at 1 M for 16 h at 4° C. Proteins that were pulled down by the Biotin-JNK-IN-7 was enriched with streptavidin agarose beads by rotation for 2 h at 4° C. Then 25 μl 2×SDS-PAGE loading buffer was added to each sample, and enriched proteins were released from the beads by heating at 95° C. for 10 min. Western blotting was used subsequently to obtain semi-quantitative estimation of the binding of testing compounds

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

(I)

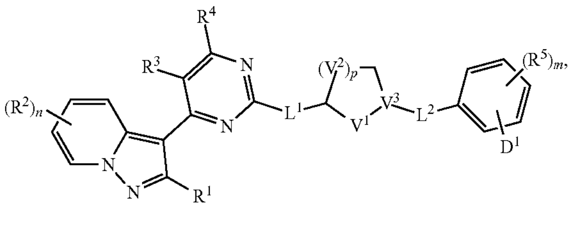

or a pharmaceutically acceptable salt, solvate, hydrate, tautomer, or stereoisomer thereof, wherein:

$R^1$ is optionally substituted aryl;

$R^2$, $R^3$, $R^4$ and $R^5$ are each independently hydrogen, halogen, optionally substituted alkyl, or $-OR^{D1}$, wherein $R^{D1}$ is optionally substituted alkyl;

n is 1;

m is 1;

$L^1$ is $-N(R^a)-$ wherein $R^a$ is hydrogen;

$L^2$ is $-C{=}O-$;

$V^1$ is $C(R^{1a})H$;

$V^2$ is $C(R^{1b})H$;

$V^3$ is N;

$R^{1a}$ and $R^{1b}$ are independently hydrogen, or optionally substituted alkyl;

p is 1;

$D^1$ is a warhead of Formula (i-1):

(i-1)

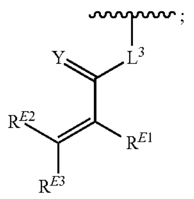

wherein:

$L^3$ is a bond or $NR^{L3a}$, wherein $R^{L3a}$ is hydrogen;

$R^{E1}$ is hydrogen;

$R^{E2}$ is hydrogen;

$R^{E3}$ is selected from the group consisting of hydrogen and $-CH_2N(R^{E3a})_2$, wherein each occurrence of $R^{E3a}$ is independently optionally substituted alkyl; and Y is O.

2. The compound of claim 1, wherein the compound is of Formula (IIa) or (II-b):

(II-a)

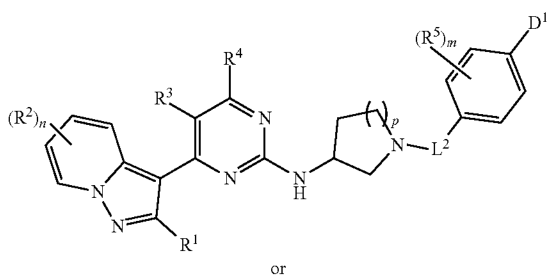

or (II-b)

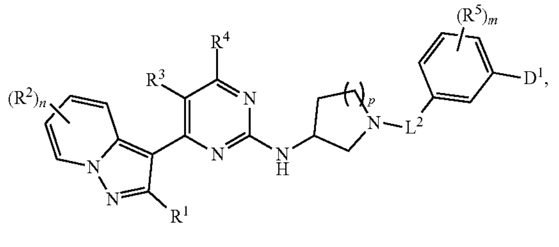

or a pharmaceutically acceptable salt, solvate, hydrate tautomer, or stereoisomer thereof, wherein p is 1.

3. The compound of claim 1, or a pharmaceutically acceptable salt, solvate, hydrate, tautomer, or stereoisomer thereof, wherein $R^3$ is H.

4. The compound of claim 1, or a pharmaceutically acceptable salt, solvate, hydrate, tautomer, or stereoisomer thereof, wherein $R^4$ is H.

5. The compound of claim 1, or a pharmaceutically acceptable salt, solvate, hydrate, tautomer, or stereoisomer thereof, wherein $D^1$ is of the formula:

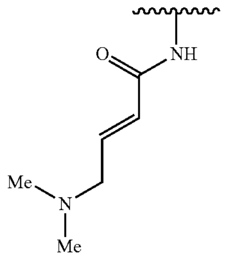

or

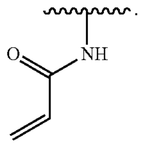

6. The compound of claim 1, or a pharmaceutically acceptable salt, solvate, hydrate, tautomer, or stereoisomer thereof, wherein the compound is of the formula:

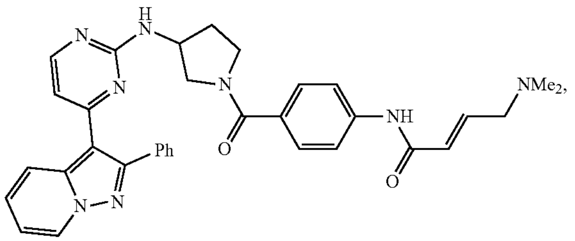

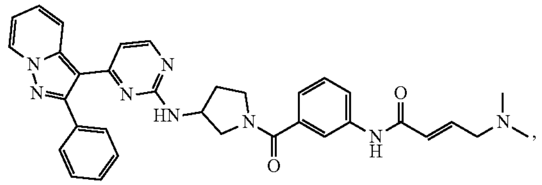

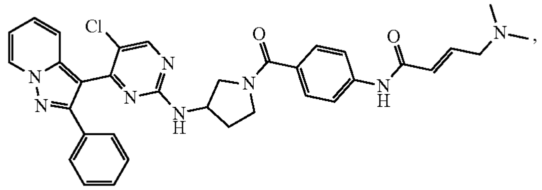

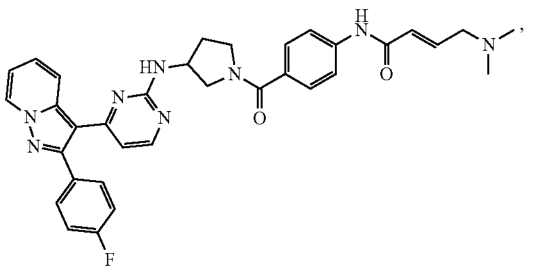

-continued

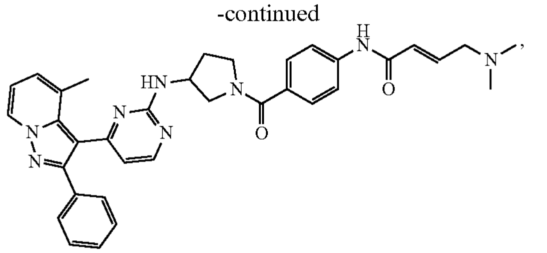

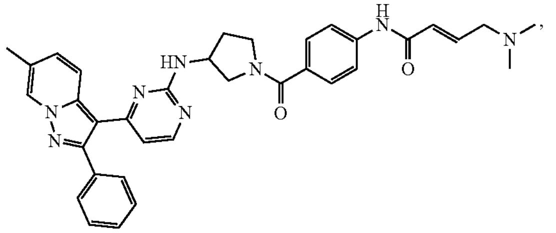

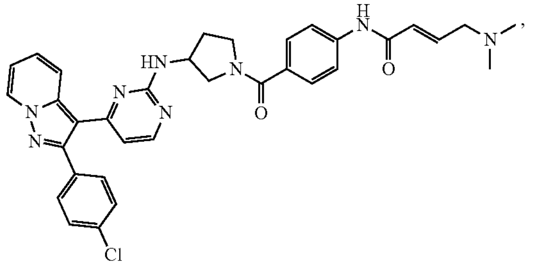

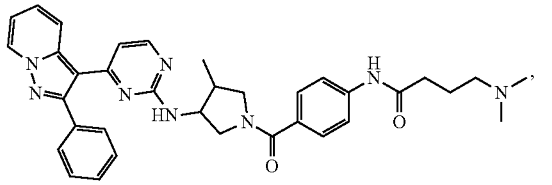

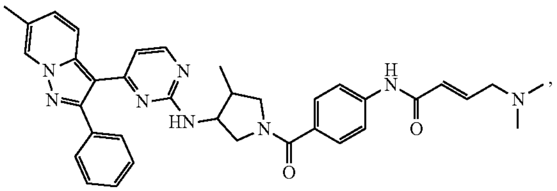

or

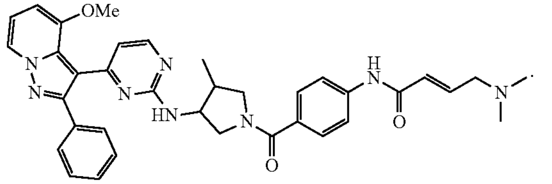

7. A pharmaceutical composition comprising a compound of claim 1, or a pharmaceutically acceptable salt, solvate, hydrate, tautomer, or stereoisomer thereof, and a pharmaceutically acceptable excipient.

8. A compound selected from the group consisting of:

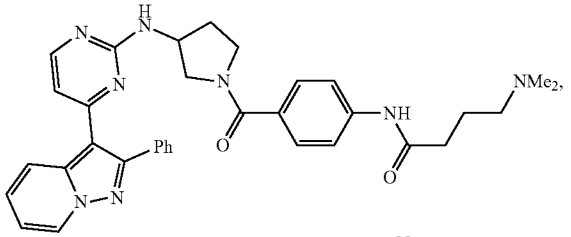

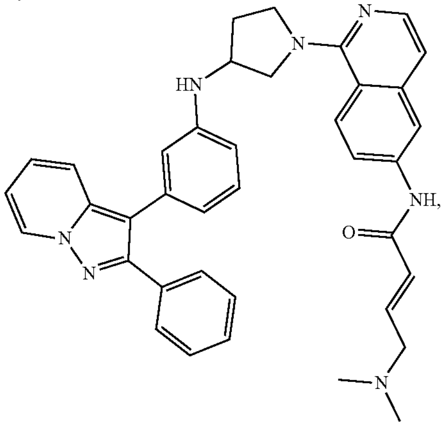

and

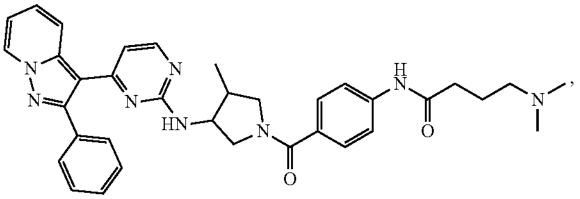

or a pharmaceutically acceptable salt, solvate, hydrate, tautomer, or stereoisomer thereof.

9. A pharmaceutical composition comprising a compound of claim 8, or a pharmaceutically acceptable salt, solvate, hydrate, tautomer, or stereoisomer thereof, and a pharmaceutically acceptable excipient.

10. A method of inhibiting the activity of a c-Jun N-Terminal Kinase (JNK) in a subject or biological sample, the method comprising administering to the subject or contacting the biological sample with a therapeutically effective amount of a compound of claim 1, or a pharmaceutically acceptable salt, solvate, hydrate, tautomer, or stereoisomer thereof, or a pharmaceutical composition thereof.

* * * * *